US012605349B2

(12) United States Patent
Levin et al.

(10) Patent No.: US 12,605,349 B2
(45) Date of Patent: Apr. 21, 2026

(54) METHODS OF TREATING GRADE 3 ASTROCYTOMA

(71) Applicant: Orbus Therapeutics, Inc., Menlo Park, CA (US)

(72) Inventors: Jason D. Levin, Aptos, CA (US); Victor A. Levin, Greenbrae, CA (US); Noymi Yam, Sunnyvale, CA (US)

(73) Assignee: Orbus Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 18/977,389

(22) Filed: Dec. 11, 2024

(65) Prior Publication Data

US 2026/0060950 A1     Mar. 5, 2026

Related U.S. Application Data

(60) Provisional application No. 63/691,306, filed on Sep. 5, 2024.

(51) Int. Cl.
| | |
|---|---|
| *A61K 31/197* | (2006.01) |
| *A61K 9/08* | (2006.01) |
| *A61K 9/48* | (2006.01) |
| *A61K 31/175* | (2006.01) |
| *A61K 47/10* | (2017.01) |
| *A61K 47/12* | (2006.01) |
| *A61K 47/26* | (2006.01) |
| *A61P 35/00* | (2006.01) |
| *C12Q 1/6886* | (2018.01) |

(52) U.S. Cl.
CPC .............. *A61K 31/197* (2013.01); *A61K 9/08* (2013.01); *A61K 9/4858* (2013.01); *A61K 31/175* (2013.01); *A61K 47/10* (2013.01); *A61K 47/12* (2013.01); *A61K 47/26* (2013.01); *A61P 35/00* (2018.01); *C12Q 1/6886* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 4,330,559 | A | 5/1982 | Bey et al. |
| 4,499,072 | A | 2/1985 | Sunkara et al. |
| 4,792,558 | A | 12/1988 | Sunkara et al. |
| 4,925,835 | A | 5/1990 | Heston |
| 4,952,585 | A | 8/1990 | Sunkara et al. |
| 5,002,879 | A | 3/1991 | Bowlin et al. |
| 5,374,658 | A | 12/1994 | Lau |
| 5,571,515 | A | 11/1996 | Scott et al. |
| 5,614,557 | A | 3/1997 | Bey et al. |
| 5,637,323 | A | 6/1997 | Wiltrout et al. |
| 5,853,714 | A | 12/1998 | Deetz et al. |
| 5,880,161 | A | 3/1999 | Basu et al. |
| 5,939,090 | A | 8/1999 | Beaurline et al. |
| 6,083,496 | A | 7/2000 | Poulin et al. |
| 6,199,698 | B1 | 3/2001 | Hetrick et al. |
| 6,258,352 | B1 | 7/2001 | Shimonaka |
| 6,258,845 | B1 | 7/2001 | Gerner et al. |
| 6,277,411 | B1 | 8/2001 | Shaked et al. |
| 6,303,114 | B1 | 10/2001 | Metzger et al. |
| 6,365,166 | B2 | 4/2002 | Beaurline et al. |
| 6,392,098 | B1 | 5/2002 | Frydman et al. |
| 6,602,910 | B2 | 8/2003 | Levenson et al. |
| 6,646,149 | B1 | 11/2003 | Vermeulin et al. |
| 6,653,351 | B2 | 11/2003 | Levin |
| 6,872,852 | B2 | 3/2005 | Burns |
| 6,929,794 | B1 | 8/2005 | Mills et al. |
| 6,936,318 | B2 | 8/2005 | Dent |
| 6,949,679 | B1 | 9/2005 | Poulin et al. |
| 6,963,010 | B2 | 11/2005 | Burns et al. |
| 6,998,502 | B1 | 2/2006 | Majeed et al. |
| 7,030,126 | B2 | 4/2006 | Ramesh et al. |
| 7,094,808 | B2 | 8/2006 | Bergeron, Jr. |
| 7,144,920 | B2 | 12/2006 | Burns et al. |
| 7,160,923 | B1 | 1/2007 | Vermeulin et al. |
| 7,208,528 | B1 | 4/2007 | Vermeulin et al. |
| 7,323,549 | B2 | 1/2008 | Lauder et al. |
| 7,345,196 | B1 | 3/2008 | Majeed et al. |
| 7,374,751 | B1 | 5/2008 | Hancock |
| 7,425,579 | B2 | 9/2008 | Poulin et al. |
| 7,432,302 | B2 | 10/2008 | Burns et al. |
| 7,553,932 | B1 | 6/2009 | Von Herrath et al. |

(Continued)

FOREIGN PATENT DOCUMENTS

| | | |
|---|---|---|
| CN | 1346282 A | 4/2002 |
| CN | 101898978 A | 12/2010 |

(Continued)

OTHER PUBLICATIONS

Hickman et al. ((2023), CDKN2A/B mutations and allele-specific alterations stratify survival outcomes in IDH-mutant astrocytomas, Acta Neuropathologica, 146, 845-847 (Year: 2023).*
NCT02796261 (Study Record Version Jan. 2022) sponsored by Orbus Therapeutics, Inc (Year: 2022).*
NCT03794349 (Study Record Version Sep. 20, 2024) sponsored by Children's Oncology Group (Year: 2024).*
Reis et.al. (2015), CDKN2A Loss Is Associated with Shortened Overall Survival in Lower Grade (World Health Organization II-III) Astrocytomas, J Neuropathol Exp Neurol., 74, 1-15 (442-452). (Year: 2015).*
Afra et al., "Supratentorial Recurrences of Gliomas. Results of Reoperations on Astrocytomas and Oligodendrogliomas", Acta Neurochirurg, Sep. 1978, vol. 43, No. 3, pp. 217-227, 11 Pages.

(Continued)

*Primary Examiner* — Juliet C Switzer
*Assistant Examiner* — Dawanna Shar-Day White
(74) *Attorney, Agent, or Firm* — Wilson Sonsini Goodrich & Rosati

(57) ABSTRACT

Described herein are compounds, pharmaceutical compositions and medicaments comprising such compounds, and methods of using such compounds for the treatment of conditions, diseases, or disorders, e.g., grade 3 astrocytoma.

20 Claims, 8 Drawing Sheets

(56) References Cited

U.S. PATENT DOCUMENTS

| 7,585,947 | B2 | 9/2009 | Morre et al. |
|---|---|---|---|
| 7,589,179 | B2 | 9/2009 | Gillies et al. |
| 7,655,678 | B2 | 2/2010 | Gupta et al. |
| 7,718,764 | B2 | 5/2010 | Wong et al. |
| 7,794,710 | B2 | 9/2010 | Chen et al. |
| 7,858,081 | B2 | 12/2010 | Bernard et al. |
| 7,867,488 | B2 | 1/2011 | Felzmann |
| 7,879,791 | B2 | 2/2011 | Munn et al. |
| 8,012,482 | B2 | 9/2011 | Adams et al. |
| 8,124,084 | B2 | 2/2012 | Lefrancois et al. |
| 8,163,879 | B2 | 4/2012 | Wong et al. |
| 8,173,786 | B2 | 5/2012 | Weiner et al. |
| 8,178,660 | B2 | 5/2012 | Weiner et al. |
| 8,303,965 | B2 | 11/2012 | Lin |
| 8,344,162 | B2 | 1/2013 | Jung et al. |
| 8,415,456 | B2 | 4/2013 | Nellis et al. |
| 8,597,904 | B2 | 12/2013 | Bachmann et al. |
| 8,709,424 | B2 | 4/2014 | Schebye et al. |
| 8,735,553 | B1 | 5/2014 | Li et al. |
| 8,765,462 | B2 | 7/2014 | Medin et al. |
| 8,906,381 | B2 | 12/2014 | Iannacone et al. |
| 8,956,607 | B2 | 2/2015 | Osterroth et al. |
| 8,981,063 | B2 | 3/2015 | Chen |
| 9,006,399 | B2 | 4/2015 | Liu et al. |
| 9,034,319 | B2 | 5/2015 | Teichberg et al. |
| 9,062,111 | B2 | 6/2015 | Nichol et al. |
| 9,072,778 | B2 | 7/2015 | Bachmann |
| 9,079,976 | B2 | 7/2015 | Shirwan et al. |
| 9,090,685 | B2 | 7/2015 | Ledbetter et al. |
| 9,095,608 | B2 | 8/2015 | Kedl et al. |
| 9,132,281 | B2 | 9/2015 | Zeng et al. |
| 9,145,458 | B2 | 9/2015 | Bedinger et al. |
| 9,150,495 | B2 | 10/2015 | Phanstiel, IV |
| 9,161,976 | B2 | 10/2015 | Noelle et al. |
| 9,163,085 | B2 | 10/2015 | Liu et al. |
| 9,233,156 | B2 | 1/2016 | Har-Noy |
| 9,272,025 | B2 | 3/2016 | Fu |
| 9,279,008 | B2 | 3/2016 | Scholler et al. |
| 9,315,559 | B2 | 4/2016 | Spencer et al. |
| 9,320,811 | B2 | 4/2016 | Jure-Kunkel |
| 9,327,014 | B2 | 5/2016 | Gurney et al. |
| 9,375,471 | B2 | 6/2016 | Baudner et al. |
| 9,376,726 | B2 | 6/2016 | Fouchier et al. |
| 10,786,470 | B2 | 9/2020 | Levin et al. |
| 10,945,981 | B2 | 3/2021 | Gerner et al. |
| 11,439,612 | B2 | 9/2022 | Levin et al. |
| 2002/0110590 | A1 | 8/2002 | Shaked et al. |
| 2003/0040526 | A1 | 2/2003 | Levin |
| 2003/0053973 | A1 | 3/2003 | Chou et al. |
| 2003/0203956 | A1 | 10/2003 | Masterrer |
| 2007/0246057 | A1 | 10/2007 | Muller |
| 2008/0027023 | A1 | 1/2008 | Ellervik et al. |
| 2010/0076009 | A1 | 3/2010 | Towner et al. |
| 2010/0120727 | A1 | 5/2010 | Xu |
| 2010/0285012 | A1 | 11/2010 | Dunn, Jr. et al. |
| 2013/0197088 | A1 | 8/2013 | Casero, Jr. et al. |
| 2015/0017231 | A1 | 1/2015 | Phanstiel, IV et al. |
| 2015/0050299 | A1 | 2/2015 | Burns et al. |
| 2015/0094336 | A1 | 4/2015 | Zeldis |
| 2015/0297553 | A1 | 10/2015 | Brown |
| 2015/0306241 | A1 | 10/2015 | Zhu et al. |
| 2021/0263037 | A1* | 8/2021 | Emmett ........... G01N 33/57488 |
| 2023/0338317 | A1 | 10/2023 | Levin et al. |

FOREIGN PATENT DOCUMENTS

| EP | 0046713 | B1 | 12/1985 |
|---|---|---|---|
| EP | 0871441 | B1 | 8/2003 |
| JP | 2004509845 | A | 4/2004 |
| JP | 2005505528 | A | 2/2005 |
| JP | 2010538066 | A | 12/2010 |
| JP | 2012501652 | A | 1/2012 |
| JP | 2013516456 | A | 5/2013 |
| JP | 2018536707 | A | 12/2018 |
| JP | 2019509349 | A | 4/2019 |
| JP | 2019518548 | A | 7/2019 |
| JP | 2019519964 | A | 7/2019 |
| JP | 2019534265 | A | 11/2019 |
| JP | 2023040218 | A | 3/2023 |
| WO | WO-0168076 | A2 | 9/2001 |
| WO | WO-2006108680 | A2 | 10/2006 |
| WO | WO-2016130918 | A1 | 8/2016 |
| WO | WO-2017075576 | A1 | 5/2017 |
| WO | WO-2017165187 | A1 | 9/2017 |
| WO | WO-2018067401 | A1 | 4/2018 |
| WO | WO-2024173768 | A1 | 8/2024 |

OTHER PUBLICATIONS

Alexiou, George et al. Combination Treatment for Glioblastoma With Temozolomide, DFMO and Radiation. Journal of Balkan Union of Oncology vol. 24,1: pp. 397-404 (2019).

Alhonen-Hongisto et al., "Intracellular Putrescine and Spermidine Deprivation Induces Increased Uptake of the Natural Polyamines and Methylglyoxal Bis(guanylhydrazone)", Biochemical Journal, 1980, vol. 192, retrieved on Jul. 18, 2016 from http://www.biochemj.org/content/ppbiochemj/192/3/941.full.pdf , 5 Pages.

Auvinen et al., "Ornithine Decarboxylase Activity is Critical for Cell Transformation", Nature, 1992, vol. 360, pp. 355-358, 4 Pages.

Bachmann et al., "Clinical Applications of Polyamine-Based Therapeutics", Polyamine Drug Discovery, (P.M. Woster & R.A. Casero, Jr., eds., RSC Publishing, 1992), ch. 11, pp. 257-276, 20 Pages.

Bartholeyns et al., "Effects of a-Difiuoromethylornithine Alone and Combined with Adriamycin or Vindesine on L1210 Leukemia in Mice, EMT6 Solid Tumors in Mice and Solid Tumors Induced by Injection of Hepatoma Tissue Culture Cells in Rats", Cancer Research, Dec. 1981, vol. 41, retrieved on Jul. 18, 2016 from http://cancerres.aacrjournals.org/content/canres/41/12_Part_1/5158.full.pdf, 4 Pages.

Bartholeyns, "Treatment of Metastatic Lewis Lung Carcinoma with dl-a-Difluoromethylornithine", European Journal of Clinical Oncology, Apr. 1983, vol. 19, No. 4, pp. 567-572, 6 Pages.

Bovenburg et al., "Cell-Based Immunotherapy Against Gliomas: From Bench to Bedside", Molecular Therapy, 2013, vol. 21, No. 7, pp. 1297-1305, 9 Pages.

Brandes et al., "Procarbazine and High-Dose Tamoxifen as a Second-Line Regimen in Recurrent High-Grade Skims: a Phase II Study", Journal of Clinical Oncology, Feb. 1999, vol. 17, No. 2, pp. 645-650, 6 Pages.

Brat et al., "Comprehensive, Integrative Genomic Analysis of Diffuse Lower-Grade Gliomas", The new england journal of medicine, Jun. 25, 2015, vol. 372, No. 26, retrieved on Jul. 18, 2016 from http://www.nejm.org/doi/ pdf/10.1056/NEJMoa1402121, 18 Pages.

Bregman et al., "Difluoromethylornithine Enhances Inhibition of Melanoma Cell Growth in Soft Agar by Dexamethasone Clone A Interferon and Retinoic Acid", International Journal of Cancer, Jan. 1986, vol. 37, No. 1, pp. 101-107, 7 Pages.

Bristol-Myers Squibb Labeling VANIQA (Jul. 27, 2000). 10 pages.

Brocks et al., "Intratumor DNA Methylation Heterogeneity Reflects Clonal Evolution in Aggressive Prostate Cancer", Cell Reports, Aug. 7, 2014, vol. 8, No. 3, pp. 798-806, 9 Pages.

Buckner et al., "Phase II Trial of Recombinant Interferon-Alpha-2a and Eflornithine in Patients with Recurrent Glioma", Journal of Neuro-Oncology, Jan. 1998, vol. 36, No. 1, pp. 65-70, 6 Pages.

Buckner et al., "Phase III Study of Radiation Therapy (RT) with or without Procarbazine, CCNU and Vincristine (PCV) in Low-Grade Glioma: RTOG 9802 with Alliance ECOG and SWOG", Journal of Clinical Oncology, 2014. 2 pages.

Cairncross et al., "Phase III Trial of Chemotherapy Plus Radiotherapy Compared With Radiotherapy Alone for Pure and Mixed Anaplastic Oligodendroglioma: Intergroup Radiation Therapy Oncology Group Trial 9402", Journal of Clinical Oncology, Jun. 20, 2006, vol. 24, No. 18, retrieved on Jul. 18, 2016 from http://jco.ascopubs.org/ content/24/18/2707.full.pdf+html, 8 Pages.

Carbone, P P, et al. Bioavailability Study of Oral Liquid and Tablet Forms of Alpha-Difluoromethylornithine. Clinical Cancer Research. vol. No. 6, Issue No. 10 (2000): pp. 3850-3854.

Carvalho et al., "Effect of DMSO and DFMO on Rat Prostate Tumor Growth", Prostate, 1989, vol. 15, pp. 123-133, 11 Pages.

(56) References Cited

OTHER PUBLICATIONS

CDKN2A/B (p16) Deletion for Mesothelioma or Glioma. [Website] NeoGenomics. [Retrieved on Oct. 10, 2024]. Available at URL: https://neogenomics.com/test-menu/cdkn2ab-p16-deletion-mesothelioma-or-glioma. pp. 1-5.

Celano et al., "Effect of Polyamine Depletion on c-myc Expression in Human Colon Carcinoma Cells", Journal of Biological Chemistry, Apr. 25, 1988, vol. 263, No. 12, retrieved on Jul. 18, 2016 from http://www.jbc.org /content/263/12/5491.full.pdf+html, 4 Pages.

Chamberlain, "Salvage Therapy with Lomustine for Temozolomide Refractory Recurrent Anaplastic Astrocytoma: a Retrospective Study", Journal of Neuro-Oncology, Apr. 2015, vol. 122, No. 2, pp. 329-338, 10 Pages. Published online Jan. 7, 2015.

Chamberlain et al., "A Phase II Trial of Oral Melphalan in Recurrent Primary Brain Tumors", American Journal of Clinical Oncology, 1988, vol. 11, No. 1, pp. 52-54, 3 Pages.

Chamberlain et al., "Salvage Chemotherapy with Bevacizumab for Recurrent Alkylator-Refractory Anaplastic Astrocytoma", Journal of Neuro-Oncology, 2009, vol. 91, No. 3, pp. 359-367, 9 Pages.

Chamberlain et al., "Salvage Chemotherapy with Taxol for Recurrent Anaplastic Astrocytomas", Journal of Neuro-Oncology, May 1999, vol. 43, No. 1, pp. 71-78, 8 Pages.

Chamberlain, Marc, et al. Salvage Chemotherapy with Cyclophosphamide for Recurrent Temozolomide-Refractory Anaplastic Astrocytoma. Cancer. vol. 106, Issue 1 (2006): 172-179.

Chang et al., "Inhibition of Growth of Human or Hamster Pancreatic Cancer Cell Lines by a-Difluoromethylornithine Alone and Combined with cis-Diamminedichloroplatinum(II)", Cancer Research, Nov. 1984, vol. 44, No. 11, retrieved on Jul. 18, 2016 from http://cancerres.aacrjournals.org/content/canres/44/11/5100.full.pdf, 5 Pages.

Cohen, Adam L et al. IDH1 and IDH2 Mutations in Gliomas. Current Neurology and Neuroscience Reports vol. 13,5: 345, 1-13 (2013).

Cohen et al., "Effect of Difluoromethylornithine on the Antiglioma Therapeutic Efficacy of Infra-Arterial BCNU", Journal of neurosurgery, Nov. 1986, vol. 65, No. 5, pp. 671-678, 8 Pages.

Cohen et al., "FDA Drug Approval Summary: Bevacizumab (Avastin) as Treatment of Recurrent Glioblastoma Multiforme", Oncologist, 2009, vol. 14, retrieved on Jul. 18, 2016 from http://theoncologist.alphamedpress.org /content/14/11/1131.full.pdf+html, 9 Pages.

Cohen et al., "Glioma Biology and Molecular Markers", Current Understanding and Treatment of Gliomas, 2015, vol. 163, pp. 15-30, 16 Pages.

Compound Summary: Vaniqa. PubChem CID: 441361. National Center for Biotechnology Information. Accessed Jun. 21, 2020 from: https://pubchem.ncbi.nlm.nih.gov/compound/441361. Created Jun. 24, 2005. 29 pages.

Co-pending U.S. Appl. No. 18/763,639, inventor Levin; Victor A., filed Jul. 3, 2024.

Corn et al., "White Matter Changes Are Correlated Significantly with Radiation Dose: Observations from a Randomized Dose-Escalation Trial for Malignant Glioma (Radiation Therapy Oncology Group 83-02)", Cancer Nov. 15, 1994, vol. 74, No. 10, retrieved on Jul. 18, 2016 from https://www.researchgate.net/publication/15245483_White_matter_changes_are_correlated_significantly_ . . . , 8 Pages.

Crocetti et al., "Epidemiology of Glial and Non-Glial Brain Tumours in Europe", European journal of cancer, Jan. 2012, vol. 48, pp. 1532-1542, 11 Pages.

Danzin et al., "Effect of a-Difluoromethylornithine, an Enzyme-Activated Irreversible Inhibitor of Omithine Decarboxylase on Polyamine Levels in Rat Tissues", Life Sciences, 1979, pp. 519-524, 6 Pages.

Deangelis. Anaplastic Glioma: How to Prognosticate Outcome and Choose a Treatment Strategy. Journal of Clinical Oncology 27(35):5861-5867 (Dec. 10, 2009). Published online ahead of print Nov. 2, 2019.

Decensi et al., "Biologic Activity of Tamoxifen at Low Doses in Healthy Women", Journal of the National Cancer Institute, Oct. 7, 1998, vol. 90, No. 19, retrieved on Jul. 18, 2016 from http://jnci.oxfordjournals.org/content/90/19/1461.full.pdf+html , 19 Pages.

Ellis et al. Current Challenges in Glioblastoma: Intratumour Heterogeneity, Residual Disease, and Models to Predict Disease Recurrence. Frontiers in Oncology, vol. 5, Article 251 (Nov. 16, 2015). 9 pages.

EP17770846.8 Extended European Search Report dated Oct. 14, 2019.

EP17858939.6 Extended European Search Report dated Apr. 14, 2020.

Evageliou et al. Polyamine Antagonist Therapies Inhibit Neuroblastoma Initiation and Progression. Clin Cancer Res 22(17) 4391-4404 (Sep. 1, 2016). With Supplementary Data available at URL: https://aacrjournals.org/clincancerres/article/22/17/4391/120450/Polyamine-Antagonist-Therapies-Inhibit. 12 pages.

Fine et al., "Phase II Trial of Thalidomide and Carmustine for Patients with Recurrent High-Grade Gliomas", Journal of Clinical Oncology, 2003, pp. 2299-2304, 6 Pages.

Fine et al., "Phase II Trial of the Antiangiogenic Agent Thalidomide in Patients with Recurrent High-Grade Gliomas", Journal of Clinical Oncology, 2000, vol. 18, No. 4, retrieved on Jul. 18, 2016 from http://jco.ascopubs.org/ content/18/4/708.full.pdf+html, 8 Pages.

Fozard et al., "Inhibition of Murine Embryonic Development by a-Difluoromethylornithine, an Irreversible Inhibitor of Ornithine Decarboxylase", European Journal of Pharmacology, Aug. 8, 1980, vol. 65, No. 4, pp. 379-391, 13 Pages.

Friedman et al., "Irinotecan Therapy in Adults with Recurrent or Progressive Malignant Glioma", Journal of Clinical Oncology, May 1999, vol. 17, No. 5, pp. 1516-1525, 10 Pages.

Galanis et al., "Phase II Trial of Nitrogen Mustard, Vincristine and Procarbazine in Patients with Recurrent Glioma: North Central Cancer Treatment Group Results", Journal of Clinical Oncology, 1998, pp. 2953-2958, 6 Pages.

Gebhardt et al. Patterns of failure for glioblastoma multiforme following limited-margin radiation and concurrent temozolomide. Radiat Oncol. 2014; 9:130. Published online Jun. 6, 2014. doi: 10.1186/1748-717X-9-130. 6 pages.

Gennaro, Alfonso R. et al. Remington's Pharmaceutical Sciences: a Laboratory Manual, 17th Edition. Mack Publishing Company : 1418 (1985).

Gerner et al., "Polyamines and Cancer: Old Molecules New Understanding", Nature Reviews Cancer, Oct. 2004, pp. 781-792, 12 Pages.

Gerner et al., "Post-Translational Modification of the Protein-Synthesis Initiation Factor elF-4D by Spermidine in Rat Hepatoma Cells", Biochemical Journal, 1986, vol. 239, retrieved on Jul. 18, 2016 from http://www.biochemj.org/ content/ppbiochemj/239/2/379.fultpdf, 8 Pages.

Gohji et al., "Enhanced Inhibition of Colony Formation of Human Renal Cell Carcinoma in Soft Agar by the Combination of a-Difluoromethylornithine and Recombinant g-Interferon", Cancer Research, 1986, vol. 46, retrieved on Jul. 18, 2016 from http://cancerres.aacrjournals.org/content/canres/46/12_Part_1/6264.full.pdf , 5 Pages.

Gutin et al., "Phase II Study of Procarbazine, CCNU and Vincristine Combination Chemotherapy in the Treatment of Malignant Brain Tumors", Cancer, 1975, vol. 35, pp. 1398-1404, 7 Pages.

Haas-Kogan et al., "Epidermal Growth Factor Receptor, Protein Kinase B/Akt and Glioma Response to Erlotinib", Journal of the National Cancer Institute, Jun. 18, 2005, vol. 97, No. 12, retrieved on Jul. 15, 2016 from http://jnci .oxfordjournals.org/content/97/12/880.full.pdf, 8 Pages.

Hayes et al., "Polyamine-Blocking Therapy Reverses Immunosuppression in the Tumor Microenvironment", Cancer Immunol. Research, Mar. 2014, retrieved on Jul. 18, 2016 from http://cancerimmunolres.aacrjournals.org/ content/2/3/274.full.pdf, 13 Pages.

Hung et al., "Sensitization of 9L Rat Brain Gliosarcoma Cells to 1,3-Bis(2-chloroethyl)-1-Nitrosourea by a—Difluoromethylomithine an Ornithine Decarboxylase Inhibitor", Cancer Research, Jul. 1981, retrieved on Jul. 18, 2016 from http://cancerres.aacrjournals.org/content/canres/41/7/2783.full.pdf , 3 Pages.

Hunter et al., "Effect of a-Difluoromethylornithine on 1,3-Bis(2-chloroethyl)-I-nitrosourea and cis-Diamminedichloroplatinum(II)

(56) References Cited

OTHER PUBLICATIONS

Cytotoxicity DNA Interstrand Cross-Linking and Growth in Human Brain Tumor Cell Lines in Vitro", Cancer Research, May 1990, vol. 50, 4 Pages.

IDH1/IDH2 Mutation Analysis by PCR. [Website] NeoGenomics. [Retrieved on Oct. 10, 2024] Available at URL: https://neogenomics.com/test-menu/idh1idh2-mutation-analysis-pcr. pp. 1-5.

Jeltsch et al., "New Concepts in DNA Methylation", Trends Biochem Sci., 2014, vol. 39, No. 7, pp. 310-318, 9 Pages.

Jeremic et al., "Carboplatin and Etoposide Chemotherapy Regimen for Recurrent Malignant Glioma: a Phase II Study", Journal of Clinical Oncology, 1992, pp. 1074-1077, 4 Pages.

Jänne et al., "Polyamines in Rapid Growth and Cancer", Biochimica et Biophysica Acta, Apr. 1978, vol. 473, No. 3-4, pp. 241-293, 53 Pages.

Johnson, Brett, et al. Mutational Analysis Reveals the Origin and Therapy-driven Evolution of Recurrent Glioma. Science. vol. 343, Issue No. 6167 (2014): 189-193.

Jordan. Tamoxifen: a most unlikely pioneering medicine. Nat Rev Drug Discov. Mar. 2003;2(3):205-13.

Jun et al. Effects of polyamine depletion by α-difluoromethylornithine on in vitro and in vivo biological properties of 4T1 murine mammary cancer cells. Breast Cancer Res Treat 107:33-40 (2008). Published online Feb. 27, 2007.

Killela et al. The genetic landscape of anaplastic astrocytoma. Oncotarget. Mar. 2014; 5(6): 1452-1457. Published online Oct. 16, 2013. doi: 10.18632/oncotarget.1505.

Kingsnorth et al., "Effects of α-Difluoromethylornithine and 5-Fluorouracil on the Proliferation of a Human Colon Adenocarcinoma Cell Line", Cancer Research, Sep. 1983, vol. 43, retrieved on Jul. 18, 2016 from http://cancerres.aacrjournals.org/content/canres/43/9/4035.full.pdf , 4 Pages.

Kleihues et al., "The WHO Classification of Tumors of the Nervous System", Journal of Neuropathology & Experimental Neurology, 2002, 61, No. 3, pp. 215-225, 11 Pages.

Koomoa et al., "DFMO/Eflornithine Inhibits Migration and Invasion Downstream of MYCN and Involves p27kip1 Activity in Neuroblastoma", International Journal of Oncology, 2013, vol. 42, retrieved on Jul. 18, 2016 from http://www.ncbi.nlm.nih.gov/pmc/articles/PMC3622674/pdf/ijo-42-04-1219.pdf, 10 Pages.

Koomoa et al., "Ornithine DecarboxylaseInhibition by a-Difluoromethylornithine Activates Opposing Signaling Pathwaysvia Phosphorylation of Both Akt/Protein Kinase B and p27kip1 inNeuroblastoma", Cancer Research Center of Hawaii, Dec. 1, 2008, retrieved on Jul. 18, 2016 from http://citeseerx.ist.psu.edu/viewdoc/download;sessionid=DB165269FD2A8A1F82DC6C035292CE11?doi=10.1.1.585.4781&rep=rep1&ttype=pdf,7 Pages.

Kumar et al., A method to improve the efficacy of topical eflornithine hydrochloride cream, 2016, Drug Delivery, 23(5); pp. 1495-1501, published online: Sep. 3, 2014.

Kumar et al., "Malignant Gliomas: MR Imaging Spectrum of Radiation Therapy- and Chemotherapy-Induced Necrosis of the Brain After Treatment," Radiology 217: 377-384 (2000).

Kyritsis, Athanassios, et al. An Algorithm for Chemotherapy Treatment of Recurrent Glioma Patients After Temozolomide Failure in the General Oncology Setting. Cancer chemotherapy and pharmacology. vol. 67, Issue No. 5(2011): 971-983.

Lee et al., "Phase I Study of Vorinostat in Combination with Temozolomide in Patients with High-Grade Gliomas: North American Brain Tumor Consortium Study 04-03", Clin. Cancer Research 18(21):6032-6039 (Nov. 1, 2012). Epub Aug. 24, 2012.

Leeper, Heather E. et al. IDH mutation, 1p19q codeletion and ATRX loss in WHO grade II gliomas. Oncotarget 6(30):30295-30305 (2015).

Lesser. The Continuous Temozolamide (TMZ) Use in Patients with GBM (2010). Accessed Aug. 28, 2017 at URL https://www.snola.org/images/pdf/the-continuous-tmz-use-in-patients-with-gbm.pdf . 4 pages.

Levin et al. No-49. Final report for evaluable patients treated on DM92-035, Phase III randomized study of post-irradiation PCV versus DFMO-PCV, for anaplastic gliomas (AG). Neuro-Oncology 14(Suppl 6):vi74-vi75 (Oct. 2012).

Levin et al. Phase III Randomized Study of Postradiotherapy Chemotherapy with α-Difluoromethylornithine-Procarbazine, N-(2-Chloroethyl)-N'-cyclohexyl-N-nitrosurea, Vincristine (DFMO-PCV) Versus PCV for Glioblastoma Multiforme. Clinical Cancer Research 6(10):3878-3884 (Oct. 2000).

Levin, Victor A. et al. Clinical importance of eflornithine (α-difluoromethylornithine) for the treatment of malignant gliomas. CNS oncology 7(2):CNS16, 1-13 (2018).

Levin, Victor, et al. Phase I-II Study of Eflornithine and Mitoguazone Combined in the Treatment of Recurrent Primary Brain Tumors. Cancer Treatment Reports. vol. 71, Issue 5 (1987): 459-464.

Levin, Victor, et al. Treatment of Recurrent Gliomas with Eflornithine. Journal of the National Cancer Institute. vol. 84, Issue No. 18 (1992): 1432-1437.

Lewandowska et al. An Analysis of the Prognostic Value of IDH1 (Isocitrate Dehydrogenase 1) Mutation in Polish Glioma Patients. Mol Diagn Ther. 2014; 18(1): 45-53. Published online Aug. 10, 2013. doi: 10.1007/s40291-013-0050-7.

Longee et al., "Treatment of Patients with Recurrent Gliomas with Cyclophosphamide and Vincristine", Journal of Neurosurgery, Apr. 1990, vol. 72, No. 4, pp. 583-588, 6 Pages.

Louis et al., "The 2007 WHO Classification of Tumours of the Central Nervous System", Acta Neuropathol. 114: 97-109 (2007), retrieved on Jul. 18, 2016 from http://www.ncbi.nlm.nih.gov/pmc/articles/PMC1929165/pdf/401_2007_Article_243.pdf , 13 Pages.

Luk et al., "Growth-inhibitory Effects of DL-a-Difluoromethylornithine in the Spectrum of Human Lung Carcinoma Cells in Culture", Cancer Research, Aug. 1982, vol. 42, retrieved on Jul. 18, 2016 from http://cancerres.aacrjournals.org/ content/canres/42/8/3070.full.pdf, 4 Pages.

Marton et al., "Potentiation of the Antitumor Therapeutic Effects of 1,3-Bis(2-chloroethyl)-1-Nitrosourea by a—Difluoromethylornithine an Ornithine Decarboxylase Inhibitor", Cancer Research, Nov. 1981, vol. 41, retrieved on Jul. 18, 2016 from http://cancerres.aacrjournals.org/content/canres/41/11_Part_1/4426.full.pdf, 6 Pages.

Marx et al., "Treatment of Hamster Pancreatic Cancer With a-Difluoromethylornithine, an Inhibitor of Polyamine Biosynthesis", Journal of the National Cancer Institute, 1987, vol. 79, No. 3, pp. 543-548, 6 Pages.

Mazor et al. DNA Methylation and Somatic Mutations Converge on the Cell Cycle and Define Similar Evolutionary Histories in Brain Tumors. Cancer Cell 28(3):307-317 (2015).

Meyers et al., "Association of Cancer-Related Symptoms with Physiological Parameters", Journal of Pain and Symptom Management, Oct. 2002, vol. 24, No. 4, retrieved on Jul. 18, 2016 from http://www.jpsmjournal.com/ article/S0885-3924(02)00501-8/pdf, 3 Pages.

M.J. van den Bent et al., "Phase II Study of First-Line Chemotherapy With Temozolomide in Recurrent Oligodendroglial Tumors: the European Organization for Research and Treatment of Cancer Brain Tumor Group Study 26971," J. Clin. Oncol. 21: 2525-2528 (2003).

M. Prados et al., "Treatment of Recurrent Gliomas with 1,3-Bis(2-Chloroethyl)-1-Nitrosourea and a—Difluoromethylornithine" Neurosurgery, Jun. 1989, vol. 24, No. 6, pp. 806-809, 4 Pages.

Nabors et al., "Central Nervous System Cancers, Version 2.2014: Featured Updates to the NCCN Guidelines", Journal of the National Comprehensive Cancer Network, Nov. 1, 2014, vol. 12, No. 11, pp. 1517-1523, 7 Pages.

Narita, Yoshitaka. Genetic Mutations in Gliomas and Signal Network (Machine-Translated Title). Neurosurgery Breaking News. vol. 19, Issue 9 (2009): 1054-1061 (With English Machine Translation of Abstract).

National Center for Biotechnology Information. PubChem Database. Eflornithine, CID=3009, https://pubchem.ncbi.nlm.nih.gov/compound/Eflornithine (create date Sep. 16, 2004; accessed on Apr. 1, 2020).

(56) References Cited

OTHER PUBLICATIONS

Neelam, et al., Combination of flavone acetic acid (FAA) with adriamycin, cis-platinum and diflouoromethylornithine (DFMO) in vitro against human colon cancer cells. Invest New Drugs. Aug. 1990; 8(3):263-8.

Newton et al., "Comparison Between BCNU and Procarbazine Chemotherapy for Treatment of Gliomas", Journal of Clinical Oncology, Mar. 1993, vol. 15, No. 3, pp. 257-263, 7 Pages.

Newton et al., "Procarbazine Chemotherapy in the Treatment of Recurrent Malignant Astrocytomas After Radiation and Nitrosourea Failure", Neurology, 1990, vol. 40, No. 11, pp. 1743-1746, 4 Pages.

Obaleye et al., Synthesis, Characterization, Crystal Structure and Antimicrobial Evaluation of a Novel -M-X-M-X-Type Infinite Chain 1D Cu(II) Complex with Eflornithine Hydrochloride Hydrate as Ligand, 2014, J. Inorg. Organomet. Polym., 24(5); pp. 827-835, Published online: Jul. 17, 2014.

Ostrom et al., "CBTRUS Statistical Report: Primary Brain and Central Nervous System Tumors Diagnosed in the United States in 2008-2012", Neuro-Oncology, 2015, retrieved on Jul. 18, 2016 from http://neuro-oncology .oxfordjournals.org/content/17/suppl_4/iv1. full.pdf+html, 62 Pages.

PCT/US2017/022718 International Preliminary Report on Patentability dated May 25, 2018.

PCT/US2017/022718 International Search Report and Written Opinion dated Jun. 2, 2017.

PCT/US2017/054450 International Preliminary Report on Patentability dated Oct. 29, 2018.

PCT/US2017/054450 International Search Report and Written Opinion dated Dec. 14, 2017.

PCT/US2024/016110 International Search Report and Written Opinion dated Apr. 22, 2024.

Pera et al., "Comparison of the Biological Effects of Four Irreversible Inhibitors of Ornithine Decarboxylase in Two Murine Lymphocytic Leukemia Cell Lines", Cancer Research, 1986, vol. 46, No. 3, pp. 1148-1154, 7 Pages.

Prados et al., "Procarbazine, Lomustine and Vincristine (PCV) Chemotherapy for Anaplastic Astrocytoma: a Retrospective Review of Radiation Therapy Oncology Group Protocols Comparing Survival With Carmustine or PCV Adjuvant Chemotherapy", Journal of Clinical Oncology, Nov. 1999, vol. 17, No. 11, retrieved on Jul. 18, 2016 from http://jco.ascopubs.org/content/17/11/3389.full.pdf+html , 7 Pages.

Prados et al., "Treatment of Pediatric Low-Grade Gliomas with a Nitrosourea-Based Multiagent Chemotherapy Regimen", Journal of Neuro-Oncology, 1997, vol. 32, No. 3, pp. 235-241, 7 Pages.

Prakash et al., "Combination Chemotherapy Involving a-Difluoromethylornithine and 1-b-d-Arabinofuranosylcytosine n Murine L1210 Leukemia", Cancer Research, 1983, vol. 43, pp. 3192-3196, 5 Pages.

Prakash et al., "Effect of a-Difluoromethylornithine, an Enzyme-activated Irreversible Inhibitor of Ornithine Decarboxylase on L1210 Leukemia in Mice", Cancer Research, Sep. 1978, vol. 38, No. 9, pp. 3059-3062, 4 Pages.

Prakash et al., "Inhibition of EMT6 Tumor Growth by Interference with Polyamine Biosynthesis: Effects of a—Difluoromethyl-Ornithine, an Irreversible Inhibitor of Ornithine Decarboxylase", Life Sciences, Jan. 1980, vol. 26, \Io. 3, pp. 181-194, 14 Pages.

R. Stupp et al., "Anaplastic Astrocytoma in Adults," (2015). Retrieved Jan. 26, 2016 from URL: http://www.startoncology.net/en/professional-area/anaplastic-astrocytoma-in-adults/ . 13 pages.

R. Stupp et al., "Anaplastic Astrocytoma in Adults," Crit. Rev. Oncol./Hematol. 63: 72-80 (2007).

R. Stupp et al., "Optimal Role of Temozolomide in the Treatment of Malignant Gliomas," Curr. Neurol. Neurosci. Rep. 5: 198-206 (2005).

R.A. Casero, Jr. & L.J. Marton, "Targeting Polyamine Metabolism and Function in Cancer and Other Hyperproliferative Diseases," Nature Rev. Drug Disc. 6: 373-390 (2007).

"Randomized Trial of Procarbazine, Lomustine and Vincristine in the Adjuvant Treatment of High-Grade Astrocytoma: a Medical Research Council Trial", By the Medical Research Council Brain Tumour Working Party. Journal of Clinical Oncology, 2001, pp. 509-518, 10 Pages.

R.B. Dinapoli et al., "Phase III Comparative Evaluation of PCNU and Carmustine Combined with Radiation Therapy for High-Grade Glioma," J. Clin. Oncol. 11: 1316-1321 (1993).

Reardon et al., "Phase 1Trial of Gefitinib Plus Sirolimus in Adults with Recurrent Malignant Glioma", Clin. Cancer Res., Feb. 1, 2006, retrieved on Jul. 18, 2016 from http://www.richlab.net/PDF/gefitinib_ccr2006.pdf , 9 Pages.

Regenass et al., "CGP 48664, a New S-Adenosylmethionine Decarboxylase Inhibitor with Broad Spectrum Antiproliferative and Antitumor Activity1", Cancer Research, vol. 54, Jun. 15, 1994, pp. 3210-3217.

R.H. Goldbrunner et al., "PTK787/ZK222584, an Inhibitor of Vascular Endothelial Growth Factor Receptor Tyrosine Kinases, Decreases Glioma Growth and Vascularization," Neurosurgery 55: 426-432 (2004).

Rich et al., "Phase II Trial of Gefitinib in Recurrent Glioblastoma", Journal of Clinical Oncology, Jan. 1, 2004, vol. 22, No. 1, retrieved on Jul. 18, 2016 from http://www.brainlife.org/fulltext/2004/rich_jn040101.pdf , 10 Pages.

R.J. Weinkam & D.A. Shiba, "Metabolic Activation of Procarbazine," Life Sci. 22: 937-946 (1978).

Rodriguez et al., "Reevaluation of Procarbazine for the Treatment of Recurrent Malignant Central Nervous System Tumors", Cancer, Dec. 1989, vol. 64, No. 12, pp. 2420-2423, 4 Pages.

Ross et al. Systematic variation in gene expression patterns in human cancer cell lines. Nat Genet 24:227-235 (Mar. 2000).

S. Genedani et al., "Convulsive Syndrome Induced by the Intracerebroventricular Injection of a-Difluoromethylornithine in Rats," Acta Pharmacol. Toxicol. 56: 250-253 (1985).

S. Kobayashi et al., "Variable Response to 1,3-bis(2-Chloroethyl)-1-Nitrosourea of Human Glioma Cells Sorted According to DNA Content," J. Neuro-Oncol. 2: 5-11 (1984).

S. Yust-Katz et al., "Phase 1/1b Study of Lonafarnib and Temozolomide in Patients With Recurrent or Temozolomide Refractory Glioblastoma," Cancer 119: 2747-2753 (2013).

S.A. Leibel et al., "The Role of Radiation Therapy in the Treatment of Astrocytomas," Cancer 35: 1551-1557 (1975).

Samal, Katherine, et al., AMXT-1501, a Novel Polyamine Transport Inhibitor Synergizes with DFMO in Inhibiting Neuroblastoma Cell Proliferation by Targeting Both Ornithine Decarboxylase and Polyamine Transport. International Journal of Cancer. vol. 133 (2013): pp. 1323-1334.

S.C. Schold, Jr. et al., "Phase II Diaziquone-Based Chemotherapy Trials in Patients With Anaplastic Supratentorial Astrocytic Neoplasms," J. Clin. Oncol. 5: 464-471 (1987).

S.C. Schold, Jr. et al., "Treatment of Patients with Recurrent Primary Brain Tumors with AZQ," Neurology 34: 615-619 (1984).

Scott et al., "Validation and Predictive Power of Radiation Therapy Oncology Group (RTOG) Recursive Partitioning Analysis Classes for Malignant Glioma Patients: a Report Using RTOG 90-06", International journal of radiation oncology, biology, physics, Jan. 1, 1998, vol. 40, No. 1, pp. 51-55, 5 Pages.

S.E. Kaba et al., "The Treatment of Recurrent Cerebral Gliomas with All-Trans-Retinoic Acid (Tretinoin)," J. Neuro-Oncol. 34: 145-151 (1997).

Sehmer et al., "Incidence of Glioma in a Northwestern Region of England, 2006-2010", Neuro-Oncology, 2014, retrieved on Jul. 18, 2016 from http://www.ncbi.nlm.nih.gov/pmc/articles/PMC4057131/pdf/not301.pdf , 4 Pages.

Sexauer et al., "Cisplatin in Recurrent Pediatric Brain Tumors. A POG Phase II study. A Pediatric Oncology Group study", Cancer, 1985, vol. 56, No. 7, pp. 1497-1501, 5 Pages.

Shantz et al., "Regulation of Ornithine Decarboxylase During Oncogenic Transformation: Mechanisms and Therapeutic Potential", Amino Acids, 2007, vol. 33, No. 2, pp. 213-223, 11 Pages.

Shiba et al. "Quantitative Analysis of Procarbazine, Procarbazine Metabolites and Chemical Degradation Products with Application to Pharmacokinetic Studies", Journal of Chromatography B: Biomedical Sciences and Applications, May 14, 1982, vol. 229, No. 2, pp. 397-407, 11 Pages.

(56)          References Cited

OTHER PUBLICATIONS

Siimes et al., "Synergistic Action of Two Polyamine Metabolites Leads to a Rapid Therapeutic Response in Childhood Leukemia", International Journal of Cancer, 1981, vol. 28, No. 5, pp. 567-570, 4 Pages.

S. Lönn et al., "Incidence Trends of Adult Primary Intracerebral Tumors in Four Nordic Countries," Int. J. Cancer 108: 450-455 (2004).

S.M. Chang et al., "Phase II Study of Phenylacetate in Patients with Recurrent Malignant Glioma: a North American Brain Tumor Consortium Report," J. Clin. Oncol. 17: 984-990 (1999).

S.M. Oredsson et al., "Differential Potentiation of 1,3-Bis(2-chloroethyl)-1-nitrosourea by a-Difluoromethylornithine in Chloroethylnitrosourea-Sensitive and -Resistant 9L Rat Brain Tumor Cells in Vitro," Cancer Res. 43: 3576-3578 (1983).

S.M. Oredsson et al., "Implications for a Reduced DNA-Elongation Rate in Polyamine-Depleted Cells," Eur. J. Biochem. 190: 483-489 (1990).

S.R. Chowdhury et al., "The Role of a-Difluoromethyl Ornithine as an Adjuvant to Immunotherapy in Mice Bearing Transplantable Tumors," Neoplasma 41: 159-161 (1994).

Stern et al., "Vaccination with Tumor Peptide in CpG Adjuvant Protects via IFN-Gamma-Dependent CD4 Cell Immunity", J. Immunol, Jun. 2002, vol. 168, pp. 6099-6105, 7 Pages.

Sunkara et al., "Antimetastatic Activity of dl-a-Difluoromethylornithine, an Inhibitor of Polyamine Biosynthesis in Mice", Cancer Research, 1987, vol. 47, pp. 933-935, 3 Pages.

Sunkara et al., "Selective Killing of Transformed Cells in Combination with Inhibitors of Polyamine Biosynthesis and S-Phase Specific Drugs", Cell Biology International Reports, Oct. 1981, vol. 5, No. 10, pp. 991-997, 7 Pages.

Sunkara et al., "Inhibition of Polyamine Biosynthesis by a-Difluoromethyl Ornithine Potentiates the Cytotoxic Effect of Arabinosyl Cytosine in Hela Cells", Biochemical and Biophysical Research Communications, 1980, vol. 95, pp. 423-430, 8 Pages.

Sunkara et al., "Potentiation of Antitumor and Antimetastatic Activities of a-Difluoromethylornithine by Interferon Inducers", Cancer Research, Jul. 1984, vol. 44, retrieved on Jul. 18, 2016 from http://cancerres.aacrjournals.org /content/canres/44/7/2799.full.pdf, 4 Pages.

Sunkara et al., "Tumor Suppression with a Combination of a-Difluoromethyl Ornithine and Interferon", Science, 1983, vol. 219, No. 4586, pp. 851-853, 3 Pages.

T. Coyle et al., "Mechlorethamine, Vincristine, and Procarbazine Chemotherapy for Recurrent High-Grade Glioma in Adults: a Phase II Study," J. Clin. Oncol. 8: 2014-2018 (1990).

Tabor et al. "Polyamines", Annual Review of Biochemistry, Jul. 1984, vol. 53, pp. 749-790, 42 Pages.

Tanaka et al. Update on Glioma Treatments in the United States. Journal of Neurosurgery, vol. 22, No. 8, pp. 590-596 (2013). English abstract.

T.E. Elliott et al., "Phase II Study of Ifosfamide with Mesna in Adult Patients with Recurrent Diffuse Astrocytoma," J. Neuro-Oncol. 10: 27-30 (1991).

Temozolomide (Rx). Medscape.com. (Website) Feb. 3, 2023. Retrieved May 17, 2024 at URL: https://web.archive.org/web/20230203143814/ https://reference.medscape.com/drug/temodar-temozolomide-342229. 4 pages.

T.F. Cloughesy et al., "Phase I Trial of Tipifarnib in Patients With Recurrent Malignant Glioma Taking Enzyme-Inducing Antiepileptic Drugs: a North American Brain Tumor Consortium Study," J. Clin. Oncol. 23: 6647-6656 (2005).

Thorne et al., "Epidermal Growth Factor Receptor Targeting and Challenges in Glioblastoma", Neuro-Oncology, 2016, vol. 18, No. 7, pp. 914-918, 5 Pages.

Traxler et al., "AEE788: a Dual Family Epidermal Growth Factor Receptor/ErbB2 and Vascular Endothelial Growth Factor Receptor Tyrosine Kinase Inhibitor with Antitumor and Antiangiogenic Activity", Cancer Research, 2004, vol. 64, pp. 4931-4941.

U. Thanarajasingam et al., "Delivery of CCL21 to Metastatic Disease Improves the Efficacy of Adoptive T-Cell Therapy," Cancer Res. 67: 300-308 (2007).

U.S. Appl. No. 15/218,149 Office Action dated Jan. 11, 2017.

U.S. Appl. No. 15/218,149 Office Action dated Sep. 8, 2017.

U.S. Appl. No. 15/218,149 Office Action dated May 22, 2018.

U.S. Appl. No. 15/218,149 Office Action dated May 24, 2019.

U.S. Appl. No. 15/218,149 Office Action dated Nov. 26, 2018.

U.S. Appl. No. 15/218,149 Office Action dated Sep. 10, 2019.

U.S. Appl. No. 16/087,195 Office Action dated Jan. 27, 2021.

U.S. Appl. No. 16/087,195 Office Action dated May 21, 2020.

U.S. Appl. No. 16/087,195 Office Action dated Sep. 17, 2020.

U.S. Appl. No. 16/087,195 Office Action dated Feb. 13, 2020.

U.S. Appl. No. 16/339,664 Ex Parte Quayle Action dated Jun. 25, 2020.

U.S. Appl. No. 16/339,664 Notice of Allowance dated Jul. 31, 2020.

U.S. Appl. No. 16/339,664 Notice of Allowance dated Sep. 4, 2020.

U.S. Appl. No. 17/002,117 Notice of Allowance dated Aug. 15, 2022.

U.S. Appl. No. 17/002,117 Notice of Allowance dated Jun. 1, 2022.

U.S. Appl. No. 17/002,117 Notice of Allowance dated May 4, 2022.

V.A. Levin & C.B. Wilson, "Nitrosourea Chemotherapy for Primary Malignant Gliomas," Cancer Treat. Rep. 60: 719-724 (1976).

V.A. Levin & M.D. Prados, "Treatment of Recurrent Gliomas and Metastatic Brain Tumors with a Polydrug Protocol Designed to Combine Nitrosourea Resistance," J. Clin. Oncol. 10: 766-771 (1992).

V.A. Levin et al., "CNS Anticancer Drug Discovery and Development Conference White Paper," Neuro-Oncology 17: vi1-vi26 (2015).

V.A. Levin et al., "CNS Toxicity and CSF Pharmacokinetics of Intraventricular DFMO and MGBG in Beagle Dogs," Cancer Chemother. Pharmacol. 13: 200-205 (1984).

V.A. Levin et al., "Impact of Phase II Trials with Progression-Free Survival as End-Points on Survival-Based Phase III Studies in Patients with Anaplastic Gliomas," BMC Cancer 7: 106 (2007). 7 pages.

V.A. Levin et al., "Modified Procarbazine, CCNU, and Vincristine (PCV 3) Combination Chemotherapy in the Treatment of Malignant Brain Tumors," Cancer Treat. Rep. 64: 237-241 (1980).

V.A. Levin et al., "PCNU Treatment for Recurrent Malignant Gliomas," Cancer Treat. Rep. 68: 969-973 (1984).

V.A. Levin et al., "Phase II Study of Accelerated Fractionation Radiation Therapy with Carboplatin Followed by PCV Chemotherapy for the Treatment of Anaplastic Gliomas," Int. J. Radiation Oncol. Biol. Phys. 53: 58-66 (2002).

V.A. Levin et al., "Phase II Study of Combined Carmustine, 5-Fluorouracil, Hydroxyurea, and 6-Mercaptopurine (BFHM) for the Treatment of Malignant Gliomas," Cancer Treat. Rep. 70: 1271-1274 (1986).

V.A. Levin et al., "Phase III Randomized Study of Postradiotherapy Chemotherapy with Combination a-Difluoromethylornithine-PCV versus PCV for Anaplastic Gliomas," Clin. Cancer Res. 9: 981-990 (2003).

V.A. Levin et al., "Superiority of Post-Radiotherapy Adjuvant Chemotherapy with CCNU, Procarbazine, and Vincristine (PCV) Over BCNU for Anaplastic Gliomas: NCOG 6G61 Final Report," Int. J. Radiation Oncol. Biol. Phys. 18: 321-324 (1990).

Van Tassel et al., "MR of Toxic Effects of Accelerated Fractionation Radiation Therapy and Carboplatin Chemotherapy for Malignant Gliomas", American Journal of Neuroradiology, Apr. 1995, vol. 16, retrieved on Jul. 18, 2016 from http://citeseerx.ist.psu.edu/viewdocklownload?doi=10.1.1.560.599&rep=rep1&type=pdf , 12 Pages.

Van Thuijl et al. Evolution of DNA repair defects during malignant progression of low-grade gliomas after temozolomide treatment. Acta Neuropathol. Apr. 2015; 129(4): 597-607. doi:10.1007/s00401-015-1403-6.

V.B. Grossie, Jr. et al., "Effect of Intravenous a-Difluoromethylornithine on the Polyamine Levels of Normal Tissue and a Transplantable Fibrosarcoma," Cancer Res. 47: 1836-1840 (1987).

Vidaki et al., "Forensic DNA Methylation Profiling-Potential Opportunities and Challenges", Forensic Sci Int Genet, Sep. 2013, vol. 7, No. 5, pp. 499-507, 9 Pages.

(56) References Cited

OTHER PUBLICATIONS

Vigneswaran et al., "Beyond the World Health Organization Grading of Infiltrating Gliomas: Advances in the Molecular Genetics of Glioma Classification", Annals of translational medicine 3(7):95 (2015). 13 pages.

Vippagunta, et al. Crystalline Solids. Advanced Drug Delivery Reviews 48(1):3-26 (2001).

Visser et al., "Survival of Adults with Primary Malignant Brain Tumours in Europe: Results of the EUROCARE-5 Study", European Journal of Cancer, Oct. 1, 2015, vol. 51, No. 15, pp. 2231-2241, 11 Pages.

Wallace et al., "A Perspective of Polyamine Metabolism", Biochemical Journal, 2003, retrieved on Jul. 18, 2016 from http://www.ncbi.nlm.nih.gov/pmc/articles/PMC1223767/pdf/13678416.pdf, 14 Pages.

W.D. Heston et al., "Growth Inhibition of a Prostate Tumor by a-Difluoromethylornithine and by Cyclophosphamide," Cancer Lett. 16: 71-79 (1982).

Weitzner et al., "Psychosocial Functioning and Quality of Life in Patients with Brain Tumors", Journal of Neurosurgery, Jan. 1996, vol. 84, No. 1, pp. 29-34, 6 Pages.

Weller et al. Standards of care for treatment of recurrent glioblastoma—are we there yet? Neuro-Oncology 15(1):4-27 (2013). Advance Access publication Nov. 7, 2012.

Wilson et al., "Single-Agent Chemotherapy of Brain Tumors: a Five-Year Review", Arch. Neurol., Nov. 1976, vol. 33, No. 11, pp. 739-744, 6 Pages.

W.J. Bodell, "Formation of DNA Adducts and Induction of lad Mutations in Big Blue Rat-2 Cells Treated with Temozolomide: Implications for the Treatment of Low-Grade Adult and Pediatric Brain Tumors," Cancer Epidemiol. Biomarkers Prevent. 12: 545-551 (2003).

W.K.A. Yung et al., "Intravenous BCNU and AZQ in Patients with Recurrent Malignant Gliomas," J. Neuro-Oncol. 7: 237-240 (1989).

W.K.A. Yung et al., "Intravenous Carboplatin for Recurrent Malignant Glioma: a Phase II Study," J. Clin. Oncol. 9: 860-864 (1991).

W.K.A. Yung et al., "Intravenous Recombinant Interferon Beta in Patients with Recurrent Malignant Glioma: a Phase I/II Study," J. Clin. Oncol. 9: 1945-1949 (1991).

W.K.A. Yung et al., "Multicenter Phase II Trial of Temozolomide in Patients with Anaplastic Astrocytoma or Anaplastic Oligoastrocytoma at First Relapse," J. Clin. Oncol. 17: 2762-2771 (1999).

W.K.A. Yung et al., Treatment of Recurrent Malignant Gliomas with High-Dose 13-cis-Retinoic Acid, Clin. Cancer Res. 2: 1931-1935 (1996).

W.L McKeehan et al., "Prostatic Binding Protein, Polyamine, and DNA Synthesis in Rat Ventral Prostate Cells," Prostate 3: 231-246 (1982).

W. Müller et al., "Supratentorial Recurrences of Gliomas. Morphological Studies in Relation to Time Intervals with Astrocytomas," Acta Neurochirurg. 37: 75-91 (1977).

W. Müller et al., "Supratentorial Recurrences of Gliomas. Morphological Studies in Relation to Time Intervals with Oligodendrogliomas," Acta Neurochirurg. 39: 15-25 (1977).

Wong et al., "Outcomes and Prognostic Factors in Recurrent Glioma Patients Enrolled onto Phase II Clinical Trials", Journal of Clinical Oncology, Aug. 1999, vol. 17, No. 8, retrieved on Jul. 18, 2016 from http://www.brainlife.org/ fulltext/1999/wong_et990801.pdf, 7 Pages.

Wright, et al. Protein-tyrosine phosphatases in the vessel wall: differential expression after acute arterial injury. Arterioscler Thromb Vasc Biol. May 2000;20(5):1189-98.

Yip et al. MSH6 Mutations Arise in Glioblastomas during Temozolomide Therapy and Mediate Temozolomide Resistance. Clin Cancer Res 15(14):4622-4629 (Jul. 15, 2009). Epub Jul. 7, 2009. Correction published in Clin Cancer Res 19(16):4544 (Aug. 15, 2013). Correction published online Jul. 19, 2013.

Zhu et al. IDH1 R132H Mutation Enhances Cell Migration by Activating AKT-mTOR Signaling Pathway, but Sensitizes Cells to 5-FU Treatment as NADPH and GSH Are Reduced. PLoS One. 2017; 12(1): e0169038. Published online Jan. 4, 2017. doi: 10.1371/journal.pone.0169038. 13 pages.

Gilbert, Mark R. et al. A Randomized Trial of Bevacizumab for Newly Diagnosed Glioblastoma. The New England Journal of Medicine 370(8):699-708 (2014).

Noor, Humaira et al. TP53 Mutation Is a Prognostic Factor in Lower Grade Glioma and May Influence Chemotherapy Efficacy. Cancers (Basel) 13(21):5362, 1-28 (2021).

Stupp, Roger, et al. Cilengitide combined with standard treatment for patients with newly diagnosed glioblastoma and methylated O-methylguanine- DNA methyltransferase (MGMT) gene promoter: Key results of the multicenter, randomized, open-label, controlled, phase III Centric study. Journal of Clinical Oncology 31(18_suppl):LBA2009 (2013). Meeting abstract.

Medina, Deyber A. V. et al. Thermal investigation on polymorphism in sodium saccharine. Journal of thermal analysis and calorimetry 117(1):361-367(2014).

U.S. Appl. No. 17/818,951 Office Action dated May 19, 2025.

Co-pending U.S. Appl. No. 19/157,137, inventors Levin; Victor et al., filed Aug. 15, 2025.

Huang, L Eric et al. Impact of CDKN2A/B Homozygous Deletion on the Prognosis and Biology of IDH-Mutant Glioma. Biomedicines 10(2):246, 1-8 (2022).

U.S. Appl. No. 62/975,609, inventors Emmett; Mark R. et al., filed Feb. 12, 2020.

Yuile, Alexander. et al. CDKN2A/B Homozygous Deletions in Astrocytomas: a Literature Review. Current Issues in Molecular Biology 45(7):5276-5272 (2023).

ClinicalTrials.gov Identifier: NCT02796261. Study to Evaluate Eflornithine + Lomustine vs Lomustine in Recurrent Anaplastic Astrocytoma (AA) Patients (STELLAR), Version 21, Jan. 19, 2022 [retrieved on Dec. 17, 2025]. Available at https://clinicaltrials.gov/study/NCT02796261?tab=history&a=21#version-content-panel pp. 1-18.

PCT/US2025/044866 International Search Report and Written Opinion dated Nov. 19, 2025.

U.S. Appl. No. 17/818,951 Office Action dated Sep. 30, 2025.

* cited by examiner

METHODS OF TREATING GRADE 3 ASTROCYTOMA

CROSS-REFERENCE

This application claims the benefit of U.S. Provisional Application No. 63/691,306 filed Sep. 5, 2024, which is incorporated herein by reference.

FIELD

Described herein are compounds, pharmaceutical compositions and medicaments comprising such compounds, and methods of using such compounds for the treatment of conditions, diseases, or disorders that are characterized by certain genetic profiles, e.g., mutant IDH, no homozygous deletion of CDKN2A/B, etc.

BACKGROUND

Cancer treatment is associated with multiple complex challenges, including lack of efficacy and severe toxicities often experienced by patients. For example, gliomas, such as astrocytomas, are exceedingly difficult to treat, and patients have extremely low survival rates with very short life expectancies. In 2021, World Health Organization (WHO) re-reclassified gliomas based on the genetic profile of these malignancies. Specifically, grade 3 astrocytoma is characterized by IDH (e.g., IDH1, IDH2) mutation in combination with no homozygous deletion of CDKN2A/B. Most astrocytomas respond to cytotoxic chemotherapy to a variable extent. However, since chemotherapy agents vary in their ability to cross normal cerebral vasculature (blood-brain-barrier) as well as tumor capillary beds (blood-tumor barrier), many drugs tested over the years have failed to produce meaningful antitumor efficacy, because they were unable to reach invading tumor cells in sufficient dose and for sufficient time. Surgical intervention is rarely a viable interventional strategy on its own, as rapid growth into surrounding normal brain tissue can complicate surgical access; recurrence is high in cases where tumor removal is incomplete. The addition of radiation therapy has provided some improvement in survival outcomes following surgery but is infrequently curative. Combination chemotherapies have likewise shown modest to poor therapeutic effect thus far. A wide range of chemotherapeutic agents and combinations of chemotherapeutic agents have been employed with or without additional treatment (e.g., surgical intervention); however, no treatment regimen or strategy has succeeded in extending lifespan of subjects having advanced gliomas (e.g., grade 3 astrocytoma) beyond the modest benefits of treatments developed four decades ago. Worse even, to date, there is no approved nonsurgical treatment available for patients who have recurrent astrocytoma after receiving prior treatment, e.g., external beam radiation therapy (EBRT) and an adjuvant temozolomide regimen. There is an unmet need for new treatment strategies.

SUMMARY

Among other things, the present disclosure provides an insight that effectiveness of cancer treatment depends on the ability to select a patient population that has the best chance to respond to treatment with a particular anticancer agent. Genetic characterization of tumors based on biomarker research enables patient selection.

In one aspect, the present disclosure provides a method of treating cancer, comprising administering to a subject an ornithine decarboxylase inhibitor.

In one aspect, the present disclosure provides a method of treating cancer, comprising administering to a subject an ornithine decarboxylase inhibitor and a second therapeutic agent or treatment including a chemotherapeutic agent, an immunotherapy agent, or radiation therapy.

In one aspect, the present disclosure provides a method of treating cancer, comprising administering to a subject an ornithine decarboxylase inhibitor and a chemotherapeutic agent.

In one aspect, the present disclosure provides a method of treating cancer, comprising administering to a subject an ornithine decarboxylase inhibitor and an alkylating agent.

In one aspect, the present disclosure provides a method of treating cancer, comprising administering to a subject eflornithine or a salt thereof and a chemotherapeutic agent.

In one aspect, the present disclosure provides a method of treating cancer, comprising administering to a subject eflornithine or a salt thereof and lomustine.

In another aspect, the present disclosure provides a method of treating cancer in a subject with mutant IDH (e.g., IDH1, IDH2) and no homozygous deletion of CDKN2A/B genes, comprising administering to the subject eflornithine or a salt thereof and a chemotherapeutic agent.

In another aspect, the present disclosure provides a method of treating cancer in a subject with mutant IDH1 and no homozygous deletion of CDKN2A/B genes, comprising administering to the subject eflornithine or a salt thereof and a chemotherapeutic agent.

In another aspect, the present disclosure provides a method of treating cancer in a subject with mutant IDH2 and no homozygous deletion of CDKN2A/B genes, comprising administering to the subject eflornithine or a salt thereof and a chemotherapeutic agent.

In another aspect, the present disclosure provides a method of treating a cancer characterized by mutant IDH (e.g., IDH1, IDH2) and no homozygous deletion of CDKN2A/B genes, comprising administering to a subject eflornithine or a salt thereof and lomustine.

In another aspect, the present disclosure provides a method of treating a cancer characterized by mutant IDH1 and no homozygous deletion of CDKN2A/B genes, comprising administering to a subject eflornithine or a salt thereof and lomustine.

In another aspect, the present disclosure provides a method of treating a cancer characterized by mutant IDH2 and no homozygous deletion of CDKN2A/B genes, comprising administering to a subject eflornithine or a salt thereof and lomustine.

In another aspect, the present disclosure provides a method of treating cancer in a subject with no homozygous deletion of CDKN2A/B genes, comprising administering to the subject an ornithine decarboxylase inhibitor.

In another aspect, the present disclosure provides a method of treating cancer in a subject with intact CDKN2A/B genes, comprising administering to the subject an ornithine decarboxylase inhibitor.

In another aspect, the present disclosure provides a method of treating cancer in a subject with mutant IDH (e.g., IDH1, IDH2) and no homozygous deletion of CDKN2A/B genes, comprising administering to the subject an ornithine decarboxylase inhibitor.

In another aspect, the present disclosure provides a method of treating cancer in a subject with mutant IDH1 and no homozygous deletion of CDKN2A/B genes, comprising administering to the subject an ornithine decarboxylase inhibitor.

In another aspect, the present disclosure provides a method of treating cancer in a subject with mutant IDH2 and no homozygous deletion of CDKN2A/B genes, comprising administering to the subject an ornithine decarboxylase inhibitor.

In another aspect, the present disclosure provides a method of treating cancer in a subject with mutant IDH (e.g., IDH1, IDH2) and intact CDKN2A/B genes, comprising administering to the subject an ornithine decarboxylase inhibitor.

In another aspect, the present disclosure provides a method of treating cancer in a subject with mutant IDH1 and intact CDKN2A/B genes, comprising administering to the subject an ornithine decarboxylase inhibitor.

In another aspect, the present disclosure provides a method of treating cancer in a subject with mutant IDH2 and intact CDKN2A/B genes, comprising administering to the subject an ornithine decarboxylase inhibitor.

In another aspect, the present disclosure provides a method of treating cancer in a subject with mutant IDH (e.g., IDH1, IDH2) and no homozygous deletion of CDKN2A/B genes, comprising administering to the subject eflornithine or a salt thereof and a chemotherapeutic agent.

In another aspect, the present disclosure provides a method of treating cancer in a subject with mutant IDH1 and no homozygous deletion of CDKN2A/B genes, comprising administering to the subject eflornithine or a salt thereof and a chemotherapeutic agent.

In another aspect, the present disclosure provides a method of treating cancer in a subject with mutant IDH2 and no homozygous deletion of CDKN2A/B genes, comprising administering to the subject eflornithine or a salt thereof and a chemotherapeutic agent.

In another aspect, the present disclosure provides a method of treating cancer in a subject with mutant IDH (e.g., IDH1, IDH2) and intact CDKN2A/B genes, comprising administering to the subject eflornithine or a salt thereof and a chemotherapeutic agent.

In another aspect, the present disclosure provides a method of treating cancer in a subject with mutant IDH1 and intact CDKN2A/B genes, comprising administering to the subject eflornithine or a salt thereof and a chemotherapeutic agent.

In another aspect, the present disclosure provides a method of treating cancer in a subject with mutant IDH2 and intact CDKN2A/B genes, comprising administering to the subject eflornithine or a salt thereof and a chemotherapeutic agent.

In another aspect, the present disclosure provides a method of treating cancer, comprising selecting a subject with no homozygous deletion of CDKN2A/B genes, and administering to said subject an ornithine decarboxylase inhibitor.

In another aspect, the present disclosure provides a method of treating cancer, comprising selecting a subject with intact CDKN2A/B genes, and administering to said subject an ornithine decarboxylase inhibitor.

In another aspect, the present disclosure provides a method of treating cancer, comprising selecting a subject with mutant IDH (e.g., IDH1, IDH2) and no homozygous deletion of CDKN2A/B genes, and administering to said subject an ornithine decarboxylase inhibitor.

In another aspect, the present disclosure provides a method of treating cancer, comprising selecting a subject with mutant IDH1 and no homozygous deletion of CDKN2A/B genes, and administering to said subject an ornithine decarboxylase inhibitor.

In another aspect, the present disclosure provides a method of treating cancer, comprising selecting a subject with mutant IDH2 and no homozygous deletion of CDKN2A/B genes, and administering to said subject an ornithine decarboxylase inhibitor.

In another aspect, the present disclosure provides a method of treating cancer, comprising selecting a subject with mutant IDH (e.g., IDH1, IDH2) and intact CDKN2A/B genes, and administering to said subject an ornithine decarboxylase inhibitor.

In another aspect, the present disclosure provides a method of treating cancer, comprising selecting a subject with mutant IDH1 and intact CDKN2A/B genes, and administering to said subject an ornithine decarboxylase inhibitor.

In another aspect, the present disclosure provides a method of treating cancer, comprising selecting a subject with mutant IDH2 and intact CDKN2A/B genes, and administering to said subject an ornithine decarboxylase inhibitor.

In another aspect, the present disclosure provides a method of treating cancer, comprising selecting a subject with mutant IDH (e.g., IDH1, IDH2) and no homozygous deletion of CDKN2A/B genes, and administering to said subject eflornithine or a salt thereof and a chemotherapeutic agent.

In another aspect, the present disclosure provides a method of treating cancer, comprising selecting a subject with mutant IDH1 and no homozygous deletion of CDKN2A/B genes, and administering to said subject eflornithine or a salt thereof and a chemotherapeutic agent.

In another aspect, the present disclosure provides a method of treating cancer, comprising selecting a subject with mutant IDH2 and no homozygous deletion of CDKN2A/B genes, and administering to said subject eflornithine or a salt thereof and a chemotherapeutic agent.

In another aspect, the present disclosure provides a method of treating cancer, comprising selecting a subject with mutant IDH (e.g., IDH1, IDH2) and intact CDKN2A/B genes, and administering to said subject eflornithine or a salt thereof and a chemotherapeutic agent.

In another aspect, the present disclosure provides a method of treating cancer, comprising selecting a subject with mutant IDH1 and intact CDKN2A/B genes, and administering to said subject eflornithine or a salt thereof and a chemotherapeutic agent.

In another aspect, the present disclosure provides a method of treating cancer, comprising selecting a subject with mutant IDH2 and intact CDKN2A/B genes, and administering to said subject eflornithine or a salt thereof and a chemotherapeutic agent.

In another aspect, the present disclosure provides a method of treating cancer, comprising:
(1) evaluating CDKN2A/B genetic profiles of a plurality of subjects suffering from cancer;
(2) selecting a subject who has no homozygous deletion of CDKN2A/B genes; and
(3) administering to said subject an ornithine decarboxylase inhibitor, e.g., eflornithine or a salt thereof.

In another aspect, the present disclosure provides a method of treating cancer, comprising:
(1) evaluating IDH (e.g., IDH1, IDH2) genetic profiles of a plurality of subjects suffering from cancer;
(2) evaluating CDKN2A/B genetic profiles of a plurality of subjects suffering from cancer;

(3) selecting a subject who is IDH (e.g., IDH1, IDH2) mutant and has no homozygous deletion of CDKN2A/B genes; and (4) administering to said subject an ornithine decarboxylase inhibitor, e.g., eflornithine or a salt thereof and a chemotherapeutic agent, e.g., lomustine.

In another aspect, the present disclosure provides a method of treating cancer, comprising:

(1) evaluating IDH1 genetic profiles of a plurality of subjects suffering from cancer;

(2) evaluating CDKN2A/B genetic profiles of a plurality of subjects suffering from cancer;

(3) selecting a subject who is IDH1 mutant and has no homozygous deletion of CDKN2A/B genes; and (4) administering to said subject an ornithine decarboxylase inhibitor, e.g., eflornithine or a salt thereof and a chemotherapeutic agent, e.g., lomustine.

In another aspect, the present disclosure provides a method of treating cancer, comprising:

(1) evaluating IDH2 genetic profiles of a plurality of subjects suffering from cancer;

(2) evaluating CDKN2A/B genetic profiles of a plurality of subjects suffering from cancer;

(3) selecting a subject who is IDH2 mutant and has no homozygous deletion of CDKN2A/B genes; and (4) administering to said subject an ornithine decarboxylase inhibitor, e.g., eflornithine or a salt thereof and a chemotherapeutic agent, e.g., lomustine.

In another aspect, the present disclosure provides a method of treating cancer, comprising:

(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:
  the pouch of solid eflornithine, e.g., eflornithine hydrochloride hydrate, wherein
  the pouch comprises:
    an individual dosage of eflornithine, e.g., eflornithine hydrochloride hydrate, and a pharmaceutically acceptable excipient; and
  the instructions to prepare an oral solution of eflornithine, e.g., eflornithine hydrochloride hydrate; and (2) administering to a subject with the cancer characterized by mutant IDH (e.g., IDH1, IDH2) and no homozygous deletion of CDKN2A/B genes the oral solution of eflornithine, e.g., eflornithine hydrochloride hydrate, and a chemotherapeutic agent, e.g., lomustine.

In another aspect, the present disclosure provides a method of treating cancer, comprising:

(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:
  the pouch of solid eflornithine, e.g., eflornithine hydrochloride hydrate, wherein
  the pouch comprises:
    an individual dosage of eflornithine, e.g., eflornithine hydrochloride hydrate, and a pharmaceutically acceptable excipient; and
  the instructions to prepare an oral solution of eflornithine, e.g., eflornithine hydrochloride hydrate; and (2) administering to a subject with the cancer characterized by mutant IDH1 and no homozygous deletion of CDKN2A/B genes the oral solution of eflornithine,
e.g., eflornithine hydrochloride hydrate, and a chemotherapeutic agent, e.g., lomustine.

In another aspect, the present disclosure provides a method of treating cancer, comprising:

(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:
  the pouch of solid eflornithine, e.g., eflornithine hydrochloride hydrate, wherein
  the pouch comprises:
    an individual dosage of eflornithine, e.g., eflornithine hydrochloride hydrate, and a pharmaceutically acceptable excipient; and
  the instructions to prepare an oral solution of eflornithine, e.g., eflornithine hydrochloride hydrate; and (2) administering to a subject with the cancer characterized by mutant IDH2 and no homozygous deletion of CDKN2A/B genes the oral solution of eflornithine, e.g., eflornithine hydrochloride hydrate, and a chemotherapeutic agent, e.g., lomustine.

In another aspect, the present disclosure provides a method that provides improved overall survival (OS) in a cancer subject having mutant IDH (e.g., IDH1, IDH2) and no homozygous deletion of CDKN2A/B genes compared to a cancer subject having mutant IDH1 and homozygous deletion of CDKN2A/B genes.

In another aspect, the present disclosure provides a method that provides improved overall survival (OS) in a cancer subject having mutant IDH1 and no homozygous deletion of CDKN2A/B genes compared to a cancer subject having mutant IDH1 and homozygous deletion of CDKN2A/B genes.

In another aspect, the present disclosure provides a method that provides improved overall survival (OS) in a cancer subject having mutant IDH2 and no homozygous deletion of CDKN2A/B genes compared to a cancer subject having mutant IDH2 and homozygous deletion of CDKN2A/B genes.

In another aspect, the present disclosure provides a method that provides improved overall survival (OS) in a cancer subject having mutant IDH (e.g., IDH1, IDH2) and intact CDKN2A/B genes compared to a cancer subject having mutant IDH (e.g., IDH1, IDH2) and homozygous deletion of CDKN2A/B genes.

In another aspect, the present disclosure provides a method that provides improved overall survival (OS) in a cancer subject having mutant IDH1 and intact CDKN2A/B genes compared to a cancer subject having mutant IDH1 and homozygous deletion of CDKN2A/B genes.

In another aspect, the present disclosure provides a method that provides improved overall survival (OS) in a cancer subject having mutant IDH2 and intact CDKN2A/B genes compared to a cancer subject having mutant IDH2 and homozygous deletion of CDKN2A/B genes.

In another aspect, the present disclosure provides a method that provides improved progression free survival (PFS) in a cancer subject having mutant IDH (e.g., IDH1, IDH2) and no homozygous deletion of CDKN2A/B genes compared to a cancer subject having mutant IDH (e.g., IDH1, IDH2) and homozygous deletion of CDKN2A/B genes.

In another aspect, the present disclosure provides a method that provides improved progression free survival (PFS) in a cancer subject having mutant IDH1 and no homozygous deletion of CDKN2A/B genes compared to a cancer subject having mutant IDH1 and homozygous deletion of CDKN2A/B genes.

In another aspect, the present disclosure provides a method that provides improved progression free survival (PFS) in a cancer subject having mutant IDH2 and no homozygous deletion of CDKN2A/B genes compared to a cancer subject having mutant IDH2 and homozygous deletion of CDKN2A/B genes.

In another aspect, the present disclosure provides a method that provides improved progression free survival (PFS) in a cancer subject having mutant IDH (e.g., IDH1, IDH2) and intact CDKN2A/B genes compared to a cancer subject having mutant IDH (e.g., IDH1, IDH2) and homozygous deletion of CDKN2A/B genes.

In another aspect, the present disclosure provides a method that provides improved progression free survival (PFS) in a cancer subject having mutant IDH1 and intact CDKN2A/B genes compared to a cancer subject having mutant IDH1 and homozygous deletion of CDKN2A/B genes.

In another aspect, the present disclosure provides a method that provides improved progression free survival (PFS) in a cancer subject having mutant IDH2 and intact CDKN2A/B genes compared to a cancer subject having mutant IDH2 and homozygous deletion of CDKN2A/B genes.

In another aspect, the present disclosure provides a method that provides improved overall survival (OS) in a cancer subject having mutant IDH1 (e.g., IDH1, IDH2) gene compared to a cancer subject having wildtype IDH (e.g., IDH1, IDH2) gene.

In another aspect, the present disclosure provides a method that provides improved overall survival (OS) in a cancer subject having mutant IDH1 gene compared to a cancer subject having wildtype IDH1 gene.

In another aspect, the present disclosure provides a method that provides improved overall survival (OS) in a cancer subject having mutant IDH2 gene compared to a cancer subject having wildtype IDH2 gene.

In another aspect, the present disclosure provides a method that provides improved progression free survival (PFS) in a cancer subject having mutant IDH (e.g., IDH1, IDH2) gene compared to a cancer subject having wildtype IDH (e.g., IDH1, IDH2) gene.

In another aspect, the present disclosure provides a method that provides improved progression free survival (PFS) in a cancer subject having mutant IDH1 gene compared to a cancer subject having wildtype IDH1 gene.

In another aspect, the present disclosure provides a method that provides improved progression free survival (PFS) in a cancer subject having mutant IDH2 gene compared to a cancer subject having wildtype IDH2 gene.

In another aspect, the present disclosure provides a method of treating cancer, comprising selecting a subject with mutant IDH (e.g., IDH1, IDH2) and no homozygous deletion of CDKN2A/B genes, and administering to said subject eflornithine or a salt thereof and lomustine.

In some embodiments, the present disclosure provides a method of treating cancer, comprising selecting a subject with mutant IDH (e.g., IDH1, IDH2) and intact CDKN2A/B genes, and administering to said subject eflornithine or a salt thereof and lomustine.

In another aspect, the present disclosure provides a method of treating cancer, comprising selecting a subject with mutant IDH1 and no homozygous deletion of CDKN2A/B genes, and administering to said subject eflornithine or a salt thereof and lomustine. In some embodiments, the present disclosure provides a method of treating cancer, comprising selecting a subject with mutant IDH1 and intact CDKN2A/B genes, and administering to said subject eflornithine or a salt thereof and lomustine.

In another aspect, the present disclosure provides a method of treating cancer, comprising selecting a subject with mutant IDH2 and no homozygous deletion of CDKN2A/B genes, and administering to said subject eflornithine or a salt thereof and lomustine. In some embodiments, the present disclosure provides a method of treating cancer, comprising selecting a subject with mutant IDH2 and intact CDKN2A/B genes, and administering to said subject eflornithine or a salt thereof and lomustine.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1A and FIG. 1B show plasma concentrations for D- and L-eflornithine on Days 1 and 14, respectively.

DETAILED DESCRIPTION

Definitions

Figure 1A:
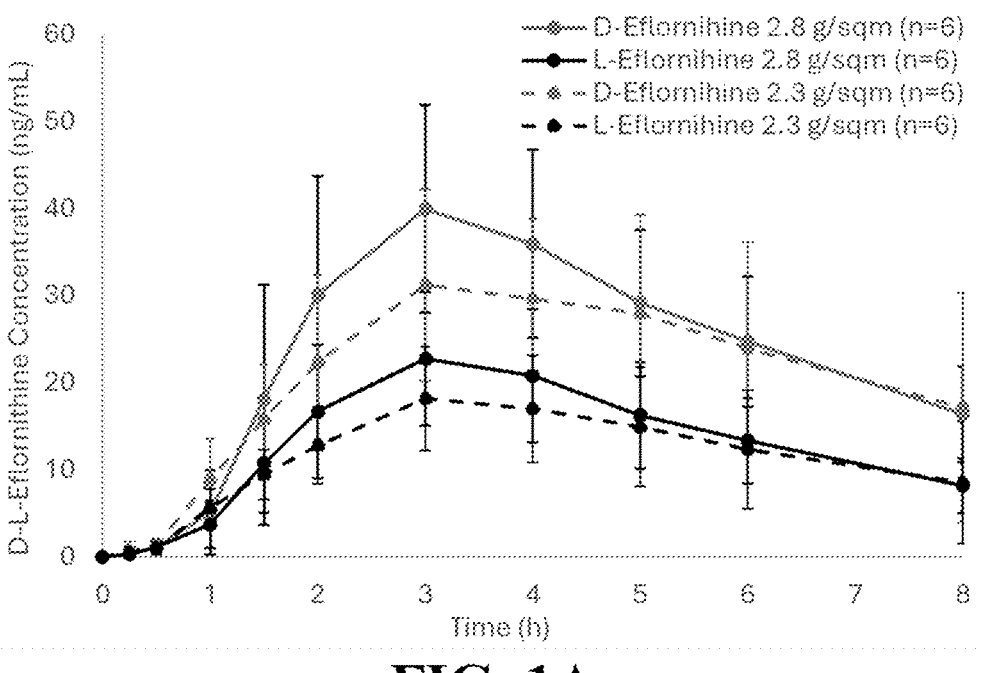
FIG. 1A and FIG. 1B show clinical pharmacokinetic data following oral administration of eflornithine (n=6; doses 2.3 and 2.8 $g/m^2$).

Unless defined otherwise, all technical and scientific terms used herein have the same meaning as is commonly understood by one of skill in the art to which this invention belongs.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. In some embodiments, "about" refers to a range of up to 10% of a given value. In some embodiments, "about" refers to a range of up to 5% of a given value. Alternatively, particularly with respect to biological systems or processes, the term can mean within an order of magnitude, within 5-fold, or within 2-fold, of a value.

Reference in the specification to "some embodiments," "an embodiment," "certain embodiment" or "other embodiments" means that a particular feature, structure, or characteristic described in connection with the embodiments is included in at least some embodiments, but not necessarily all embodiments, of the present disclosure.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target. In some embodiments, "modulate" means to interact with a target either directly or indirectly so as to decrease or inhibit receptor activity. In some embodiments. modulation is an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

The term "modulator" as used herein, refers to a molecule that interacts with a target either directly or indirectly. The interactions include, but are not limited to, the interactions of an agonist, partial agonist, an inverse agonist, antagonist, or combinations thereof. In some embodiments, a modulator is an antagonist. Receptor antagonists are inhibitors of receptor activity. Antagonists mimic ligands that bind to a receptor and prevent receptor activation by a natural ligand. Preventing activation may have many effects. If a natural agonist binding to a receptor leads to an increase in cellular function, an antagonist that binds and blocks this receptor decreases the function of the receptor.

The term "agonism," as used herein, generally refers to the activation of a receptor or enzyme by a modulator, or agonist, to produce a biological response.

The term "agonist," as used herein, generally refers to a modulator that binds to a receptor or enzyme and activates the receptor to produce a biological response. By way of example only, a "$5HT_{2A}$ agonist" can be used to refer to a compound that exhibits an $EC_{50}$ with respect to $5HT_{2A}$ activity of no more than about 100 μM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

The term "antagonism," as used herein, generally refers to the inactivation of a receptor or enzyme by a modulator, or antagonist. Antagonism of a receptor, for example, is when a molecule binds to the receptor and blocks function of the receptor.

The term "antagonist" or "neutral antagonist," as used herein, generally refers to a modulator that binds to a receptor or enzyme and blocks a biological response. An antagonist may have no activity in the absence of an agonist or inverse agonist but can block the activity of either, causing no change in the biological response.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject," "individual," or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating," or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "pharmaceutically acceptable," as used herein, generally refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

A "pharmaceutically acceptable salt" suitable for the disclosure may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent. As used herein, In some embodiments, a salt is a pharmaceutically acceptable salt.

The phrase "pharmaceutically acceptable excipient" or "pharmaceutically acceptable carrier" as used herein means a pharmaceutically acceptable material, composition, or vehicle, such as a liquid or solid filler, diluent, excipient, solvent, or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the term "Adverse Event" (AE), is any untoward medical occurrence in a clinical study patient administered a medicinal product, which does not necessarily have a causal relationship with the treatment. An AE can therefore be any unfavorable and/or unintended sign, symptom, or disease temporally associated with the use of a medicinal product, whether or not considered related to the medicinal product. AEs may also include pre- or post-treatment complications that occur as a result of protocol specified procedures, lack of efficacy, overdose, drug abuse/misuse reports, or occupational exposure. Preexisting events that increase in severity or change in nature during or as a consequence of participation in the clinical study will also be considered AEs. An AE does not include the following: (1) Medical or surgical procedures such as non-CNS tumor surgery, endoscopy, tooth extraction, and transfusion. The condition that led to the procedure may be an adverse event and must be reported; (2) Pre-existing diseases, conditions, or laboratory abnormalities present or detected before the screening visit that do not worsen; (3) Situations where an untoward medical occurrence has not occurred (e.g., hospitalization for elective surgery, social and/or convenience admissions); (4) Overdose without clinical sequelae; or (5) Any medical condition or clinically significant laboratory abnormality with an onset date before the consent form is signed and not related to a protocol-associated procedure is not an AE. It is considered to be pre-existing and should be documented on the medical history eCRF. The severity of AEs will be graded using the CTCAE, Version 4.03. If a CTCAE criterion does not exist, the Investigator will use the grade or adjectives: grade 1 (Mild), grade 2 (Moderate), grade 3 (Severe), grade 4 (Life-threatening), or grade 5 (Fatal) to describe the maximum intensity of the adverse event.

As used herein, the term "Serious Adverse Event" (SAE), is defined as an event that, at any dose, results in the following: (1) Death; (2) Life-threatening (Note: The term "life-threatening" in the definition of "serious" refers to an event in which the patient was at risk of death at the time of the event; it does not refer to an event that hypothetically might have caused death if it were more severe.); (3) In-patient hospitalization or prolongation of existing hospitalization; (4) Persistent or significant disability/incapacity; (5) A congenital anomaly/birth defect; or (6) A medically important event or reaction: such events may not be immediately life-threatening or result in death or hospitalization but may jeopardize the patient or may require intervention to prevent one of the other outcomes constituting SAEs. Medical and scientific judgment must be exercised to determine whether such an event is a reportable under expedited reporting rules. Examples of medically important events include intensive treatment in an emergency room or at home for allergic bronchospasm; blood dyscrasias or convulsions that do not result in hospitalization; and development of drug dependency or drug abuse. For the avoidance of doubt, infections resulting from contaminated medicinal product will be considered a medically important event and subject to expedited reporting requirements.

Therapeutic Applications

CDKN2A/B and IDH (e.g., IDH1, IDH2) Genes

Cyclin Dependent Kinase Inhibitor 2A (CDKN2A) and Cyclin Dependent Kinase Inhibitor 2B (CDKN2B) genes reside on the short arm of chromosome 9 and are commonly expressed in many tissues and cell types. CDKN2A/B encode multiple proteins which are critical in cell-cycle regulation. The deletion of either CDKN2A/B or mutation of either CDKN2A/B is associated with various cancers, e.g., gliomas. The deletions of CDKN2A/B can occur in either a homozygous or heterozygous manner. Homozygous deletions refer to the loss of both copies of a gene (i.e., both alleles) in a cell. Heterozygous deletions refer to the loss of a single copy of a gene (i.e., one allele) while the other copy remains intact in a cell. Typically, homozygous deletions lead to complete loss of function, whereas heterozygous deletions lead to partial loss of function.

Isocitrate Dehydrogenase 1 (IDH1) gene is one of three isocitrate dehydrogenase isozymes (the other being IDH2 and IDH3). IDH1 encodes an enzyme that catalyzes the reversible oxidative decarboxylation of isocitrate as part of the citric acid cycle where the enzyme generates an oncometabolite (i.e., 2-hydroxyglutarate) that affects cellular metabolism and redox homeostasis.

Isocitrate Dehydrogenase 2 (IDH2) gene provides instructions for making an enzyme called isocitrate dehydrogenase 2. This enzyme is found in mitochondria, which are the energy-producing centers within cells. Within mitochondria, the enzyme participates in reactions that produce energy for cell activities. Specifically, isocitrate dehydrogenase 2 normally converts isocitrate to 2-ketoglutarate. A series of additional enzymes further process 2-ketoglutarate to produce energy. The conversion reaction also produces NADPH, which is necessary for many cellular processes and helps protect cells from potentially harmful molecules called reactive oxygen species. In some embodiments, a mutant IDH is a mutant IDH1. In some embodiments, a mutant IDH is a mutant IDH2.

In some embodiments, a subject as described herein comprises mutant IDH1 (e.g., IDH1, IDH2) and no homozygous deletion of CDKN2A/B genes. In some embodiments, a subject as described herein comprises mutant IDH1 and no homozygous deletion of CDKN2A/B genes. In some embodiments, a subject as described herein comprises mutant IDH2 and no homozygous deletion of CDKN2A/B genes. In some embodiments, a subject as described herein comprises mutant IDH (e.g., IDH1, IDH2) and intact CDKN2A/B genes. In some embodiments, a subject as described herein comprises mutant IDH1 and intact CDKN2A/B genes. In some embodiments, a subject as described herein comprises mutant IDH2 and intact CDKN2A/B genes. In some embodiments, a subject as described herein comprises mutant IDH1 (e.g., IDH1, IDH2), no homozygous deletion of CDKN2A/B, and intact ATRX genes. In some embodiments, a subject as described herein comprises mutant IDH1, no homozygous deletion of CDKN2A/B, and intact ATRX genes. In some embodiments, a subject as described herein comprises mutant IDH2, no homozygous deletion of CDKN2A/B, and intact ATRX genes. In some embodiments, a subject as described herein comprises mutant IDH (e.g., IDH1, IDH2), intact CDKN2A/B, and intact ATRX genes. In some embodiments, a subject as described herein comprises mutant IDH1, intact CDKN2A/B, and intact ATRX genes. In some embodiments, a subject as described herein comprises mutant IDH2, intact CDKN2A/B, and intact ATRX genes.

Among other things, the present disclosure provides an insight that a population of cancer subjects with no homozygous deletion of CDKN2A/B genes responds more favorably to a cancer treatment compared to a population with homozygous deletion of CDKN2A/B. Among other things, the present disclosure provides an insight that a population of cancer subjects with mutant IDH (e.g., IDH1, IDH2) and no homozygous deletion of CDKN2A/B genes responds more favorably to a cancer treatment compared to a population with homozygous deletion of CDKN2A/B and/or IDH (e.g., IDH1, IDH2) wild type. In some embodiments, the present disclosure encompasses a finding that a cancer subject with certain genetic profiles as described herein (e.g., mutant IDH (e.g., IDH1, IDH2), no homozygous deletion of CDKN2A/B, intact ATRX, etc., or combinations thereof) responds more favorably to an ornithine decarboxylase inhibitor than a cancer subject with, e.g., one or more of the following: wild type IDH (e.g., IDH1, ID-12), homozygous deletion of CDKN2A/B and mutant ATRX. In some embodiments, an ornithine decarboxylase inhibitor is eflornithine or a salt thereof. In some embodiments, a more favorable response is demonstrated by an improved overall survival (OS). In some embodiments, a more favorable response is demonstrated by an improved progression free survival (PFS).

In one aspect, the present disclosure provides a method of treating cancer in a subject with no homozygous deletion of CDKN2A/B genes, comprising administering to the subject an ornithine decarboxylase inhibitor. In one aspect, the present disclosure provides a method of treating cancer in a subject with intact CDKN2A/B genes, comprising administering to the subject an ornithine decarboxylase inhibitor. In one aspect, the present disclosure provides a method of treating cancer in a subject with mutant IDH (e.g., IDH1, IDH2) and no homozygous deletion of CDKN2A/B genes, comprising administering to the subject an ornithine decarboxylase inhibitor. In one aspect, the present disclosure provides a method of treating cancer in a subject with mutant IDH1 (e.g., IDH1, IDH2) and intact CDKN2A/B genes, comprising administering to the subject an ornithine decarboxylase inhibitor. In some embodiments, a provided method further comprises administering a second therapeutic agent or treatment including, e.g., a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine, or a salt thereof where applicable. In some embodiments, alkylating agent is lomustine, carmustine, or semustine. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

In one aspect, the present disclosure provides a method of treating cancer in a subject with mutant IDH1 (e.g., IDH1, IDH2) and no homozygous deletion of CDKN2A/B genes, comprising administering to the subject eflornithine or a salt thereof and a chemotherapeutic agent.

In another aspect, the present disclosure provides a method of treating a cancer characterized by mutant IDH (e.g., IDH1, IDH2) and no homozygous deletion of CDKN2A/B genes, comprising administering to a subject eflornithine or a salt thereof and lomustine.

In another aspect, the present disclosure provides a method of treating cancer in a subject with mutant IDH (e.g., IDH1, IDH2) and intact CDKN2A/B genes, comprising administering to the subject eflornithine or a salt thereof and a chemotherapeutic agent.

In one aspect, the present disclosure provides a method of treating cancer, comprising selecting a subject with no homozygous deletion of CDKN2A/B genes, and administering to said subject an ornithine decarboxylase inhibitor. In one aspect, the present disclosure provides method of treating cancer, comprising selecting a subject with intact CDKN2A/B genes, and administering to said subject an ornithine decarboxylase inhibitor. In one aspect, the present disclosure provides a method of treating cancer, comprising selecting a subject with mutant IDH1 (e.g., IDH1, IDH2) and no homozygous deletion of CDKN2A/B genes, and administering to said subject an ornithine decarboxylase inhibitor. In one aspect, the present disclosure provides a method of treating cancer, comprising selecting a subject with mutant IDH (e.g., IDH1, IDH2) and intact CDKN2A/B genes, and administering to said subject an ornithine decarboxylase inhibitor. In some embodiments, a provided method further comprises administering a second therapeutic agent or treatment including a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine. In some embodiments, alkylating agent is lomustine, carmustine, or semustine, or a salt thereof where applicable. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

Immunotherapy agents are known in the art and as appreciated by those skilled in the art, various immunotherapy agents can be used in accordance with the present disclosure. In some embodiments, an immunotherapy agent includes the following: (1) IL-15 (T-cell growth factor); (2) Anti-Programmed Death-1 (PD1) and/or anti-B7-H1 (PD1 ligand) (T-cell checkpoint blockade inhibitor); (3) IL-12 (vaccine adjuvant); (4) CD40 and/or CD40L (antigen presenting cell stimulator); (5) IL-7 (T-cell growth factor); (6) CpG (vaccine adjuvant); (7) 1-methyltryptophan (enzyme inhibitor); (8) Anti-CD137 (anti-4-1BB) (T-cell stimulator); (9) Anti-TGF-I3 (signaling inhibitor); (10) Anti-IL-10 Receptor or Anti-IL10 (suppression inhibitor; IL-10 is a suppressor cytokine); (11) FIt3L (dendritic cell growth factor/vaccine adjuvant); (12) Anti-Glucocorticoid-Induced TNF Receptor (GITR) (T-cell stimulator); (13) CCL21 Adenovirus (T-cell attracting chemokine); (14) Monophosphoryl Lipid A (MPL) (vaccine adjuvant); (15) Poly I:C and/or Poly ICLC (vaccine adjuvant); (16) Anti-0X40 (T-cell stimulator); (17) Anti-B7-II4 (T-cell checkpoint blockade inhibitor); (18) Resiquimod and/or 852A (vaccine adjuvant) (19) LIGHT and/or LIGHT vector (T-cell stimulator); (20) Anti-Lymphocyte Activation Gene-3 (LAG-3) (T-cell checkpoint blockade inhibitor); (21) Anti-CTLA4 (T-cell checkpoint blockade inhibitor).

In another aspect, the present disclosure provides a method of treating cancer, comprising selecting a subject with mutant IDH (e.g., IDH1, IDH2) and no homozygous deletion of CDKN2A/B genes, and administering to said subject eflornithine or a salt thereof and a chemotherapeutic agent.

In another aspect, the present disclosure provides a method of treating cancer, comprising selecting a subject with mutant IDH (e.g., IDH1, IDH2) and intact CDKN2A/B genes, and administering to said subject eflornithine or a salt thereof and a chemotherapeutic agent.

In another aspect, the present disclosure provides a method of treating cancer, comprising:

(1) evaluating CDKN2A/B genetic profiles of a plurality of subjects suffering from cancer;

(2) selecting a subject who has no homozygous deletion of CDKN2A/B genes; and (3) administering to said subject an omithine decarboxylase inhibitor, e.g., eflornithine or a salt thereof.

In another aspect, the present disclosure provides a method of treating cancer, comprising:

(1) evaluating CDKN2A/B genetic profiles of a plurality of subjects suffering from cancer;

(2) selecting a subject who has no homozygous deletion of CDKN2A/B genes; and (3) administering to said subject an ornithine decarboxylase inhibitor, e.g., eflornithine or a salt thereof and a chemotherapeutic agent, e.g., lomustine.

In another aspect, the present disclosure provides a method of treating cancer, comprising:

(1) evaluating IDH (e.g., IDH1, IDH2) genetic profiles of a plurality of subjects suffering from cancer;

(2) evaluating CDKN2A/B genetic profiles of a plurality of subjects suffering from cancer;

(3) selecting a subject who is IDH1 (e.g., IDH1, IDH2) mutant and has no homozygous deletion of CDKN2A/B genes; and (4) administering to said subject an ornithine decarboxylase inhibitor, e.g., eflornithine or a salt thereof.

In another aspect, the present disclosure provides a method of treating cancer, comprising:

(1) evaluating IDH (e.g., IDH1, IDH2) genetic profiles of a plurality of subjects suffering from cancer;

(2) evaluating CDKN2A/B genetic profiles of a plurality of subjects suffering from cancer;

(3) selecting a subject who is IDH (e.g., IDH1, IDH2) mutant and has no homozygous deletion of CDKN2A/B genes; and (4) administering to said subject an ornithine decarboxylase inhibitor, e.g., eflornithine or a salt thereof and a chemotherapeutic agent, e.g., lomustine.

In another aspect, the present disclosure provides a method of treating cancer, comprising:

(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:

the pouch of solid eflornithine, e.g., eflornithine hydrochloride hydrate, wherein the pouch comprises:

an individual dosage of eflornithine, e.g., eflornithine hydrochloride hydrate, and a pharmaceutically acceptable excipient; and the instructions to prepare an oral solution of eflornithine, e.g., eflornithine hydrochloride hydrate; and (2) administering to a subject with the cancer characterized by mutant IDH (e.g., IDH1, IDH2) and no homozygous deletion of CDKN2A/B genes the oral solution of eflornithine, e.g., eflornithine hydrochloride hydrate and a chemotherapeutic agent, e.g., lomustine.

In another aspect, the present disclosure provides a method that provides improved overall survival (OS) in a cancer subject having mutant IDH (e.g., IDH1, IDH2) and no homozygous deletion of CDKN2A/B genes compared to a cancer subject having mutant IDH (e.g., IDH1, IDH2) and homozygous deletion of CDKN2A/B genes.

In another aspect, the present disclosure provides a method that provides improved overall survival (OS) in a cancer subject having mutant IDH (e.g., IDH1, IDH2) and intact CDKN2A/B genes compared to a cancer subject having mutant IDH (e.g., IDH1, IDH2) and homozygous deletion of CDKN2A/B genes.

In another aspect, the present disclosure provides a method that provides improved progression free survival (PFS) in a cancer subject having mutant IDH1 (e.g., IDH1, IDH2) and no homozygous deletion of CDKN2A/B genes compared to a cancer subject having mutant IDH (e.g., IDH1, IDH2) and homozygous deletion of CDKN2A/B genes.

In another aspect, the present disclosure provides a method that provides improved progression free survival (PFS) in a cancer subject having mutant IDH1 (e.g., IDH1, IDH2) and intact CDKN2A/B genes compared to a cancer subject having mutant IDH1 (e.g., IDH1, IDH2) and homozygous deletion of CDKN2A/B genes.

In another aspect, the present disclosure provides a method that provides improved overall survival (OS) in a cancer subject having mutant IDH (e.g., IDH1, IDH2) gene compared to a cancer subject having wildtype IDH1 (e.g., IDH11, IDH2) gene.

In another aspect, the present disclosure provides a method that provides improved progression free survival (PFS) in a cancer subject having mutant IDH (e.g., IDH1, IDH2) gene compared to a cancer subject having wildtype IDH (e.g., IDH1, IDH2) gene.

In another aspect, the present disclosure provides a method of treating cancer, comprising selecting a subject with mutant IDH (e.g., IDH1, IDH2) and no homozygous deletion of CDKN2A/B genes, and administering to said subject eflornithine or a salt thereof and lomustine. In some embodiments, the present disclosure provides a method of treating cancer, comprising selecting a subject with mutant IDH (e.g., IDH1, IDH2) and intact CDKN2A/B genes, and administering to said subject eflornithine or a salt thereof and lomustine.

Among other things, the present disclosure provides various methods of treating cancers, e.g., those described above. As used herein, a provided method is referred to as a "Method of the Disclosure."

Among other things, the present disclosure provides a method of treating cancer characterized by certain genetic profiles as described herein. In some embodiments, the present disclosure encompasses an insight that methods of treating cancers described herein provide improved treatment outcome in subject populations with certain genetic profiles compared to subject populations without such genetic profiles. In some embodiments, treatment outcome is improved in subject populations with certain IDH (e.g., IDH1, IDH2) and/or CDKN2A/B profiles. In some embodiments, treatment outcome is improved in subject populations with mutant IDH (e.g., IDH1, IDH2) and no homozygous deletion of CDKN2A/B genes. In some embodiments, treatment outcome is improved in subject populations with mutant IDH (e.g., IDH1l, IDH2) and no mutation of CDKN2A/B genes. In some embodiments, a cancer is a brain cancer. In some embodiments, a cancer is glioma. In some embodiments, a cancer is astrocytoma. In some embodiments, improvement of treatment outcome is statistically significant.

In some embodiments, for a Method of the Disclosure, the subject has mutant IDH (e.g., IDH1, IDH2) gene. In some embodiments, for a Method of the Disclosure, the subject has mutant IDH1 gene. In some embodiments, for a Method of the Disclosure, the subject has mutant IDH2 gene. In some embodiments, a subject has wildtype IDH (e.g., IDH1, IDH2) gene. In some embodiments, a subject has wildtype IDH1 gene. In some embodiments, a subject has wildtype IDH2 gene.

In some embodiments, for a Method of the Disclosure, the subject has intact CDKN2A/B genes. In some embodiments, the subject has heterozygous deletion of CDKN2A/B genes. In some embodiments, the subject has no homozygous deletion of CDKN2A/B genes. In some embodiments, the subject has intact CDKN2A gene. In some embodiments, the subject has heterozygous deletion of CDKN2A gene. In some embodiments, the subject has no homozygous deletion of CDKN2A gene. In some embodiments, the subject has intact CDKN2B gene. In some embodiments, the subject has heterozygous deletion of CDKN2B gene. In some embodiments, the subject has no homozygous deletion of CDKN2B gene.

In some embodiments, for a Method of the Disclosure, the subject has mutant IDH (e.g., IDH1, IDH2) and no homozygous deletion of CDKN2A/B genes. In some embodiments, the subject has mutant IDH (e.g., IDH1, IDH2) and heterozygous deletion of CDKN2A/B genes. In some embodiments, the subject has mutant IDH (e.g., IDH1, IDH2) and intact CDKN2A/B genes. In some embodiments, the subject has mutant IDH1 (e.g., IDH1, IDH2) and no homozygous deletion of CDKN2A gene. In some embodiments, the subject has mutant IDH1 (e.g., IDH1, IDH2) and heterozygous deletion of CDKN2A gene. In some embodiments, the subject has mutant IDH (e.g., IDH1, IDH2) and intact CDKN2A gene. In some embodiments, the subject has mutant IDH (e.g., IDH1, IDH2) and no homozygous deletion of CDKN2B gene. In some embodiments, the subject has mutant IDH1 (e.g., IDH1, IDH2) and heterozygous deletion of CDKN2B gene. In some embodiments, the subject has mutant IDH (e.g., IDH1, IDH2) and intact CDKN2B gene.

In some embodiments, for a Method of the Disclosure, the subject has wildtype IDH (e.g., IDH1, IDH2) and no homozygous deletion of CDKN2A/B genes. In some embodiments, the subject has wildtype IDH (e.g., IDH1, IDH2) and heterozygous deletion of CDKN2A/B genes.

In some embodiments, the subject has wildtype IDH (e.g., IDH1, IDH2) and intact CDKN2A/B genes. In some embodiments, the subject has wildtype IDH (e.g., IDH1, IDH2) and no homozygous deletion of CDKN2A gene. In some embodiments, the subject has wildtype IDH (e.g., IDH1, IDH2) and heterozygous deletion of CDKN2A gene. In some embodiments, the subject has wildtype IDH (e.g., IDH1, IDH2) and intact CDKN2A gene. In some embodiments, the subject has wildtype IDH (e.g., IDH1, IDH2) and no homozygous deletion of CDKN2B gene. In some embodiments, the subject has wildtype IDH1 (e.g., IDH1, IDH2) and heterozygous deletion of CDKN2B gene. In some embodiments, the subject has wildtype IDH (e.g., IDH1, IDH2) and intact CDKN2B gene.

In some embodiments, a mutant IDH1 gene comprises a mutation at R132X or R100Q codon of the IDH1 gene. In some embodiments, a mutation in the IDH1 gene results in the replacement of arginine residue at site 132 with histidine (H), lysine (K) or cysteine (C). As used herein, a mutation in the IDH1 gene which results in the replacement of arginine residue with another amino acid is referred to as "a mutation at R132." In some embodiments, a mutant IDH1 gene comprises a base pair exchange of guanine to adenine (G395A), resulting in an arginine to histidine mutation at site 132 (R132H).

In some embodiments, a mutant IDH2 gene comprises a mutation at R140X or R172X of IDH2 gene.

In some embodiments, for a Method of the Disclosure, the evaluation of IDH1 (e.g., IDH1, IDH2) genetic profiles comprises determining the presence of a mutation in the IDH (e.g., IDH1, IDH2). In some embodiments, the evaluation of IDH (e.g., IDH1, IDH2) genetic profiles comprises determining the presence of a mutation in the IDH1 (e.g., IDH1, IDH2) gene by examining tumor tissue. In some embodiments, the evaluation of IDH (e.g., IDH1, IDH2) genetic profiles comprises determining the presence of a mutation in the IDH (e.g., IDH1, IDH2) gene by examining stained tumor tissue on a microscope slide using immunohistochemistry (IHC) technique or gene sequencing, or other methods known in the art. In some embodiments, the evaluation of IDH (e.g., IDH1, IDH2) genetic profiles comprises determining the presence of a mutation in the IDH (e.g., IDH1, IDH2) gene by examining stained tumor tissue on a microscope slide using immunohistochemistry (IHC) technique. In some embodiments, the evaluation of IDH (e.g., IDH1, IDH2) genetic profiles comprises determining the presence of a mutation in the IDH (e.g., IDH1, IDH2) gene by using gene sequencing. In some embodiments, the evaluation of IDH (e.g., IDH1, IDH2) genetic profiles comprises determining the presence of a mutation at R132 in the IDH1 gene by examining stained tumor tissue on a microscope slide using immunohistochemistry (IHC) technique or gene sequencing. In some embodiments, the evaluation of IDH1 genetic profiles comprises determining the presence of a mutation at R132 in the IDH1 gene by examining stained tumor tissue on a microscope slide using immunohistochemistry (IHC) technique. In some embodiments, the evaluation of IDH1 genetic profiles comprises determining the presence of a mutation at R132 in the IDH1 gene by using gene sequencing. In some embodiments, the gene sequencing is PCR.

In some embodiments, for a Method of the Disclosure, the status of CDKN2A/B is determined by assessing percentage of tumor cells that show intact CDKN2A/B alleles, homozygous deletion of both CDKN2A/B alleles, and heterozygous deletion of CDKN2A/B alleles. In some embodiments, for a Method of the Disclosure, the evaluation of CDKN2A/B genetic profiles comprises determining the percentage of tumor cells that show intact CDKN2A/B alleles, homozygous deletion of both CDKN2A/B alleles, and heterozygous deletion of CDKN2A/B alleles. In some embodiments, the evaluation of CDKN2A/B genetic profiles comprises determining the percentage of tumor cells that show intact CDKN2A/B alleles, homozygous deletion of both CDKN2A/B alleles, and heterozygous deletion of CDKN2A/B alleles, by examining stained tumor tissue on a microscope slide using fluorescence in situ hybridization (FISH) technique. In some embodiments, a subject whose sample shows less than about 25% homozygous deletion of CDKN2A/B in a FISH experiment is evaluated as a subject with no loss of homozygosity of CDKN2A/B genes. In some embodiments, a subject whose sample shows less than about 24% homozygous deletion of CDKN2A/B in a FISH experiment is evaluated as a subject with no deletion of homozygosity of CDKN2A/B genes. In some embodiments, a subject whose sample shows less than about 23% homozygous deletion of CDKN2A/B in a FISH experiment is evaluated as a subject with no deletion of homozygosity of CDKN2A/B genes. In some embodiments, a subject whose sample shows less than about 22% homozygous deletion of CDKN2A/B in a FISH experiment is evaluated as a subject with no deletion of homozygosity of CDKN2A/B genes. In some embodiments, a subject whose sample shows less than about 21% homozygous deletion of CDKN2A/B in a FISH experiment is evaluated as a subject with no deletion of homozygosity of CDKN2A/B genes. In some embodiments, a subject whose sample shows less than about 20% homozygous deletion of CDKN2A/B in a FISH experiment is evaluated as a subject with no deletion of homozygosity of CDKN2A/B genes. In some embodiments, a subject whose sample shows less than about 19% homozygous deletion of CDKN2A/B in a FISH experiment is evaluated as a subject with no deletion of homozygosity of CDKN2A/B genes. In some embodiments, a subject whose sample shows less than about 18% homozygous deletion of CDKN2A/B in a FISH experiment is evaluated as a subject with no deletion of homozygosity of CDKN2A/B genes. In some embodiments, a subject whose sample shows less than about 17% homozygous deletion of CDKN2A/B in a FISH experiment is evaluated as a subject with no deletion of homozygosity of CDKN2A/B genes.

In some embodiments, for a Method of the Disclosure, an evaluation of genetic profile of a subject comprises determining the presence of one or more mutations in one gene. In some embodiments, for a Method of the Disclosure, an evaluation of genetic profile of a subject comprises determining the presence of one or more mutations in more than one gene. In some embodiments, for a Method of the Disclosure, an evaluation of genetic profile of a subject comprises determining status of mutations in IDH (e.g., IDH1, IDH2) gene. In some embodiments, for a Method of the Disclosure, an evaluation of genetic profile of a subject comprises determining status of mutations in CDKN2A/B genes. In some embodiments, for a Method of the Disclosure, an evaluation of genetic profile of a subject comprises determining status of mutations in IDH (e.g., IDH1, IDH2) and CDKN2A/B genes. In some embodiments, for a Method of the Disclosure, an evaluation of genetic profile of a subject comprises determining status of mutations in IDH (e.g., IDH1, IDH2), CDKN2A/B, and ATRX genes.

WHO Grade 3 Astrocytoma

Astrocytomas are brain tumors originating from astrocytes. Astrocytes are glial cells located in the brain and spinal cord, although more commonly found in the brain. Astrocytomas are a subset of gliomas, which are tumors arising from glial cells (not limited to the brain or spinal cord). Prior to 2021, astrocytomas were categorized by their malignancy and behavior from grade I to grade IV, wherein grade IV was considered the most aggressive and deadly astrocytoma. This approach employed histological evidence to classify astrocytomas and was primarily based on features observed underneath a microscope. However, this histological approach was lacking accuracy in guiding treatment and in 2021 the WHO transitioned from solely a histological approach to one that heavily incorporates molecular information, i.e., biomarkers. This paradigm shift in tumor classification— integrating histological features and biomarkers—intends to provide more accurate diagnoses, prognosis, and guide treatment decisions, allowing for more precise patient management. For example, patients having mutant IDH1 (e.g., IDH1, IDH2) and intact CDKN2A/B are categorized as grade 2 or grade 3 astrocytoma. Patients having mutant IDH (e.g., IDH1, IDH2) and homozygous deletion of CDKN2A/B are categorized as grade 4 astrocytoma.

The recent re-classification of gliomas by WHO in 2021 highlights the genetic profile of grade 3 astrocytoma with particular molecular biomarkers, namely IDH1 (e.g., IDH1, IDH2) mutation in combination with no homozygous deletion of CDKN2A/B. In some embodiments, a grade 3 astrocytoma comprises mutant IDH1 and no homozygous deletion of CDKN2A/B genes. In some embodiments, a grade 3 astrocytoma comprises mutant IDH1 and intact CDKN2A/B genes. In some embodiments, a grade 3 astrocytoma comprises mutant IDH2 and no homozygous deletion of CDKN2A/B genes. In some embodiments, a grade 3 astrocytoma comprises mutant IDH2 and intact CDKN2A/B genes. As used herein, the grade classification of astrocytoma e.g., grade 3 astrocytoma, grade 2 astrocytoma, etc., refers to the WHO 2021 classification unless indicated otherwise.

Cytotoxic chemotherapy is reported to be used in treating astrocytoma. Most astrocytomas respond to cytotoxic chemotherapy to a variable extent. However, the use of cytotoxic chemotherapy can face significant challenges in the field of brain cancers, e.g., astrocytoma, due to blood-brain-barrier and blood-tumor barrier. As such, many drugs tested over the years have failed to produce meaningful antitumor efficacy, because they were unable to reach invading tumor cells in sufficient dose and for sufficient time.

Additionally, existing treatments such as chemotherapy and radiotherapy, while offering some hope for patients with advanced astrocytoma, are often plagued with grave side effects/toxicity issues compared to the moderate benefits it can bring. For example, temozolomide (TMZ) is an alkylating agent that has demonstrated clinical antitumor activity against gliomas, including some astrocytomas. The side effects/toxicity issues regarding temozolomide include, but are not limited to, nausea, thrombocytopenia, leukopenia, neutropenia, and anemia. Furthermore, temozolomide can produce lymphopenia and lymphopenia has been associated with the emergence of *Pneumocystis jirovecii* pneumonia (PCP). Prophylaxis against PCP is required for all patients receiving concomitant TMZ and radiotherapy. Lomustine is another small-molecule chemotherapeutic agent commonly used for the treatment of brain tumors. The side effects/toxicity issues regarding lomustine include, but are not limited to, myelosuppression, thrombocytopenia, leukopenia, anemia, reversible hepatotoxicity, nephrotoxicity, nausea and vomiting. The outlook for patients whose astrocytoma recurs or relapses after chemotherapy and radiotherapy is even bleaker. As is appreciated by those skilled in the art, there have been no effective treatment strategies for advanced astrocytoma, especially new treatment strategies for patients with astrocytoma that progress/recur after irradiation and adjuvant chemotherapy with a cytotoxic agent such as, but not limited to, temozolomide.

Among other things, the present disclosure encompasses a discovery of methods for treating astrocytoma that were previously considered untreatable. In some embodiments, the present disclosure provides a method of treating astrocytoma characterized by certain genetic profiles as described herein. Without wishing to be bound by any particular theory, the present disclosure encompasses a finding that methods of treating astrocytoma as described herein provide improved treatment outcome in subject populations with certain genetic profiles compared to subject populations without such genetic profiles. In some embodiments, an astrocytoma is grade 3 astrocytoma. In some embodiments, for a Method of the Disclosure, the subject has grade 3 astrocytoma.

ATRX Gene

Alpha Thalassemia/Mental Retardation Syndrome X-linked (ATRX) gene encodes a protein (i.e., Transcriptional regulator ARTX) that is involved in chromatin remodeling, telomere maintenance, and DNA repair. As such, ATRX gene play an important role in maintaining the genomic stability of humans.

Among other things, contrary to existing studies that suggest the loss of expression of ATRX leads to more favorable prognosis in cancer subjects, e.g., Leeper et al. Oncotarget. 2015 Oct. 6; 6(30):30295-305, the present disclosure encompasses an unexpected finding that subject populations with intact ATRX gene demonstrate improved treatment outcome in a method of treating cancer as described herein.

In some embodiments, for a Method of the Disclosure, the subject has no loss of ATRX gene expression. In some embodiments, the subject has intact ATRX gene. In some embodiments, the subject has mutant ATRX gene. In some embodiments, the subject has wildtype ATRX gene.

In some embodiments, for a Method of the Disclosure, the subject has mutant IDH (e.g., IDH1, IDH2) gene. In some embodiments, a subject has wildtype IDH (e.g., IDH1, IDH2) gene. In some embodiments, for a Method of the Disclosure, the subject has intact CDKN2A/B genes. In some embodiments, the subject has heterozygous deletion of CDKN2A/B genes and intact ATRX. In some embodiments, the subject has no homozygous deletion of CDKN2A/B genes and intact ATRX. In some embodiments, the subject has intact CDKN2A gene and intact ATRX. In some embodiments, the subject has heterozygous deletion of CDKN2A gene and intact ATRX. In some embodiments, the subject has no homozygous deletion of CDKN2A gene and intact ATRX. In some embodiments, the subject has intact CDKN2B gene and intact ATRX. In some embodiments, the subject has heterozygous deletion of CDKN2B gene and intact ATRX. In some embodiments, the subject has no homozygous deletion of CDKN2B gene and intact ATRX.

In some embodiments, for a Method of the Disclosure, the subject has mutant IDH (e.g., IDH1, IDH2), intact ATRX, and no homozygous deletion of CDKN2A/B genes. In some embodiments, the subject has mutant IDH (e.g., IDH1, IDH2), intact ATRX, and heterozygous deletion of CDKN2A/B genes. In some embodiments, the subject has mutant IDH (e.g., IDH1, IDH2), intact ATRX, and intact CDKN2A/B genes. In some embodiments, the subject has mutant IDH (e.g., IDH1, IDH2), intact ATRX, and no homozygous deletion of CDKN2A gene. In some embodiments, the subject has mutant IDH (e.g., IDH1, IDH2), intact ATRX, and heterozygous deletion of CDKN2A gene. In some embodiments, the subject has mutant IDH (e.g., IDH1, IDH2), intact ATRX, and intact CDKN2A gene. In some embodiments, the subject has mutant IDH (e.g., IDH1, IDH2), intact ATRX, and no homozygous deletion of CDKN2B gene. In some embodiments, the subject has mutant IDH (e.g., IDH1, IDH2), intact ATRX, and heterozygous deletion of CDKN2B gene. In some embodiments, the subject has mutant IDH (e.g., IDH1, IDH2), intact ATRX, and intact CDKN2B gene.

In some embodiments, for a Method of the Disclosure, the subject has wildtype IDH (e.g., IDH1, IDH2), intact ATRX, and no homozygous deletion of CDKN2A/B genes. In some embodiments, the subject has wildtype IDH (e.g., IDH1, IDH2), intact ATRX and heterozygous deletion of CDKN2A/B genes. In some embodiments, the subject has wildtype IDH (e.g., IDH1, IDH2), intact ATRX, and intact CDKN2A/B genes. In some embodiments, the subject has wildtype IDH (e.g., IDH1, IDH2), intact ATRX, and no homozygous deletion of CDKN2A gene. In some embodiments, the subject has wildtype IDH (e.g., IDH1, IDH2), intact ATRX, and heterozygous deletion of CDKN2A gene. In some embodiments, the subject has wildtype IDH (e.g., IDH1, IDH2), intact ATRX, and intact CDKN2A gene. In some embodiments, the subject has wildtype IDH (e.g., IDH1, IDH2), intact ATRX, and no homozygous deletion of CDKN2B gene. In some embodiments, the subject has wildtype IDH (e.g., IDH1, IDH2), intact ATRX, and heterozygous deletion of CDKN2B gene. In some embodiments, the subject has wildtype IDH (e.g., IDH1, IDH2), intact ATRX, and intact CDKN2B gene.

In some embodiments, the present disclosure provides a method of treating cancer in a subject with mutant IDH (e.g., IDH1, IDH2), intact ATRX, and no homozygous deletion of CDKN2A/B genes, comprising administering to the subject an ornithine decarboxylase inhibitor. In some embodiments, a provided method further comprises administering a second therapeutic agent or treatment including a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine, or a salt thereof where applicable. In some embodiments, alkylating agent is lomustine, carmustine, or semustine. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

In some embodiments, the present disclosure provides a method of treating cancer in a subject with mutant IDH (e.g., IDH1, IDH2), intact ATRX, and no homozygous deletion of CDKN2A/B genes, comprising administering to the subject eflornithine or a salt thereof and a chemotherapeutic agent. In some embodiments, the method of treating a cancer characterized by mutant IDH (e.g., IDH1, IDH2), intact ATRX, and no homozygous deletion of CDKN2A/B genes, comprises administering to a subject eflornithine or a salt thereof and lomustine.

In some embodiments, the present disclosure provides a method of treating cancer in a subject with mutant IDH (e.g., IDH1, IDH2), intact ATRX, and intact CDKN2A/B genes, comprising administering to the subject an ornithine decarboxylase inhibitor. In some embodiments, a provided method further comprises administering a second therapeutic agent or treatment including a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine, or a salt thereof where applicable. In some embodiments, alkylating agent is lomustine, carmustine, or semustine. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

In some embodiments, the present disclosure provides a method of treating cancer in a subject with mutant IDH (e.g., IDH1, IDH2), intact ATRX, and intact CDKN2A/B genes, comprising administering to the subject eflornithine or a salt thereof and a chemotherapeutic agent. In some embodiments, a method of treating cancer in a subject with mutant IDH1 (e.g., IDH1, IDH2), intact ATRX, and intact CDKN2A/B genes, comprises administering to the subject eflornithine or a salt thereof and lomustine.

In some embodiments, the present disclosure provides a method of treating cancer, comprising selecting a subject with mutant IDH1 (e.g., IDH1, IDH2), intact ATRX, and no homozygous deletion of CDKN2A/B genes, and administering to said subject to the subject an ornithine decarboxylase inhibitor. In some embodiments, a provided method further comprises administering a second therapeutic agent or treatment including a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine, or a salt thereof where applicable. In some embodiments, alkylating agent is lomustine, carmustine, or semustine. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

In some embodiments, the present disclosure provides a method of treating cancer, comprising selecting a subject with mutant IDH (e.g., IDH1, IDH2), intact ATRX, and no homozygous deletion of CDKN2A/B genes, and administering to said subject eflornithine or a salt thereof and a chemotherapeutic agent. In some embodiments, the method of treating cancer, comprises selecting a subject with mutant IDH (e.g., IDH1, IDH2), intact ATRX, and no homozygous deletion of CDKN2A/B genes, and administering to said subject eflornithine or a salt thereof and lomustine.

In some embodiments, the present disclosure provides a method of treating cancer, comprising selecting a subject with mutant IDH (e.g., IDH1, IDH2), intact ATRX, and intact CDKN2A/B genes, and administering to said subject to the subject an ornithine decarboxylase inhibitor. In certain embodiments, the subject's tumor is biopsied and sequenced to determine the IDH (e.g., IDH1, IDH2), ATRX, and CDKN2A/B status. In some embodiments, a provided method further comprises administering a second therapeutic agent or treatment including a chemotherapeutic agent, an immunotherapy agent, or radiation therapy, or a combination thereof. In some embodiments, the second therapeutic agent is a chemotherapeutic agent. In some embodiments, chemotherapeutic agent is selected from an alkylating agent. In some embodiments, alkylating agent is altretamine, bendamustine, busulfan, carboplatin, carmustine, chlorambucil, cisplatin, cyclophosphamide, dacarbazine, fotemustine, ifosfamide, lomustine, mechlorethamine, melphalan, nimustine, oxaliplatin, procarbazine, temozolomide, thiotepa, trabectedin, streptozocin or uramustine, or a salt thereof where applicable. In some embodiments, alkylating agent is lomustine, carmustine, or semustine. In some embodiments, alkylating agent is altretamine. In some embodiments, alkylating agent is bendamustine. In some embodiments, alkylating agent is busulfan. In some embodiments, alkylating agent is carboplatin. In some embodiments, alkylating agent is carmustine. In some embodiments, alkylating agent is chlorambucil. In some embodiments, alkylating agent is cisplatin. In some embodiments, alkylating agent is cyclophosphamide. In some embodiments, alkylating agent is dacarbazine. In some embodiments, alkylating agent is fotemustine. In some embodiments, alkylating agent is ifosfamide. In some embodiments, alkylating agent is lomustine. In some embodiments, alkylating agent is mechlorethamine. In some embodiments, alkylating agent is melphalan. In some embodiments, alkylating agent is nimustine. In some embodiments, alkylating agent is oxaliplatin. In some embodiments, alkylating agent is procarbazine. In some embodiments, alkylating agent is temozolomide. In some embodiments, alkylating agent is thiotepa. In some embodiments, alkylating agent is trabectedin. In some embodiments, alkylating agent is streptozocin. In some embodiments, alkylating agent is uramustine. In some embodiments, the second therapeutic agent is immunotherapy agent. In some embodiments, a provided method further comprises radiation therapy.

In some embodiments, the present disclosure provides a method of treating cancer, comprising selecting a subject with mutant IDH (e.g., IDH1, IDH2), intact ATRX, and intact CDKN2A/B genes, and administering to said subject eflornithine or a salt thereof and a chemotherapeutic agent. In some embodiments, the method of treating cancer, comprises selecting a subject with mutant IDH (e.g., IDH1, IDH2), intact ATRX, and intact CDKN2A/B genes, and administering to said subject eflornithine or a salt thereof and lomustine.

In some embodiments, the present disclosure provides a method of treating cancer, comprising: (1) evaluating CDKN2A/B genetic profiles of a plurality of subjects suffering from cancer; (2) evaluating ARTX genetic profiles of a plurality of subjects suffering from cancer; (3) selecting a subject who has intact ATRX and no homozygous deletion of CDKN2A/B genes; and (4) administering to said subject eflornithine or a salt thereof and a chemotherapeutic agent. In some embodiments, the method of treating cancer, comprises: (1) evaluating CDKN2A/B genetic profiles of a plurality of subjects suffering from cancer; (2) evaluating ARTX genetic profiles of a plurality of subjects suffering from cancer; (3) selecting a subject who has intact ATRX and no homozygous deletion of CDKN2A/B genes; and (4) administering to said subject eflornithine or a salt thereof and lomustine.

In some embodiments, the present disclosure provides a method of treating cancer, comprising: (1) evaluating IDH (e.g., IDH1, IDH2) genetic profiles of a plurality of subjects suffering from cancer; (2) evaluating ARTX genetic profiles of a plurality of subjects suffering from cancer; (3) evaluating CDKN2A/B genetic profiles of a plurality of subjects suffering from cancer; (4) selecting a subject who is IDH (e.g., IDH1, IDH2) mutant, has intact ATRX, and has no homozygous deletion of CDKN2A/B genes; and (5) administering to said subject an ornithine decarboxylase inhibitor. In some embodiments, the present disclosure provides a method of treating cancer, comprising: (1) evaluating IDH1

(e.g., IDH1, IDH2) genetic profiles of a plurality of subjects suffering from cancer; (2) evaluating ARTX genetic profiles of a plurality of subjects suffering from cancer; (3) evaluating CDKN2A/B genetic profiles of a plurality of subjects suffering from cancer; (4) selecting a subject who is IDH (e.g., IDH1, IDH2) mutant, has intact ATRX, and has no homozygous deletion of CDKN2A/B genes; and (5) administering to said subject an ornithine decarboxylase inhibitor and a chemotherapeutic agent. In some embodiments, the present disclosure provides a method of treating cancer, comprising: (1) evaluating IDH (e.g., IDH1, IDH2) genetic profiles of a plurality of subjects suffering from cancer; (2) evaluating ARTX genetic profiles of a plurality of subjects suffering from cancer; (3) evaluating CDKN2A/B genetic profiles of a plurality of subjects suffering from cancer; (4) selecting a subject who is IDH (e.g., IDH1, IDH2) mutant, has intact ATRX, and has no homozygous deletion of CDKN2A/B genes; and (5) administering to said subject eflornithine or a salt thereof and a chemotherapeutic agent. In some embodiments, the method of treating cancer, comprises: (1) evaluating IDH (e.g., IDH1, IDH2) genetic profiles of a plurality of subjects suffering from cancer; (2) evaluating ARTX genetic profiles of a plurality of subjects suffering from cancer; (3) evaluating CDKN2A/B genetic profiles of a plurality of subjects suffering from cancer; (4) selecting a subject who is IDH (e.g., IDH1, IDH2) mutant and has no homozygous deletion of CDKN2A/B genes; and (5) administering to said subject eflornithine or a salt thereof and lomustine.

In some embodiments, the present disclosure provides a method of treating cancer, comprising:

(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:

the pouch of solid eflornithine, e.g., eflornithine hydrochloride hydrate, wherein the pouch comprises:

an individual dosage of eflornithine, e.g., eflornithine hydrochloride hydrate, and a pharmaceutically acceptable excipient; and the instructions to prepare an oral solution of eflornithine, e.g., eflornithine hydrochloride hydrate; and (2) administering to a subject with the cancer characterized by mutant IDH (e.g., IDH1, IDH2), intact ATRX, and no homozygous deletion of CDKN2A/B genes the oral solution of eflornithine, e.g., eflornithine hydrochloride hydrate, and a chemotherapeutic agent, e.g., lomustine.

Recurrent/Refractory Cancer

Recurrent cancer is any form of cancer that returns after a period of remission or after a treatment was thought to have eliminated all detectable cancer cells. Depending on the location of recurrent cancer relative to the original location, the recurrent cancer can be termed local recurrence (i.e., same location as the original tumor), regional recurrence (i.e., in nearby tissues or lymph nodes), or distant/metastatic recurrence (i.e., distant parts of the body). Refractory cancer generally refers to cancer that does not respond to a specific treatment or stops responding to a specific treatment after an initial period of improvement. Although recurrent cancers can be refractory cancers and vice versa, often refractory cancers are considered a subset of recurrent cancers, which are particularly challenging to treat. Some cancers are more prone to being recurrent/refractory, especially brain cancers including, but not limited to, astrocytomas. Furthermore, recurrent/refractory cancers can be classified as a chemotherapy recurrent/refractory cancer, a radiotherapy recurrent/refractory cancer, or a combination thereof. A specific chemotherapy recurrent/refractory cancer is temozolomide recurrent/refractory cancer.

Among other things, the present disclosure provides a discovery of treatment methods for recurrent and or refractory cancer, which would normally be considered untreatable.

In some embodiments, for a Method of the Disclosure, the recurrent and or refractory cancer is characterized by mutant IDH (e.g., IDH1, IDH2) gene. In some embodiments, the recurrent and or refractory cancer is characterized by wildtype IDH (e.g., IDH1, IDH2) gene.

In some embodiments, for a Method of the Disclosure, the recurrent and or refractory cancer is characterized by intact CDKN2A/B genes. In some embodiments, the recurrent and or refractory cancer is characterized by heterozygous deletion of CDKN2A/B genes. In some embodiments, the recurrent and or refractory cancer is characterized by no homozygous deletion of CDKN2A/B genes. In some embodiments, the recurrent and or refractory cancer is characterized by intact CDKN2A gene. In some embodiments, the recurrent and or refractory cancer is characterized by heterozygous deletion of CDKN2A gene. In some embodiments, the recurrent and or refractory cancer is characterized by no homozygous deletion of CDKN2A gene. In some embodiments, the recurrent and or refractory cancer is characterized by intact CDKN2B gene. In some embodiments, the recurrent and or refractory cancer is characterized by heterozygous deletion of CDKN2B gene. In some embodiments, the recurrent and or refractory cancer is characterized by no homozygous deletion of CDKN2B gene.

In some embodiments, for a Method of the Disclosure, the recurrent and or refractory cancer is characterized by mutant IDH1 (e.g., IDH1, IDH2) and no homozygous deletion of CDKN2A/B genes. In some embodiments, the recurrent and or refractory cancer is characterized by mutant IDH (e.g., IDH1, DH2) and heterozygous deletion of CDKN2A/B genes. In some embodiments, the recurrent and or refractory cancer is characterized by mutant IDH (e.g., IDH1, IDH2) and intact CDKN2A/B genes. In some embodiments, the recurrent and or refractory cancer is characterized by mutant IDH (e.g., IDH1, IDH2) and no homozygous deletion of CDKN2A gene. In some embodiments, the recurrent and or refractory cancer is characterized by mutant IDH (e.g., IDH1, IDH2) and heterozygous deletion of CDKN2A gene. In some embodiments, the recurrent and or refractory cancer is characterized by mutant IDH1 (e.g., IDH1, IDH2) and intact CDKN2A gene. In some embodiments, the recurrent and or refractory cancer is characterized by mutant IDH (e.g., IDH1, IDH2) and no homozygous deletion of CDKN2B gene. In some embodiments, the recurrent and or refractory cancer is characterized by mutant IDH (e.g., IDH1, IDH2) and heterozygous deletion of CDKN2B gene. In some embodiments, the recurrent and or refractory cancer is characterized by mutant IDH1 (e.g., IDH1, IDH2) and intact CDKN2B gene.

In some embodiments, for a Method of the Disclosure, the recurrent and or refractory cancer is characterized by intact CDKN2A/B genes. In some embodiments, the recurrent and or refractory cancer is characterized by heterozygous deletion of CDKN2A/B genes and intact ATRX. In some embodiments, the recurrent and or refractory cancer is characterized by no homozygous deletion of CDKN2A/B genes and intact ATRX. In some embodiments, the recurrent and or refractory cancer is characterized by intact CDKN2A gene and intact ATRX. In some embodiments, the recurrent and or refractory cancer is characterized by heterozygous deletion of CDKN2A gene and intact ATRX. In some embodiments, the recurrent and or refractory cancer is characterized by no homozygous deletion of CDKN2A gene and intact ATRX. In some embodiments, the recurrent and or refractory cancer is characterized by intact CDKN2B gene and intact ATRX. In some embodiments, the recurrent and or refractory cancer is characterized by heterozygous deletion of CDKN2B gene and intact ATRX. In some embodiments, the recurrent and or refractory cancer is characterized by no homozygous deletion of CDKN2B gene and intact ATRX.

In some embodiments, for a Method of the Disclosure, the recurrent and or refractory cancer is characterized by mutant IDH (e.g., IDH1, IDH2), intact ATRX, and no homozygous deletion of CDKN2A/B genes. In some embodiments, the recurrent and or refractory cancer is characterized by mutant IDH (e.g., IDH1, IDH2), intact ATRX, and heterozygous deletion of CDKN2A/B genes. In some embodiments, the recurrent and or refractory cancer is characterized by mutant IDH (e.g., IDH1, IDH2), intact ATRX, and intact CDKN2A/B genes. In some embodiments, the recurrent and or refractory cancer is characterized by mutant IDH (e.g., IDH1, IDH2), intact ATRX, and no homozygous deletion of CDKN2A gene. In some embodiments, the recurrent and or refractory cancer is characterized by mutant IDH (e.g., IDH1, IDH2), intact ATRX, and heterozygous deletion of CDKN2A gene. In some embodiments, the recurrent and or refractory cancer is characterized by mutant IDH1 (e.g., IDH1, IDH2), intact ATRX, and intact CDKN2A gene. In some embodiments, the recurrent and or refractory cancer is characterized by mutant IDH (e.g., IDH1, IDH2), intact ATRX, and no homozygous deletion of CDKN2B gene. In some embodiments, the recurrent and or refractory cancer is characterized by mutant IDH (e.g., IDH1, IDH2), intact ATRX, and heterozygous deletion of CDKN2B gene. In some embodiments, the recurrent and or refractory cancer is characterized by mutant IDH (e.g., IDH1, IDH2), intact ATRX, and intact CDKN2B gene.

In some embodiments, for a Method of the Disclosure, the recurrent and or refractory cancer is characterized by wildtype IDH (e.g., IDH1, IDH2), intact ATRX, and no homozygous deletion of CDKN2A/B genes. In some embodiments, the recurrent and or refractory cancer is characterized by wildtype IDH (e.g., IDI-1, IDH2), intact ATRX and heterozygous deletion of CDKN2A/B genes. In some embodiments, the recurrent and or refractory cancer is characterized by wildtype IDH (e.g., IDH1, IDH2), intact ATRX, and intact CDKN2A/B genes. In some embodiments, the recurrent and or refractory cancer is characterized by wildtype IDH (e.g., IDH1, IDH2), intact ATRX, and no homozygous deletion of CDKN2A gene. In some embodiments, the recurrent and or refractory cancer is characterized by wildtype IDH (e.g., IDH1, IDH2), intact ATRX, and heterozygous deletion of CDKN2A gene. In some embodiments, the recurrent and or refractory cancer is characterized by wildtype IDH (e.g., IDH1, IDH2), intact ATRX, and intact CDKN2A gene. In some embodiments, the recurrent and or refractory cancer is characterized by wildtype IDH (e.g., IDH1, IDH2), intact ATRX, and no homozygous deletion of CDKN2B gene. In some embodiments, the recurrent and or refractory cancer is characterized by wildtype IDH (e.g., IDH1, IDH2), intact ATRX, and heterozygous deletion of CDKN2B gene. In some embodiments, the recurrent and or refractory cancer is characterized by wildtype IDH (e.g., IDH1, IDH2), intact ATRX, and intact CDKN2B gene.

In some embodiments, for a Method of the Disclosure, the cancer is radiotherapy recurrent/refractory cancer. In some embodiments, the radiotherapy recurrent/refractory cancer is radiotherapy recurrent/refractory glioma. In some embodiments, the radiotherapy recurrent/refractory cancer is radiotherapy recurrent/refractory grade 2 astrocytoma or radiotherapy recurrent/refractory grade 3 astrocytoma. In some embodiments, the radiotherapy recurrent/refractory cancer is radiotherapy recurrent/refractory grade 2 astrocytoma. In some embodiments, the radiotherapy recurrent/refractory cancer is radiotherapy recurrent/refractory grade 3 astrocytoma. In some embodiments, the subject is a subject who experiences relapse after radiotherapy. In some embodiments, the subject is a glioma subject who experiences relapse after radiotherapy. In some embodiments, the subject is a grade 2 astrocytoma subject who experiences relapse after radiotherapy. In some embodiments, the subject is a grade 3 astrocytoma subject who experiences relapse after radiotherapy.

In some embodiments, for a Method of the Disclosure, the cancer is chemotherapy recurrent/refractory cancer. In some embodiments, the chemotherapy recurrent/refractory cancer is chemotherapy recurrent/refractory glioma. In some embodiments, the chemotherapy recurrent/refractory cancer is chemotherapy recurrent/refractory grade 2 astrocytoma or chemotherapy recurrent/refractory grade 3 astrocytoma. In some embodiments, the chemotherapy recurrent/refractory cancer is chemotherapy recurrent/refractory grade 2 astrocytoma. In some embodiments, the chemotherapy recurrent/refractory cancer is radiotherapy recurrent/refractory grade 3 astrocytoma. In some embodiments, the subject is a subject who experiences relapse after chemotherapy. In some embodiments, the subject is a glioma subject who experiences relapse after chemotherapy. In some embodiments, the subject is a grade 2 astrocytoma subject who experiences relapse after chemotherapy. In some embodiments, the subject is a grade 3 astrocytoma subject who experiences relapse after chemotherapy.

In some embodiments, for a Method of the Disclosure, the cancer is temozolomide recurrent/refractory cancer. In some embodiments, the temozolomide recurrent/refractory cancer is temozolomide recurrent/refractory glioma. In some embodiments, the temozolomide recurrent/refractory cancer is temozolomide recurrent/refractory grade 2 astrocytoma or temozolomide recurrent/refractory grade 3 astrocytoma. In some embodiments, the temozolomide recurrent/refractory cancer is temozolomide recurrent/refractory grade 2 astrocytoma. In some embodiments, the temozolomide recurrent/refractory cancer is temozolomide recurrent/refractory grade 3 astrocytoma. In some embodiments, the subject is a subject who experiences relapse after temozolomide treatment. In some embodiments, the subject is a glioma subject who experiences relapse after temozolomide treatment. In some embodiments, the subject is a grade 2 astrocytoma subject who experiences relapse after temozolomide treatment. In some embodiments, the subject is a grade 3 astrocytoma subject who experiences relapse after temozolomide treatment.

In some embodiments, for a Method of the Disclosure, the cancer is selected from radiotherapy recurrent/refractory cancer, chemotherapy recurrent/refractory cancer, temozolomide recurrent/refractory cancer, glioma, grade 2 astrocytoma, grade 3 astrocytoma, and any combination thereof. In some embodiments, radiotherapy recurrent/refractory glioma, chemotherapy recurrent/refractory glioma, temozolomide recurrent/refractory glioma, radiotherapy recurrent/refractory grade 2 astrocytoma, chemotherapy recurrent/ refractory grade 2 astrocytoma, temozolomide recurrent/refractory grade 2 astrocytoma, radiotherapy recurrent/refractory grade 3 astrocytoma, chemotherapy recurrent/refractory grade 3 astrocytoma, temozolomide recurrent/refractory grade 3 astrocytoma, and any combination thereof. In some embodiments, the cancer is glioma. In some embodiments, the cancer is grade 2 astrocytoma or grade 3 astrocytoma. In some embodiments, the cancer is grade 3 astrocytoma.

Ornithine Decarboxylase Inhibitors

The enzyme ornithine decarboxylase (ODC) is the first and rate limiting enzyme in the biosynthesis of polyamines Among other things, the present disclosure recognizes that polyamines play critical roles in differentiation and proliferation of mammalian cells and are essential for neoplastic transformation, making inhibition of ornithine decarboxylase (ODC) activity an attractive target for a chemotherapeutic agent. Various ornithine decarboxylase inhibitors can be used in accordance with the present disclosure. In some embodiments, ornithine decarboxylase inhibitor is eflornithine, caffeic acid, caffeic acid phenethyl ester, caffeic acid methyl ester, (2S)-(+)-Amino-6-iodoacetamidohexanoic acid, or POB-Calbiochem (N-(4'-Pyridoxyl)-Ornithine (BOC)—OMe), or a salt thereof where applicable. In some embodiments, ornithine decarboxylase inhibitor is eflornithine or a salt thereof. In some embodiments, ornithine decarboxylase inhibitor is eflornithine HCl salt. In some embodiments, ornithine decarboxylase inhibitor is eflornithine monohydrochloride hydrate (eflornithine HCl·H$_2$O). In some embodiments, ornithine decarboxylase inhibitor is caffeic acid. In some embodiments, ornithine decarboxylase inhibitor is caffeic acid phenethyl ester. In some embodiments, ornithine decarboxylase inhibitor is caffeic acid methyl ester. In some embodiments, ornithine decarboxylase inhibitor is (2S)-(+)-Amino-6-iodoacetamidohexanoic acid. In some embodiments, ornithine decarboxylase inhibitor is POB-Calbiochem (N-(4'-Pyridoxyl)-Ornithine(BOC)-OMe).

Eflornithine and Lomustine

As used herein, eflornithine refers to difluoromethylornithine (DFMO). In some embodiments, an active ingredient used according to the present disclosure is eflornithine in its free base form. In some embodiments, an active ingredient used according to the present disclosure is a salt of eflornithine. In some embodiments, the salt of eflornithine is a pharmaceutically acceptable salt of eflornithine. In some embodiments, the pharmaceutically acceptable salt of eflornithine further comprises a pharmaceutically acceptable carrier. In some embodiments, an active ingredient used according to the present disclosure is a hydrate of eflornithine. In some embodiments, an active ingredient used according to the present disclosure is eflornithine monohydrochloride hydrate (eflornithine HCl·H$_2$O). Eflornithine is a potent, enzyme-activated, irreversible inhibitor of the enzyme omithine decarboxylase (ODC), the first and rate limiting enzyme in the biosynthesis of polyamines. Furthermore, eflornithine inhibition of ODC leads to inhibition of tumor cell migration and invasion.

Unless otherwise stated, structures depicted herein (e.g., eflornithine or a salt thereof) are meant to include compounds which differ only in the presence of one or more isotopically enriched atoms. For example, compounds having the present structure except for the replacement of a hydrogen atom by a deuterium or tritium, or the replacement of a carbon atom by a 13C- or 14C-enriched carbon are within the scope of the disclosure.

Certain compounds described herein may exist as enantiomers and all such stereochemical forms of the compounds being within the scope of the disclosure. Unless otherwise stated, structures depicted herein (e.g., eflornithine or a salt thereof) are also meant to include all stereochemical forms of the structure, e.g., the R and S configurations for each asymmetric center, otherwise referred to as L and D configurations for each asymmetric center. Therefore, single stereochemical isomers as well as enantiomeric mixtures of the present compounds are within the scope of the disclosure. In certain embodiments, the present compound is provided in a stereoisomerically enriched form, e.g., one enantiomer is present in a greater amount than another enantiomer. In certain embodiments, the present compound is provided in a racemic form, wherein two enantiomers of such compound are present in about equal amounts.

As used herein, lomustine refers to 1-(2-chloroethyl)-3-cyclohexyl-1-nitrosourea (also referred to as, e.g., CCNU, CccNU®, and Gleostine®).

Among other things, the present disclosure provides an insight that the treatment outcome of a cancer treatment, e.g., overall survival (OS), improves significantly when eflornithine or a salt thereof is administered in combination with lomustine compared to when lomustine is administered alone.

In some embodiments, the present disclosure provides an insight that the treatment outcome of a cancer treatment, e.g., overall survival (OS), improves significantly when eflornithine or a salt thereof is administered in combination with lomustine compared to when lomustine is administered alone in a subject with cancer that progress/recur after irradiation and adjuvant temozolomide chemotherapy.

In some embodiments, the present disclosure provides an insight that the treatment outcome of a cancer treatment, e.g., progression free survival (PFS), improves significantly when eflornithine or a salt thereof is administered in combination with lomustine compared to when lomustine is administered alone.

In some embodiments, the present disclosure provides an insight that the treatment outcome e.g., progression free survival (PFS), improves significantly when eflornithine or a salt thereof is administered in combination with lomustine compared to when lomustine is administered alone in a subject with cancer that progress/recur after irradiation and adjuvant temozolomide chemotherapy.

In some embodiments, the present disclosure provides an insight that the improvement in the treatment outcome of combination of eflornithine or a salt thereof and lomustine compared to lomustine alone is more significant in subject population with certain genetic profiles as described herein. In some embodiments, the certain genetic profiles are charactered by WHO 2021 classification. In some embodiments, certain genetic profiles comprise mutant IDH (e.g., IDH1, IDH2), homozygous deletion of CDKN2A/B genes, no homozygous deletion of CDKN2A/B, heterozygous deletion of CDKN2A/B genes, no heterozygous deletion of CDKN2A/B, intact ATRX gene, mutant ATRX gene, loss of ATRX gene, or any combinations thereof. In some embodiments, the certain genetic profiles comprise mutant IDH (e.g., IDH1, IDH2), no homozygous deletion of CDKN2A/B, no heterozygous deletion of CDKN2A/B, intact ATRX gene, mutant ATRX gene, loss of ATRX gene, or any combinations thereof. In some embodiments, the certain genetic profiles comprise mutant IDH (e.g., IDH1, IDH2), no homozygous deletion of CDKN2A/B, intact ATRX gene, mutant ATRX gene, loss of ATRX gene, or any combinations thereof. In some embodiments, the certain genetic profiles comprise mutant IDH (e.g., IDH1, IDH2), no homozygous deletion of CDKN2A/B, intact ATRX gene, loss of ATRX gene, or any combinations thereof. In some embodiments, the certain genetic profiles comprise mutant IDH (e.g., IDH1, IDH2), no homozygous deletion of CDKN2A/B, intact ATRX gene, or any combinations thereof. In some embodiments, the certain genetic profiles comprise mutant IDH (e.g., IDH1, IDH2), no homozygous deletion of CDKN2A/B, loss of ATRX gene, or any combinations thereof.

In some embodiments, the present disclosure provides a method of treating cancer characterized by a genetic profile as described herein, comprising administering to the subject eflornithine or a salt thereof and a chemotherapeutic agent. In some embodiments, the genetic profile comprises mutant IDH (e.g., IDH1, IDH2), homozygous deletion of CDKN2A/B genes, no homozygous deletion of CDKN2A/B, heterozygous deletion of CDKN2A/B genes, no heterozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, no heterozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, or any combinations thereof. In some embodiments, the genetic profile comprises mutant IDH (e.g., IDH1, IDH2), no homozygous deletion of CDKN2A/B, loss of ATRX gene, or any combinations thereof.

In some embodiments, the present disclosure provides a method of treating cancer characterized by a genetic profile as described herein, comprising administering to a subject eflornithine or a salt thereof and lomustine. In some embodiments, the genetic profile comprises mutant IDH (e.g., IDH1, IDH2), homozygous deletion of CDKN2A/B genes, no homozygous deletion of CDKN2A/B, heterozygous deletion of CDKN2A/B genes, no heterozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, no heterozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, mutant ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, loss of ATRX gene, or any combinations thereof. In some embodiments, the genetic profile comprises mutant IDH (e.g., IDH1, IDH2), no homozygous deletion of CDKN2A/B, intact ATRX gene, or any combinations thereof. In some embodiments, the genetic profile comprises mutant IDH (e.g., IDH1, IDH2), no homozygous deletion of CDKN2A/B, loss of ATRX gene, or any combinations thereof.

In some embodiments, the present disclosure provides a method of treating cancer in a subject with mutant IDH (e.g., IDH1, IDH2) and no homozygous deletion of CDKN2A/B genes, comprising administering to the subject eflornithine or a salt thereof and a chemotherapeutic agent.

In some embodiments, the present disclosure provides a method of treating a cancer characterized by mutant IDH (e.g., IDH1, IDH2) and no homozygous deletion of CDKN2A/B genes, comprising administering to a subject eflornithine or a salt thereof and lomustine.

In some embodiments, the present disclosure provides a method of treating cancer in a subject with mutant IDH (e.g., IDH1, IDH2) and intact CDKN2A/B genes, comprising administering to the subject eflornithine or a salt thereof and a chemotherapeutic agent.

In some embodiments, the present disclosure provides a method of treating cancer, comprising selecting a subject with a genetic profile as described herein, and administering to said subject eflornithine or a salt thereof and lomustine.

In some embodiments, the present disclosure provides a method of treating cancer, comprising selecting a subject with mutant IDH (e.g., IDH1, IDH2) and no homozygous deletion of CDKN2A/B genes, and administering to said subject eflornithine or a salt thereof and a chemotherapeutic agent.

In some embodiments, the present disclosure provides a method of treating cancer, comprising selecting a subject with mutant IDH (e.g., IDH1, IDH2) and intact CDKN2A/B genes, and administering to said subject eflornithine or a salt thereof and a chemotherapeutic agent.

In some embodiments, the present disclosure provides a method of treating cancer, comprising:
(1) evaluating the genetic profiles of a plurality of subjects suffering from cancer;
(2) selecting a subject who has a genetic profile as described herein; and
(3) administering to said subject eflornithine or a salt thereof and a chemotherapeutic agent.

In some embodiments, the present disclosure provides a method of treating cancer, comprising:
(1) evaluating CDKN2A/B genetic profiles of a plurality of subjects suffering from cancer;
(2) selecting a subject who has no homozygous deletion of CDKN2A/B genes; and
(3) administering to said subject an ornithine decarboxylase inhibitor, e.g., eflornithine or a salt thereof.

In some embodiments, the present disclosure provides a method of treating cancer, comprising:
(1) evaluating CDKN2A/B genetic profiles of a plurality of subjects suffering from cancer;
(2) selecting a subject who has no homozygous deletion of CDKN2A/B genes; and
(3) administering to said subject an ornithine decarboxylase inhibitor, e.g., eflornithine or a salt thereof and a chemotherapeutic agent, e.g., lomustine.

In some embodiments, the present disclosure provides a method of treating cancer, comprising:
(1) evaluating IDH (e.g., IDH1, IDH2) genetic profiles of a plurality of subjects suffering from cancer;
(2) evaluating CDKN2A/B genetic profiles of a plurality of subjects suffering from cancer;
(3) selecting a subject who is IDH (e.g., IDH1, IDH2) mutant and has no homozygous deletion of CDKN2A/B genes; and
(4) administering to said subject an ornithine decarboxylase inhibitor, e.g., eflornithine or a salt thereof.

In some embodiments, the present disclosure provides a method of treating cancer, comprising:
(1) evaluating IDH (e.g., IDH1, IDH2) genetic profiles of a plurality of subjects suffering from cancer;
(2) evaluating CDKN2A/B genetic profiles of a plurality of subjects suffering from cancer;
(3) selecting a subject who is IDH (e.g., IDH1, IDH2) mutant and has no homozygous deletion of CDKN2A/B genes; and
(4) administering to said subject an ornithine decarboxylase inhibitor, e.g., eflornithine or a salt thereof and a chemotherapeutic agent, e.g., lomustine.

In certain embodiments, the present disclosure provides a kit comprising a pouch of a solid eflornithine, e.g., eflornithine hydrochloride hydrate, that is suitable for making an oral solution. In some embodiments, a pouch as described herein comprises an individual dosage of eflornithine, e.g., eflornithine hydrochloride hydrate, and a pharmaceutically acceptable excipient; and the instructions to prepare an oral solution of eflornithine, e.g., eflornithine hydrochloride hydrate.

In some embodiments, the present disclosure provides a method of treating cancer, comprising:
(1) preparing an oral solution of eflornithine or a salt thereof comprising: adding the contents of a pouch of solid eflornithine, e.g., eflornithine hydrochloride hydrate, to water according to instructions of a kit to make the oral solution, wherein the kit comprises:
the pouch of solid eflornithine, e.g., eflornithine hydrochloride hydrate, wherein
the pouch comprises:
an individual dosage of eflornithine, e.g., eflornithine hydrochloride hydrate, and a pharmaceutically acceptable excipient; and
the instructions to prepare an oral solution of eflornithine, e.g., eflornithine hydrochloride hydrate; and
(2) administering to a subject with the cancer characterized by mutant IDH (e.g., IDH1, IDH2) and no homozygous deletion of CDKN2A/B genes the oral solution of eflornithine, e.g., eflornithine hydrochloride hydrate, and a chemotherapeutic agent, e.g., lomustine.

In some embodiments, the present disclosure provides a method of treating grade 3 astrocytoma, comprising administering to a subject eflornithine or a salt thereof and a chemotherapeutic agent. In some embodiments, the method comprises administering to a subject eflornithine or a salt thereof and lomustine.

In some embodiments, for a Method of the Disclosure, the chemotherapeutic agent is selected from bendamustine, carmustine, lomustine, procarbazine, vincristine, temozolomide, bevacizumab, regorafenib, vorasidenib, tovorafenib, carboplatin, cisplatin, irinotecan, fotemustine, 5-fluorouracil, doxorubicin, daunorubicin, paclitaxel, etoposide, and floxuridine. In some embodiments, the chemotherapeutic agent is selected from bendamustine, carmustine, lomustine, procarbazine, vincristine, temozolomide, bevacizumab, regorafenib, vorasidenib, tovorafenib, carboplatin, cisplatin, irinotecan, fotemustine, 5-fluorouracil, doxorubicin, and daunorubicin. In some embodiments, the chemotherapeutic agent is selected from bendamustine, carmustine, lomustine, procarbazine, vincristine, temozolomide, bevacizumab, regorafenib, vorasidenib, tovorafenib, carboplatin, cisplatin, and irinotecan. In some embodiments, the chemotherapeutic agent is selected from bendamustine, carmustine, lomustine, procarbazine, vincristine, temozolomide, bevacizumab, regorafenib, vorasidenib, and tovorafenib. In some embodiments, the chemotherapeutic agent is selected from lomustine, procarbazine, vincristine, temozolomide, bevacizumab, regorafenib, vorasidenib, and tovorafenib. In some embodiments, the chemotherapeutic agent is selected from lomustine, temozolomide, bevacizumab, regorafenib, vorasidenib, and tovorafenib. In some embodiments, the chemotherapeutic agent is selected from lomustine, regorafenib, vorasidenib, and tovorafenib. In some embodiments, the chemotherapeutic agent is bendamustine. In some embodiments, the chemotherapeutic agent is carmustine. In some embodiments, the chemotherapeutic agent is procarbazine. In some embodiments, the chemotherapeutic agent is vincristine. In some embodiments, the chemotherapeutic agent is temozolomide. In some embodiments, the chemotherapeutic agent is bevacizumab. In some embodiments, the chemotherapeutic agent is regorafenib. In some embodiments, the chemotherapeutic agent is vorasidenib. In some embodiments, the chemotherapeutic agent is tovorafenib. In some embodiments, the chemotherapeutic agent is carboplatin. In some embodiments, the chemotherapeutic agent is cisplatin. In some embodiments, the chemotherapeutic agent is irinotecan. In some embodiments, the chemotherapeutic agent is fotemustine. In some embodiments, the chemotherapeutic agent is 5-fluorouracil. In some embodiments, the chemotherapeutic agent is doxorubicin. In some embodiments, the chemotherapeutic agent is daunorubicin. In some embodiments, the chemotherapeutic agent is paclitaxel. In some embodiments, the chemotherapeutic agent is etoposide. In some embodiments, the chemotherapeutic agent is floxuridine. In some embodiments, the chemotherapeutic agent is lomustine. In some embodiments, the chemotherapeutic agent is carmustine.

In some embodiments, for a Method of the Disclosure, the subject is administered eflornithine hydrochloride hydrate or eflornithine (free base). In some embodiments, the subject is administered eflornithine hydrochloride hydrate. In some embodiments, the subject is administered eflornithine (free base).

In some embodiments, for a Method of the Disclosure, the method comprises administering a therapeutically effective amount of eflornithine or a salt thereof and a chemotherapeutic agent. In some embodiments, the method comprises administering a therapeutically effective amount of eflornithine or a salt thereof and lomustine. In some embodiments, the method comprises administering a therapeutically effective amount of eflornithine or a salt thereof and a therapeutically effective amount of lomustine.

Described herein are doses of eflornithine or a salt thereof, e.g., eflornithine monohydrochloride hydrate, for administration to subjects in need thereof. Unless otherwise indicated, the doses described herein are calculated based upon the anhydrous and free base weight of the active ingredient of eflornithine or salt thereof. For example, a 2.8 g/m$^2$ dose of eflornithine monohydrochloride hydrate as discussed herein is based on the mass of the eflornithine and does not include the mass of the HCl or water molecule.

In some embodiments, for a Method of the Disclosure, eflornithine is administered at a dose from about 0.5 g/m$^2$ to about 15 g/m$^2$ three-times daily (every 8 hours) free base equivalent. In some embodiments, eflornithine is administered at a dose from about 1 g/m$^2$ to about 10 g/m$^2$ three-times daily (every 8 hours) free base equivalent. In some embodiments, eflornithine is administered at a dose from about 1 g/m$^2$ to about 8 g/m$^2$ three-times daily (every 8 hours) free base equivalent. In some embodiments, eflornithine is administered at a dose from about 1 g/m$^2$ to about 6 g/m$^2$ three-times daily (every 8 hours) free base equivalent. In some embodiments, eflornithine is administered at a dose from about 1 g/m$^2$ to about 3 g/m$^2$ three-times daily (every 8 hours) free base equivalent. In some embodiments, eflornithine is administered at a dose from about 1.2 g/m$^2$ to about 4 g/m$^2$ three-times daily (every 8 hours) free base equivalent. In some embodiments, eflornithine is administered at a dose from about 1.4 g/m$^2$ to about 3.5 g/m$^2$ three-times daily (every 8 hours) free base equivalent. In some embodiments, eflornithine is administered at a dose from about 1.4 g/m$^2$ to about 3.0 g/m$^2$ three-times daily (every 8 hours) free base equivalent. In some embodiments, eflornithine is administered at a dose from about 1.4 g/m$^2$ to about 2.5 g/m$^2$ three-times daily (every 8 hours) free base equivalent. In some embodiments, eflornithine is administered at a dose of about 1.4 g/m$^2$, 2.1 mg/m$^2$, 2.3 g/m$^2$ or 2.8 g/m$^2$ three-times daily (every 8 hours) free base equivalent. In some embodiments, eflornithine is administered at a dose of about 1.4 g/m$^2$, 2.1 mg/m$^2$, or 2.3 g/m$^2$ three-times daily (every 8 hours) free base equivalent. In some embodiments, eflornithine is administered at a dose of about 2.8 g/m$^2$ three-times daily (every 8 hours) free base equivalent. In some embodiments, eflornithine is administered at a dose of about 2.1 g/m$^2$ three-times daily (every 8 hours) free base equivalent. In some embodiments, eflornithine is administered at a dose of about 1.4 g/m$^2$ three-times daily (every 8 hours) free base equivalent. In some embodiments, eflornithine is administered at a dose of about 0.5 g/m$^2$ three-times daily (every 8 hours) free base equivalent. In some embodiments, eflornithine is administered at a dose of about 0.6 g/m$^2$ three-times daily (every 8 hours) free base equivalent. In some embodiments, eflornithine is administered at a dose of about 0.7 g/m$^2$ three-times daily (every 8 hours) free base equivalent. In some embodiments, eflornithine is administered at a dose of about 0.8 g/m$^2$ three-times daily (every 8 hours) free base equivalent. In some embodiments, eflornithine is administered at a dose of about 0.9 g/m$^2$ three-times daily (every 8 hours) free base equivalent. In some embodiments, eflornithine is administered at a dose of about 1 g/m$^2$ three-times daily (every 8 hours) free base equivalent. In some embodiments, eflornithine is administered at a dose of about 1.1 g/m$^2$ three-times daily (every 8 hours) free base equivalent. In some embodiments, eflornithine is administered at a dose of about 1.2 g/m$^2$ three-times daily (every 8 hours) free base equivalent. In some embodiments, eflornithine is administered at a dose of about 1.3 g/m$^2$ three-times daily (every 8 hours) free base equivalent. In some embodiments, eflornithine is administered at a dose of about 1.5 g/m$^2$ three-times daily (every 8 hours) free base equivalent. In some embodiments, eflornithine is administered at a dose of about 1.6 g/m$^2$ three-times daily (every 8 hours) free base equivalent. In some embodiments, eflornithine is administered at a dose of about 1.7 g/m$^2$ three-times daily (every 8 hours) free base equivalent. In some embodiments, eflornithine is administered at a dose of about 1.8 g/m$^2$ three-times daily (every 8 hours) free base equivalent. In some embodiments, eflornithine is administered at a dose of about 1.9 g/m$^2$ three-times daily (every 8 hours) free base equivalent. In some embodiments, eflornithine is administered at a dose of about 2.0 g/m$^2$ three-times daily (every 8 hours) free base equivalent. In some embodiments, eflornithine is administered at a dose of about 2.2 g/m$^2$ three-times daily (every 8 hours) free base equivalent. In some embodiments, eflornithine is administered at a dose of about 2.4 g/m$^2$ three-times daily (every 8 hours) free base equivalent. In some embodiments, eflornithine is administered at a dose of about 2.5 g/m$^2$ three-times daily (every 8 hours) free base equivalent. In some embodiments, eflornithine is administered at a dose of about 2.6 g/m$^2$ three-times daily (every 8 hours) free base equivalent. In some embodiments, eflornithine is administered at a dose of about 2.7 g/m² three-times daily (every 8 hours) free base equivalent. In some embodiments, eflornithine is administered at a dose of about 2.9 g/m² three-times daily (every 8 hours) free base equivalent. In some embodiments, eflornithine is administered at a dose of about 3.0 g/m² three-times daily (every 8 hours) free base equivalent.

In some embodiments, for a Method of the Disclosure, eflornithine or a salt thereof is administered on a schedule. In some embodiments, eflornithine or a salt thereof is administered daily on a two-week-on followed by a one-week-off schedule. In some embodiments, eflornithine or a salt thereof is administered in one or more cycles of treatment period and each cycle comprises about 6 weeks. In some embodiments, eflornithine or a salt thereof is administered in one or more cycles of treatment period and each cycle comprises about 8 weeks. In some embodiments, eflornithine or a salt thereof is administered for at least 1 cycle. In some embodiments, eflornithine or a salt thereof is administered for about 1 cycle to about 24 cycles. In some embodiments, eflornithine or a salt thereof is administered for about 2 cycles to about 24 cycles. In some embodiments, eflornithine or a salt thereof is administered for about 1 cycle to about 8 cycles. In some embodiments, eflornithine or a salt thereof is administered for at least about 3 cycles to about 24 cycles. In some embodiments, eflornithine or a salt thereof is administered for at least about 6 cycles to about 24 cycles. In some embodiments, eflornithine or a salt thereof is administered for at least about 6 cycles to about 21 cycles. In some embodiments, eflornithine or a salt thereof is administered for at least about 6 cycles to about 18 cycles. In some embodiments, eflornithine or a salt thereof is administered for at least about 6 cycles to about 15 cycles. In some embodiments, eflornithine or a salt thereof is administered for at least about 6 cycles to about 12 cycles. In some embodiments, eflornithine or a salt thereof is administered for at least about 6 cycles to about 9 cycles. In some embodiments, eflornithine or a salt thereof is administered for at least about 6 cycles. In some embodiments, eflornithine or a salt thereof is administered for at least about 9 cycles. In some embodiments, eflornithine or a salt thereof is administered for at least about 12 cycles. In some embodiments, eflornithine or a salt thereof is administered for at least about 15 cycles. In some embodiments, eflornithine or a salt thereof is administered for at least about 18 cycles. In some embodiments, eflornithine or a salt thereof is administered for at least about 21 cycles. In some embodiments, eflornithine or a salt thereof is administered for at least about 24 cycles. In some embodiments, eflornithine or a salt thereof is administered for at least about 12 months to about 72 months. In some embodiments, eflornithine or a salt thereof is administered for at least about 12 months to about 60 months. In some embodiments, eflornithine or a salt thereof is administered for at least about 12 months to about 48 months. In some embodiments, eflornithine or a salt thereof is administered for at least about 12 months to about 36 months. In some embodiments, eflornithine or a salt thereof is administered for at least about 12 months to about 24 months. In some embodiments, eflornithine or a salt thereof is administered for at least about 12 months. In some embodiments, eflornithine or a salt thereof is administered for at least about 24 months. In some embodiments, eflornithine or a salt thereof is administered for at least about 36 months. In some embodiments, eflornithine or a salt thereof is administered for at least about 48 months. In some embodiments, eflornithine or a salt thereof is administered for at least about 60 months. In some embodiments, eflornithine or a salt thereof is administered for at least about 72 months.

In some embodiments, for a Method of the Disclosure, the chemotherapeutic agent is lomustine. In some embodiments, lomustine is administered at a dose from about 30 mg/m² to about 110 mg/m². In some embodiments, lomustine is administered at a dose from about 30 mg/m² to about 110 mg/m² every 6 weeks. In some embodiment, lomustine is administered at a dose from about 50 mg/m² to about 110 mg/m². In some embodiment, lomustine is administered at a dose from about 50 mg/m² to about 110 mg/m² every 6 weeks. In some embodiments, lomustine is administered at a dose from about 30 mg/m² to about 90 mg/m² every 6 weeks. In some embodiments, lomustine is administered at a dose from about 30 mg/m² to about 60 mg/m² every 6 weeks. In some embodiments, lomustine is administered at a dose from about 60 mg/m² to about 90 mg/m² every 6 weeks. In some embodiments, lomustine is administered at a dose from about 30 mg/m² to about 90 mg/m². In some embodiments, lomustine is administered at a dose from about 30 mg/m² to about 60 mg/m². In some embodiments, lomustine is administered at a dose from about 60 mg/m² to about 90 mg/m². In some embodiments, lomustine is administered at a dose of from about 50 mg/m² to about 90 mg/m². In some embodiments, lomustine is administered at a dose of from about 50 mg/m² to about 90 mg/m² every 6 weeks. In some embodiments, lomustine is administered at a dose of about 110 mg/m². In some embodiments, lomustine is administered at a dose of about 100 mg/m². In some embodiments, lomustine is administered at a dose of about 90 mg/m². In some embodiments, lomustine is administered at a dose of about 80 mg/m². In some embodiments, lomustine is administered at a dose of about 70 mg/m². In some embodiments, lomustine is administered at a dose of about 60 mg/m². In some embodiments, lomustine is administered at a dose of about 50 mg/m². In some embodiments, lomustine is administered at a dose of about 40 mg/m². In some embodiments, lomustine is administered at a dose of about 30 mg/m². In some embodiments, lomustine is administered at a dose of about 110 mg/m² every 6 weeks. In some embodiments, lomustine is administered at a dose of about 100 mg/m² every 6 weeks. In some embodiments, lomustine is administered at a dose of about 90 mg/m² every 6 weeks. In some embodiments, lomustine is administered at a dose of about 80 mg/m² every 6 weeks. In some embodiments, lomustine is administered at a dose of about 70 mg/m² every 6 weeks. In some embodiments, lomustine is administered at a dose of about 60 mg/m² every 6 weeks. In some embodiments, lomustine is administered at a dose of about 50 mg/m² every 6 weeks. In some embodiments, lomustine is administered at a dose of about 40 mg/m² every 6 weeks. In some embodiments, lomustine is administered at a dose of about 30 mg/m² every 6 weeks. In some embodiments, lomustine is administered at a dose of no more than about 110 mg/m² every 6 weeks. In some embodiments, lomustine is administered at a dose of no more than about 100 mg/m² every 6 weeks. In some embodiments, lomustine is administered at a dose of no more than about 90 mg/m² every 6 weeks. In some embodiments, lomustine is administered at a dose of about 90 mg/m² to about 110 mg/m² every 6 weeks. In some embodiments, lomustine is administered at a dose of about 90 mg/m² to about 100 mg/m² every 6 weeks.

In some embodiments, for a Method of the Disclosure, the chemotherapeutic agent is lomustine. In some embodiments, lomustine is administered in one or more cycles of treatment period and each cycle comprises about 6 weeks. In some embodiments, lomustine is administered in one or more cycles of treatment period and each cycle comprises about 8 weeks. In some embodiments, lomustine is administered for at least 1 cycle. In some embodiments, lomustine is administered for about 1 cycle to about 24 cycles. In some embodiments, lomustine is administered for about 2 cycles to about 24 cycles. In some embodiments, lomustine is administered for about 1 cycle to about 8 cycles. In some embodiments, lomustine is administered for no more than 24 cycles. In some embodiments, lomustine is administered for no more than 21 cycles. In some embodiments, lomustine is administered for no more than 18 cycles. In some embodiments, lomustine is administered for no more than 15 cycles. In some embodiments, lomustine is administered for no more than 12 cycles. In some embodiments, lomustine is administered for no more than 9 cycles. In some embodiments, lomustine is administered for no more than 6 cycles. In some embodiments, lomustine is administered for no more than 3 cycles.

In some embodiments, for a Method of the Disclosure, the chemotherapeutic agent is lomustine. In some embodiments, lomustine is administered for no more than 72 months. In some embodiments, lomustine is administered for no more than 60 months. In some embodiments, lomustine is administered for no more than 48 months. In some embodiments, lomustine is administered for no more than 36 months. In some embodiments, lomustine is administered for no more than 24 months. In some embodiments, lomustine is administered for no more than 12 months. In some embodiments, lomustine is administered for no more than 6 months. In some embodiments, lomustine is administered for no more than 3 months. In some embodiments, lomustine is administered for no more than 2 months. In some embodiments, lomustine is administered for no more than 1 month.

In some embodiments, for a Method of the Disclosure, lomustine is administered on a day wherein eflornithine or a salt thereof is not administered. In some embodiments, lomustine is administered on a day in the off-week of the treatment period of eflornithine or a salt thereof. In some embodiments, eflornithine or a salt thereof is administered daily on Days 1-14 (Weeks 1 and 2) and Days 22-35 (Weeks 4 and 5), and lomustine is administered on Day 15 (+2 days) (Week 3). In some embodiments, dose of lomustine is discontinued after 6 cycles or 12 months, whichever comes first, and eflornithine or a salt thereof is administered for an additional 1, 2, 3, 4, 5, 6, 7, 8, 9, 11, 12, 13, 14, 15, 16, 17, 18, 19, 20, 21, 22, 23, or 24 months after discontinuation of the dose of lomustine. In some embodiments, dose of lomustine is discontinued after 6 cycles or 12 months, whichever comes first, and eflornithine or a salt thereof is administered for an additional 1, 2, 3, 4, 5, 6, 7, 8, 9, 11, 12, 13, 14, 15, 16, 17, 18, 19, or 20 months after discontinuation of the dose of lomustine. In some embodiments, dose of lomustine is discontinued after 6 cycles or 12 months, whichever comes first, and eflornithine or a salt thereof is administered for an additional 1, 2, 3, 4, 5, 6, 7, 8, 9, 11, 12, 13, 14, 15, or 16 months after discontinuation of the dose of lomustine. In some embodiments, dose of lomustine is discontinued after 6 cycles or 12 months, whichever comes first, and eflornithine or a salt thereof is administered for an additional 1, 2, 3, 4, 5, 6, 7, 8, 9, 11, or 12 months after discontinuation of the dose of lomustine. In some embodiments, dose of lomustine is discontinued after 6 cycles or 12 months, whichever comes first, and eflornithine or a salt thereof is administered for an additional 1, 2, 3, 4, 5, 6, 7, or 8 months after discontinuation of the dose of lomustine.

In some embodiments, dose of lomustine is discontinued after 6 cycles or 12 months, whichever comes first, and eflornithine or a salt thereof is administered for an additional 1, 2, 3, or 4 months after discontinuation of the dose of lomustine. In some embodiments, dose of lomustine is discontinued after 6 cycles or 12 months, whichever comes first.

In some embodiments, for a Method of the Disclosure, the method further comprises adjusting or delaying the dose of eflornithine based on observed toxicity according to CTCAE toxicity grade scale. In some embodiments, the subject develops an adverse event of hearing impairment, tinnitus, diarrhea, nausea, or vomiting, or any combination thereof. In some embodiments, the dose of eflornithine is maintained at original dose if hearing impairment grade is 1 or normal under CTCAE toxicity grade scale, and the dose of eflornithine is reduced to 75% of original eflornithine dose if hearing impairment grade is 2 or 3 under CTCAE toxicity grade scale, and the dose of eflornithine is reduced to 50% of original eflornithine dose if hearing impairment grade is 4 under CTCAE toxicity grade scale. In some embodiments, the dose of eflornithine is maintained at 2.8 $g/m^2$ if hearing impairment grade is 1 or normal under CTCAE toxicity grade scale, and the dose of eflornithine is reduced to 2.1 $g/m^2$ if hearing impairment grade is 2 or 3 under CTCAE toxicity grade scale, and the dose of eflornithine is reduced to 1.4 $g/m^2$ if hearing impairment grade is 4 under CTCAE toxicity grade scale.

In some embodiments, for a Method of the Disclosure, the method further comprises adjusting or delaying the dose of eflornithine based on observed toxicity according to CTCAE toxicity grade scale. In some embodiments, the subject develops an adverse event of hearing impairment, tinnitus, diarrhea, nausea, or vomiting, or any combination thereof. In some embodiments, the dose of eflornithine is maintained at original dose if tinnitus grade is 1 or 2 or normal under CTCAE toxicity grade scale, and the dose of eflornithine is reduced to 75% of original eflornithine dose if tinnitus grade is 3 under CTCAE toxicity grade scale. In some embodiments, the dose of eflornithine is maintained at 2.8 $g/m^2$ if tinnitus grade is 1 or 2 or normal under CTCAE toxicity grade scale, and the dose of eflornithine is reduced to 2.1 $g/m^2$ if tinnitus grade is 3 under CTCAE toxicity grade scale.

In some embodiments, for a Method of the Disclosure, the method further comprises adjusting or delaying the dose of eflornithine based on observed toxicity according to CTCAE toxicity grade scale. In some embodiments, the subject develops an adverse event of hearing impairment, tinnitus, diarrhea, nausea, or vomiting, or any combination thereof. In some embodiments, the dose of eflornithine is maintained at original dose if diarrhea, nausea, or vomiting grade is 1 or 2 or normal under CTCAE toxicity grade scale, and the dose of eflornithine is reduced to 75% of original eflornithine dose if diarrhea, nausea, or vomiting grade is 3 under CTCAE toxicity grade scale, and the dose of eflornithine is reduced to 50% of original eflornithine dose if diarrhea or vomiting grade is 4 under CTCAE toxicity grade scale. In some embodiments, the dose of eflornithine is maintained at 2.8 $g/m^2$ if diarrhea, nausea, or vomiting grade is 1 or 2 or normal under CTCAE toxicity grade scale, and the dose of eflornithine is reduced to 2.1 $g/m^2$ if diarrhea, nausea, or vomiting grade is 3 under CTCAE toxicity grade scale, and the dose of eflornithine is reduced to 1.4 $g/m^2$ if diarrhea or vomiting grade is 4 under CTCAE toxicity grade scale.

Among other things, the present disclosure encompasses an insight that adverse events that commonly come with administration of lomustine due to its toxicity can be mitigated by modifying the dose of lomustine. In some embodiments, the present disclosure discovered that reducing the dose of lomustine to a level lower than the dose of standard of care (e.g., 130 mg/m², 110 mg/²) mitigates adverse events associated with lomustine without affecting the efficiency of the treatment. In some embodiments, for a Method of the Disclosure, the method further comprises adjusting or delaying the dose of lomustine based on observed toxicity according to CTCAE toxicity grade scale. In some embodiments, the dose of lomustine is maintained at original dose if grade is 1 or normal under CTCAE toxicity grade scale, and the dose of lomustine is reduced to 75% of original lomustine dose if grade is 2 under CTCAE toxicity grade scale, and the dose of lomustine is reduced to 50% of original lomustine dose if grade is 3 or 4 under CTCAE toxicity grade scale.

In some embodiments, for a Method of the Disclosure, the method further comprises adjusting or delaying the dose of lomustine for subjects who experienced thrombocytopenia after treatment.

In some embodiments, for a Method of the Disclosure, the method further comprises adjusting the dose of lomustine to 110 mg/m² for subjects who experienced thrombocytopenia after receiving treatment. In some embodiments, the method further comprises adjusting the dose of lomustine to 90 mg/m² for subjects who experienced thrombocytopenia after receiving treatment. In some embodiments, the method further comprises adjusting the dose of lomustine to 60 mg/m² for subjects who experienced thrombocytopenia after receiving treatment. In some embodiments, the method further comprises adjusting the dose of lomustine to 30 mg/m² for subjects who experienced thrombocytopenia after receiving treatment.

In some embodiments, for a Method of the Disclosure, the subject is administered a pharmaceutical composition comprising eflornithine or a salt thereof. In some embodiments, the pharmaceutical composition of eflornithine or salt thereof is formulated as a solution. In some embodiments, the pharmaceutical composition of eflornithine or salt thereof is formulated for oral administration. In some embodiments, the pharmaceutical composition of eflornithine or salt thereof is formulated as a solution for oral administration. In some embodiments, the pharmaceutical composition of eflornithine or salt thereof comprises from about 13.2% to about 22.8% of eflornithine hydrochloride hydrate, water, and one or more pharmaceutically acceptable excipients. In some embodiments, the pharmaceutical composition of eflornithine or salt thereof comprises from about 14.2% to about 21.8% of eflornithine hydrochloride hydrate, water, and one or more pharmaceutically acceptable excipients. In some embodiments, the pharmaceutical composition of eflornithine or salt thereof comprises from about 15.2% to about 20.8% of eflornithine hydrochloride hydrate, water, and one or more pharmaceutically acceptable excipients. In some embodiments, the pharmaceutical composition of eflornithine or salt thereof comprises from about 16.2% to about 19.8% of eflornithine hydrochloride hydrate, water, and one or more pharmaceutically acceptable excipients. In some embodiments, the pharmaceutical composition of eflornithine or salt thereof comprises from about 17.2% to about 18.8% of eflornithine hydrochloride hydrate, water, and one or more pharmaceutically acceptable excipients. In some embodiments, the pharmaceutical composition of eflornithine or salt thereof comprises about 18% of eflornithine hydrochloride hydrate (13.9% eflornithine free base equivalent), glycerin, propylene glycol, saccharin sodium, sodium benzoate, and water. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, powdered tragacanth, malt, gelatin, talc, cocoa butter, peanut oil, cottonseed oil, safflower oil, sesame oil, olive oil, corn oil, soybean oil, propylene glycol, glycerin, sorbitol, polyethylene glycol ethyl oleate, ethyl laurate, agar, magnesium hydroxide, magnesium stearate, aluminum hydroxide, alginic acid, water, pyrogen-free water, isotonic saline, Ringer's solution, ethyl alcohol, and phosphate buffer solutions, or any combination thereof. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, gelatin, talc, cocoa butter, propylene glycol, glycerin, sorbitol, polyethylene glycol ethyl oleate, ethyl laurate, agar, magnesium hydroxide, magnesium stearate, aluminum hydroxide, alginic acid, water, pyrogen-free water, isotonic saline, Ringer's solution, ethyl alcohol, and phosphate buffer solutions, or any combination thereof. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, gelatin, talc, propylene glycol, glycerin, sorbitol, polyethylene glycol ethyl oleate, ethyl laurate, alginic acid, water, and ethyl alcohol, or any combination thereof. In some embodiments, the one or more pharmaceutically acceptable excipients is selected from lactose, glucose, sucrose, mannitol, saccharin sodium, sodium benzoate, cellulose, sodium carboxymethyl cellulose, ethyl cellulose, cellulose acetate, propylene glycol, glycerin, sorbitol, polyethylene glycol ethyl oleate, ethyl laurate, alginic acid, water, and ethyl alcohol, or any combination thereof. In some embodiments, the one or more pharmaceutically acceptable excipients is selected from lactose, glucose, sucrose, mannitol, saccharin sodium, sodium benzoate, propylene glycol, glycerin, sorbitol, polyethylene glycol ethyl oleate, ethyl laurate, alginic acid, water, and ethyl alcohol, or any combination thereof. In some embodiments, the one or more pharmaceutically acceptable excipients is selected from lactose, glucose, sucrose, mannitol, saccharin sodium, sodium benzoate, propylene glycol, glycerin, and water, or any combination thereof. In some embodiments, one or more pharmaceutically acceptable excipients is selected from saccharin sodium, sodium benzoate, propylene glycol, glycerin, and water, or any combination thereof.

In some embodiments, for a Method of the Disclosure, the subject is administered a pharmaceutical composition comprising lomustine. In some embodiments, the subject is administered a pharmaceutical composition comprising lomustine and one or more pharmaceutically acceptable excipients. In some embodiments, the pharmaceutical composition of lomustine is formulated as a capsule. In some embodiments, the pharmaceutical composition of lomustine is formulated for oral administration. In some embodiments, the pharmaceutical composition of lomustine is formulated as a capsule for oral administration. In some embodiments, the pharmaceutical composition of lomustine comprises lomustine and one or more pharmaceutically acceptable excipients. In some embodiments, the pharmaceutical composition of lomustine comprises lomustine, magnesium stearate, and mannitol. In some embodiments, the pharmaceutical composition of lomustine comprises lomustine, magnesium stearate, and mannitol and is formulated as a capsule. In some embodiments, the pharmaceutical composition of lomustine comprises lomustine, magnesium stearate, and mannitol and is formulated as a capsule for oral administration. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, powdered tragacanth, malt, gelatin, talc, cocoa butter, peanut oil, cottonseed oil, safflower oil, sesame oil, olive oil, corn oil, soybean oil, propylene glycol, glycerin, sorbitol, mannitol, polyethylene glycol ethyl oleate, ethyl laurate, agar, magnesium hydroxide, magnesium stearate, aluminum hydroxide, alginic acid, water, pyrogen-free water, isotonic saline, Ringer's solution, ethyl alcohol, and phosphate buffer solutions, or any combination thereof. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, talc, cocoa butter, peanut oil, cottonseed oil, safflower oil, sesame oil, olive oil, corn oil, soybean oil, propylene glycol, glycerin, sorbitol, polyethylene glycol ethyl oleate, ethyl laurate, agar, magnesium hydroxide, magnesium stearate, aluminum hydroxide, alginic acid, and water, or any combination thereof. In some embodiments, the one or more pharmaceutically acceptable excipients is selected from lactose, glucose, sucrose, mannitol, corn starch, potato starch, saccharin sodium, sodium benzoate, cellulose, sodium carboxymethyl cellulose, ethyl cellulose, cellulose acetate, talc, propylene glycol, glycerin, sorbitol, polyethylene glycol ethyl oleate, ethyl laurate, magnesium hydroxide, magnesium stearate, aluminum hydroxide, alginic acid, and water, or any combination thereof. In some embodiments, the one or more pharmaceutically acceptable excipients is selected from lactose, glucose, sucrose, mannitol, saccharin sodium, sodium benzoate, cellulose, sodium carboxymethyl cellulose, ethyl cellulose, cellulose acetate, talc, propylene glycol, glycerin, sorbitol, magnesium hydroxide, magnesium stearate, aluminum hydroxide, alginic acid, and water, or any combination thereof. In some embodiments, the one or more pharmaceutically acceptable excipients is selected from lactose, glucose, sucrose, mannitol, saccharin sodium, sodium benzoate, cellulose, sodium carboxymethyl, propylene glycol, glycerin, sorbitol, magnesium hydroxide, magnesium stearate, aluminum hydroxide, alginic acid, and water, or any combination thereof. In some embodiments, the one or more pharmaceutically acceptable excipients is selected from lactose, glucose, sucrose, mannitol, saccharin sodium, sodium benzoate, sorbitol, magnesium hydroxide, magnesium stearate, aluminum hydroxide, and water, or any combination thereof. In some embodiments, the one or more pharmaceutically acceptable excipients is selected from lactose, glucose, sucrose, mannitol, sorbitol, magnesium hydroxide, magnesium stearate, aluminum hydroxide, and water, or any combination thereof. In some embodiments, the one or more pharmaceutically acceptable excipients is selected from glucose, sucrose, mannitol, sorbitol, magnesium hydroxide, and magnesium stearate, or any combination thereof. In some embodiments, the one or more pharmaceutically acceptable excipients is selected from mannitol, and magnesium stearate, or any combination thereof.

Pharmaceutical Composition

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A pharmaceutical composition as described herein may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, scaled capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-2-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs. For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

A pharmaceutical composition can be administered by a variety of methods known in the art. The routes and/or modes of administration vary depending upon the desired results. Depending on the route of administration, the pharmacologically active agent may be coated in a material to protect the therapeutic agent or agents from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

EXAMPLES

The invention now being generally described, it will be more readily understood by reference to the following examples which are included merely for purposes of illustration of certain aspects and embodiments of the present invention, and are not intended to limit the invention in any way. As used below, and throughout the description of the invention, the following abbreviations, unless otherwise indicated, shall be understood to have the following meanings:

| | |
|---|---|
| AA | Anaplastic astrocytoma |
| AE | Adverse event |
| AG | Anaplastic glioma |
| ALT | Alanine aminotransferase |
| ANC | Absolute neutrophil counts |
| AO | Anaplastic oligodendroglioma |
| AOA | Anaplastic oligoastrocytoma |
| ASCO | American Society of Clinical Oncology |
| AST | Aspartate aminotransferase |
| AUC | Area under the concentration curve |
| BCNU | Carmustine |
| BSA | Body surface area |
| BUN | Blood urea nitrogen |
| bw | Body weight |
| CBC | Complete blood count |
| CBR | Clinical benefit response |
| CCNU | Lomustine (gleostine) |
| $C_{max}$ | Observed maximum concentration |
| $C_{min}$ | Observed minimum concentration |
| CNS | Central nervous system |
| CR | Complete response |
| CRF | Case report form(s) |
| CRO | Contract (or clinical) research organization |
| CSR | Clinical study report |
| CTCAE | Common Terminology Criteria for Adverse Events |
| CTP | Closed testing procedure |
| CV | Coefficient of variation |
| DFMO | α-Difluoromethylornithine, eflornithine |
| DOR | Duration of objective response |
| EBRT | External beam radiation therapy |
| ECG | Electrocardiogram |
| eCRF | Electronic case report form(s) |
| EDC | Electronic data capture |
| EORTC | European Organisation for Research and Treatment of Cancer |
| EU | European Union |
| FAS | Full analysis set |
| FDA | (United States) Food and Drug Administration |
| FLAIR | Fluid attenuated inversion recovery |
| GBM | Glioblastoma multiforme |
| GCP | Good Clinical Practice (Guidelines) |
| Gd | Gadolinium |
| HDPE | High-density polyethylene |
| HR | Hazard ratio |
| IB | Investigator's brochure |
| ICH | International Conference on Harmonisation |

50

-continued

| | |
|---|---|
| IDH1/2 | Isocitrate dehydrogenase 1/2 gene |
| IDMC | Independent Data Monitoring Committee |
| IEC | Independent Ethics Committee |
| IND | Investigational New Drug (Application) |
| IRB | Institutional review board |
| ITT | Intention-to-treat |
| IUD | Intrauterine device |
| IUS | Intrauterine hormone-releasing system |
| IV | Intravenous |
| KPS | Karnofsky Performance Status |
| LDH | Lactate dehydrogenase |
| LLN | Lower limit of the normal range |
| MDACC | The University of Texas M.D. Anderson Cancer Center |
| MedDRA | Medical Dictionary for Regulatory Activities |
| MG | Malignant glioma |
| MGBG | Methylglyoxal bis (guanylhydrazone) |
| MGMT | $O^6$-Methylguanine DNA methyltransferase |
| min | Minute |
| mmHg | Millimeters mercury |
| MRI | Magnetic resonance imaging |
| MTD | Maximum tolerated dose |
| nM | NanoMolar |
| NCI | National Cancer Institute |
| NYHA | New York Heart Association |
| OBF | O'Brien Fleming |
| ODC | Ornithine decarboxylase |
| ORR | Objective response rate |
| OS | Overall survival |
| OS-18 | Overall survival at 18 months |
| PCV | Procarbazine, lomustine, and vincristine |
| PD | Progressive disease |
| PFS | Progression free survival |
| PK | Pharmacokinetic |
| PR | Partial response |
| QID | Four times daily |
| QTc | Corrected QT interval |
| RT | Radiation therapy |
| SADR | Serious Adverse Drug Reaction |
| SAE | Serious adverse event |
| SAMDC | S-adenosyl-methionine decarboxylase |
| SD | Stable disease |
| SDS | Safety Data Sheets |
| StD | Standard deviation |
| SUSAR | Suspected Unexpected Serious Adverse Reaction |
| TEAE | Treatment emergent adverse event |
| ULN | Upper limit of the normal range |
| UK | United Kingdom |
| US | United States |
| WHO | World Health Organization |

Figure 1B:
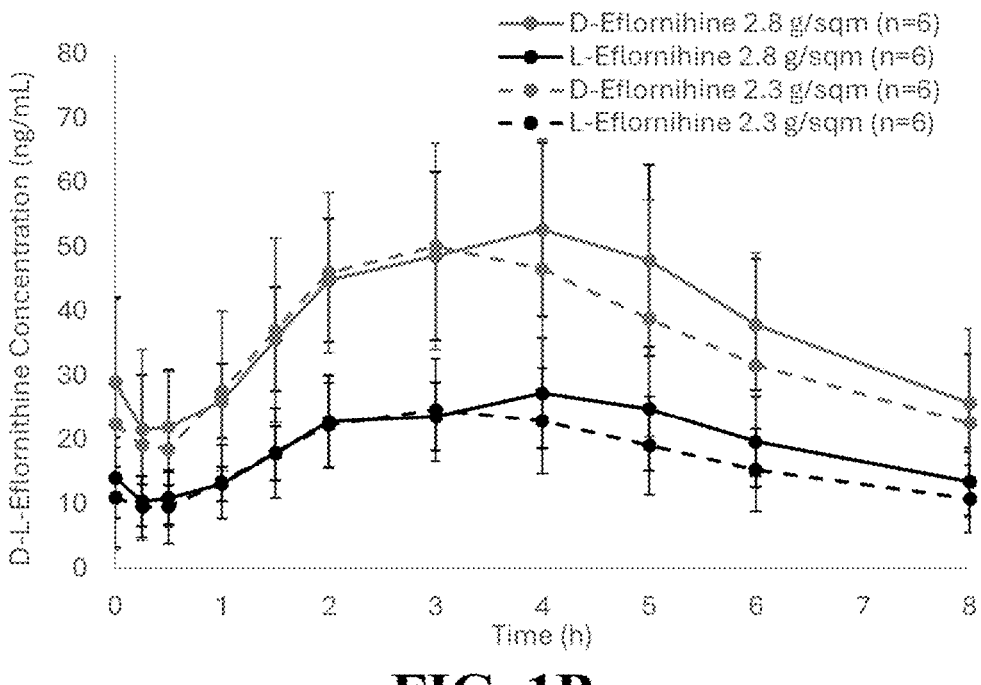

Example 1—Dose Determination and Clinical Pharmacokinetics—Eflornithine & Lomustine Eflornithine is a cytostatic drug that may interfere with mitosis and malignant progression. As eflornithine has a short half-life, it has to be administered every 6 to 8 hours. The human pharmacokinetic (PK) data following oral administration of eflornithine to a small number of cancer patients (n=6; doses 2.3 and 2.8 g/m$^2$) was evaluated (FIG. 1A and FIG. 1B). Time to peak Concentrations (Tmax) was similar between doses and days with median values ranging between 2.6 and 3.5 hours. The half-life ($T_{1/2}$) was similar between doses and days with mean values ranging from 2.6 to 3. 8 hours.

It has been reported that the recommended dose for treating naïve patients with lomustine was 130 mg/m². The phase 3 study of the present disclosure (Example 2) started with a reduced dose of 110 mg/m² because the patients had a higher tendency to have compromised bone marrow function due to administration of cytotoxic agent, e.g., temozolomide. After the completion of the second preplanned safety analysis with 42 patients who had completed 28 days of therapy, dose of lomustine was reduced further 90 mg/m² for patients. The present Example and Example 2 demonstrate that even after implementing such a significant reduction of the dose of lomustine from the standard of care dose, e.g., 130 mg/m² or 110 mg/m², the treatment in the combination arm was well tolerated.

Example 2—Human Clinical Trials—Phase 3

Overview

The present Example demonstrates a Phase 3, randomized, open-label, multicenter, active-controlled study to evaluate the safety and efficacy of eflornithine with lomustine compared to lomustine alone in patients with astrocytoma that progress/recur after irradiation and adjuvant temozolomide chemotherapy.

Eflornithine

Eflornithine oral solution, 150 mg/ml, was a clear liquid containing 13.9% eflornithine free base equivalent (18% eflornithine monohydrochloride hydrate). The oral solution was aqueous-based and contained the following inactive ingredients: glycerin, propylene glycol, saccharin sodium dihydrate and sodium benzoate. The dose of eflornithine was based on body surface area. Administration of eflornithine was orally 2.8 g/m² three-times daily (every 8 hours) on a 2 week on, 1 week off schedule using the dosing cup provided. This administration permitted combination with lomustine. Dosage modifications were recommended for patients with eflornithine-related side effects.

Eflornithine oral solution was packaged in white 16 oz. HDPE bottles. Each bottle contained 463 ml of the solution. The bottles were induction sealed and closed with child resistant HDPE cap. Dosing cups were provided for accurate administration. Eflornithine was stored at room temperature of 25° C. (77° F.) with excursions permitted between 15° C. and 30° C. (59° F. and 86° F.). It was protected from cold and light.

Lomustine

Lomustine (CeeNU® and Gleostine®) was obtained from a commercial source in 10 mg, 40 mg, and 100 mg capsules for oral administration. Inactive ingredients in lomustine capsules were magnesium stearate and mannitol. The dose of lomustine was based on body surface area. Administration of lomustine was orally 90 mg/m² every 6 weeks with or without food. lomustine was not to be taken on the same day as an eflornithine dose.

Lomustine capsules were packaged in individual bottles of 20 capsules each. Lomustine was stored at room temperature of 25° C. (77° F.) with excursions permitted between 15° C. and 30° C. (59° F. and 86° F.). The capsules were protected from cold and light.

Study Design

Figure 8:
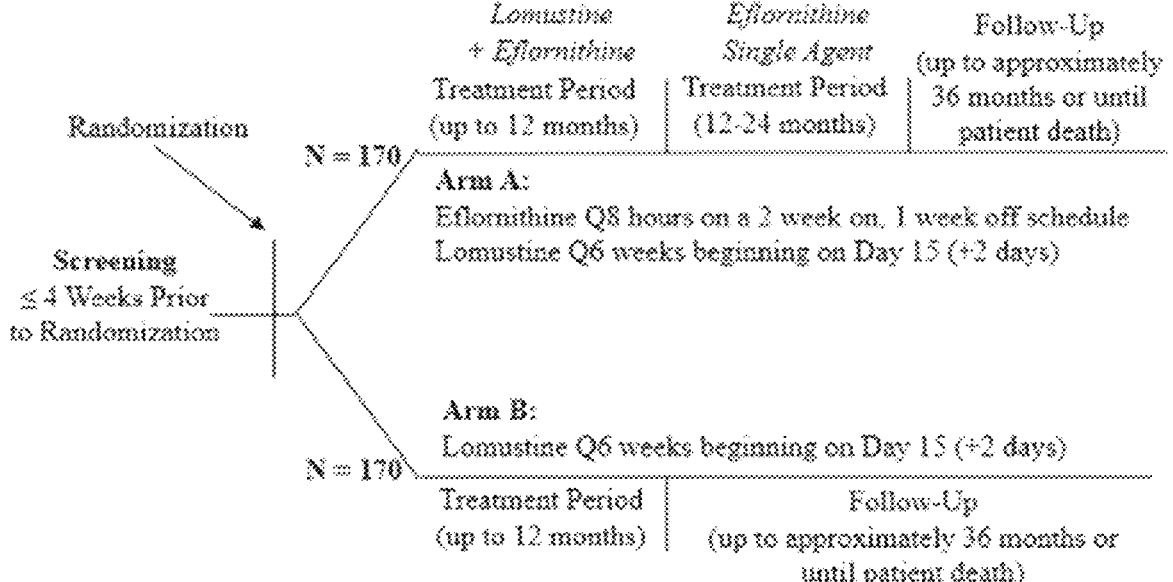
FIG. 8 shows a schematic of the study design involving patients with astrocytoma.

Eligible patients had biopsy-proven astrocytoma prior to randomization or prior to EBRT and adjuvant temozolomide chemotherapy. In the latter case, there was MRI evidence for tumor progression that reflected progression of astrocytoma and not transformation to glioblastoma or radiation therapy (RT) necrosis, which was based on MRI criteria for these two conditions at the time of the present example. Approximately 340 patients met the eligibility criteria and were enrolled. Of the approximately 340 patients in total: 170 patients were randomly assigned to Treatment Arm A and 170 patients were randomly assigned to Treatment Arm B. The implemented study design is presented in FIG. 8, and described in the text that follows.

Duration of Study/Treatment

The duration of the study was up to approximately 62 months in total, or concluded with patient death:

Screening Period—Had a maximum duration of 4 weeks.

Treatment Period:

Treatment Arm A: Patients received eflornithine for up to a total of 24 months. Patients received lomustine for up to 6 cycles or 12 months, whichever came first.

Treatment Arm B: Patients received lomustine for up to 6 cycles or 12 months, whichever came first.

End of Treatment Visit—Had a minimum duration of 4 weeks post last treatment for both arms.

Follow-Up Period—Was up to approximately 36 months, or concluded with patient death.

Treatment Arm A (Eflornithine was administered on a 2 week on, 1 week off schedule+Lomustine was administered every 6 weeks (n=170)):

Eflornithine 2.8 g/m² was administered orally every 8 hours on a 2 week on, 1 week off schedule, without regard to food. Any missed doses of study drug(s) were skipped, and the patient took the next dose at the assigned time.

Lomustine 90 mg/m² was administered orally once on Day 15 (12 days) and once every 6 weeks thereafter, without regard to food. Lomustine was administered during the eflornithine off-week and was not taken on the same day as an eflornithine dose.

All patients initially received both eflornithine and lomustine. Patients received lomustine for up to 6 cycles or 12 months, if AEs allowed, or until tumor progression by MRI, or death, whichever came first. Patients whose astrocytoma tumors did not progress or recured continued to receive single agent eflornithine for up to a total of 2 years.

Lomustine dose was delayed for a maximum of 6 weeks due to toxicities. If dose delay due to lomustine was longer than 6 weeks beyond the next scheduled dose, then lomustine was permanently discontinued and patient continued single agent eflornithine for a total treatment of up to 2 years.

If dose delay was due to an eflornithine-related toxicity, lomustine dosing may have continued while eflornithine was held. Patients may have continued single agent lomustine until eflornithine-related toxicities had resolved, after which eflornithine was restarted.

Treatment Arm B (Lomustine was administered every 6 weeks (n=170)):

Lomustine 110 mg/m² was administered orally once on Day 15 (+2 days) and once every 6 weeks thereafter, without regard to food.

Patients received lomustine for up to 6 cycles or 12 months, if AEs allowed, or until tumor progression by MRI, or death, whichever came first.

Lomustine dose was delayed for a maximum of 6 weeks due to toxicities. If dose delay was longer than 6 weeks beyond the next scheduled dose, then lomustine was permanently discontinued.

Doses for both study drugs were based on body surface area (BSA) which were calculated based on institutional guidelines (i.e., Mosteller or Dubois).

Randomization was stratified by age≤45 years or >45 years, region (US vs Ex-US), IDH-1 status (wild type vs mutant), and number of prior surgeries (biopsy only vs 1 or 2 surgical resections (e.g., surgical resection at primary diagnosis and secondary surgical resection after first progression/recurrence)).

Objectives and Endpoints

The primary objective of the present Example was to demonstrate superiority in overall survival (OS) and comparable safety when eflornithine was added to lomustine compared to lomustine alone in patients with astrocytoma that progressed/recurred after irradiation and adjuvant temozolomide chemotherapy.

The primary endpoint was the duration OS as measured from the date of randomization to the date of death due to any cause.

The following secondary objectives of the present Example that were determined:

Progression-free survival (PFS);

The objective response rate (ORR);

OS for IDH-1 mutant patients; and

OS for IDH-1 wild type patients.

The secondary endpoints included:

Efficacy: PFS; ORR; OS for IDH-1 mutant patients; and OS for IDH-1 wild type patients.

Safety: Incidence of treatment emergent adverse events; Incidence of serious adverse events; and Changes and shifts from baseline in hematology and serum chemistry values, ECGs, and vital signs.

The exploratory objectives of this study that were determined:

Clinical benefit response (CBR) based on magnetic resonance imaging (MRI) criteria;

OS rate at 18 months (OS-18);

Relevance of OS, PFS, ORR, and CBR to commonly used molecular/genetic biomarkers obtained from most recent pre-study tumor samples (i.e., p53 mutation, deletion of chromosomes 1p and 19q, IDH1 mutations, ATRX mutation, Mib-1 labeling index, MGMT promoter methylation); and Steady-state plasma pharmacokinetics (PK) for eflornithine in patients within 2 weeks of initial dosing.

Inclusion Criteria

Patients who met all of the following inclusion criteria were enrolled in this study:

1. The ability to understand and sign a written informed consent form, which must be obtained prior to initiation of study procedures.

2. Age≥18 years.

3. Surgical or biopsy-proven diagnosis of WHO grade 3 astrocytoma.

4. Received EBRT and temozolomide chemotherapy prior to first tumor progression or recurrence of WHO grade 3 astrocytoma.

5. First astrocytoma tumor progression or recurrence≤6 months prior to randomization based on MRI using T2 hyperintensity, Gd-contrast enhancement, or both.

6. To avoid enrollment of patients with glioblastoma, patients with Gd-contrast enhancing tumors were eligible if there is no necrosis seen on MRI and any one of the following criteria was true:

a. Gd-contrast lesion margins were clearly defined, b. Gd-contrast lesions were only measurable in one dimension, c. Gd-contrast lesion had two perpendicular diameters less than 10 mm, d. Gd-contrast lesion had two perpendicular diameters greater than 10 mm but less than 20 mm and lesion did not demonstrate central necrosis, or c. Recent histopathological confirmed WHO grade 3 astrocytoma.

7. Completion of EBRT≥6 months prior to randomization.

8. Stained, unstained slides or tumor tissue block(s) were available from their most recent tumor surgery and were available for central histological confirmation.

9. A patient whose astrocytoma tumor had progressed or recurred and had another surgical resection prior to randomization was eligible if a) pathology review confirmed astrocytoma, and b) post-surgical MRI demonstrated measurable tumor on T2 FLAIR.

10. If taking corticosteroids, then was on a stable or decreasing dose for at least 5 days prior to the screening MRI.

11. Karnofsky Performance Status (KPS) score of ≥70.

12. Off anticancer therapy for at least 4 weeks and recovered from any significant treatment-related toxicities to grade≤1 prior to randomization.

13. Adequate recovery from any major surgery was required; at least 4 weeks elapsed from the time of any major surgery and recovered from all surgery-related toxicities to grade≤1 prior to randomization.

14. Adequate hematologic function (ANC≥1,500/μL, platelet count≥100,000/μL, and hemoglobin≥10.5 gm/dL) within 14 days prior to randomization.

15. Total bilirubin≤1.5× upper limit of normal (ULN) within 14 days prior to randomization.

16. Hepatic transaminases (AST and ALT) S 2×ULN within 14 days prior to randomization.

17. Adequate renal function (serum creatinine≤1.5×ULN) within 14 days prior to randomization.

18. Life expectancy≥6 months.

19. Female patients of childbearing potential agreed to utilize acceptable contraceptive methods from screening throughout the duration of the study period, and for 30 days following the last dose of study drug. Abstinence was an acceptable method of contraception. Otherwise, consistent and current use of 1 of the following methods of birth control was accepted: oral contraceptive, intrauterine device (IUD), intrauterine hormone-releasing system (IUS), tubal sterilization, Essure micro-insert system, or vasectomy in the male partner. Female patients refrained from egg donation and in vitro fertilization during treatment and until at least 30 days after the last dose of study drug.

20. Male patients agreed to abstain from sexual intercourse or used an acceptable contraceptive method (e.g. condoms) from screening throughout the duration of the study period, and for 90 days following the last dose of study drug. Male patients refrained from sperm donation during treatment and until at least 90 days after the last dose of study drug.

Exclusion Criteria

Patients who met any of the following exclusion criteria were excluded from participation:

1. MRI defining progression that was consistent with a diagnosis of glioblastoma or radiation necrosis.

2. Patients who were considered to be refractory to EBRT and temozolomide but who had not progressed.

3. Prior systemic therapy for recurrence of astrocytoma.

4. Presence of extracranial or leptomeningeal disease.

5. Prior lomustine use.

6. History of other invasive malignancy, unless adequately treated with curative intent and with no known active disease present within 2 years prior to the first dose of study drug. Patients with non-melanoma skin cancer, carcinoma in situ (including superficial bladder cancer), cervical intraepithelial neoplasia and organ-confined prostate cancer deemed by the Investigator to be at low risk of recurrence were not excluded.

7. Active infection or serious intercurrent medical illness.

8. Known to be HIV positive or had an AIDS-related illness, active Hepatitis B Virus (HBV), or active Hepatitis C Virus (IICV).

9. Poorly controlled seizures.

10. Unable to undergo an MRI with contrast.

11. Uncontrolled or severe cardiovascular disease, including myocardial infarction or unstable angina within 6 months prior to study treatment, New York Heart Association (NYHA) Class III or IV congestive heart failure, serious arrhythmias requiring medication for treatment, clinically significant pericardial disease, or cardiac amyloidosis.

12. Malabsorption syndrome, history of resection of the stomach or small bowel, active ulcerative colitis or Crohn's disease, or partial or complete bowel obstruction or other conditions that was expected to alter the absorption or PK of study drugs.

13. Receipt of any other anticancer therapy.

14. Concurrent use of any other investigational agent during the study or within 30 days prior to randomization.

15. Any other clinical condition or prior therapy that, in the opinion of the Investigator, made the patient unsuitable for the study.

16. Pregnant or breastfeeding.

Dose Modification and Toxicity

Toxicity

Toxicity descriptions and grading scales found in the revised National Cancer Institute (NCI) Common Terminology Criteria for Adverse Events (CTCAE) version 4.03 was utilized for AE reporting. Examples of hematologic toxicity grades from the CTCAE is shown in Table 1 below.

Study drug treatment were continued as long as there was no tumor recurrence or progression, or until the duration of therapies was reached. Subsequent drug dosing was determined by the patient's recovery from any treatment-related adverse events (AEs) associated with the prior dose of study drug(s). If study drug dosing was delayed due to any toxicity, dosing was resumed at the earliest possible opportunity after a patient had recovered from such toxicity.

Subsequent Lomustine Drug Dosing

The next lomustine dose was not administered unless the patient had recovered from lomustine-related toxicities. For lomustine, recovery was defined as occurred when both of the following conditions were met:

All lomustine-related hematologic toxicities shown in Table 1 had subsided to a grade 1 level or had returned to baseline; this excluded lymphopenia.

All lomustine-related non-hematologic toxicities had subsided to a grade 1 level or had returned to baseline; this excluded alopecia and nausea/vomiting.

A lomustine dose was delayed for a maximum of 6 weeks due to toxicities. If a dose delay lasted more than 6 weeks beyond the next scheduled dose, then lomustine was permanently discontinued. If the patient had received both eflornithine and lomustine (Treatment Arm A), the patient continued single agent eflornithine for a total treatment of up to 2 years.

Subsequent Eflornithine Drug Dosing

The next eflornithine dose was not administered unless the patient had recovered from toxicity due to eflornithine treatment-related AEs/toxicities. For eflornithine, recovery was defined as occurred when both of the following conditions were met:

Eflornithine-related diarrhea, nausea, or vomiting had recovered to grade I level or had returned to baseline (see Dose Modification and Table 1).

Grade 4 eflornithine-related hearing impairment or tinnitus had recovered to grade 2 or baseline (see Dose Modification and Table 1).

If a dose delay was due to an eflornithine-related toxicity, lomustine dosing was continued while eflornithine was held. Patients continued on single agent lomustine until eflornithine-related toxicities had resolved, after which eflornithine was restarted.

Dose Modification

Patients received the same dose or a reduced dose for the next treatment, depending upon the toxicities observed.

TABLE 1

| Relationship of Hematologic Toxicity to CTCAE Grades | | | | |
|---|---|---|---|---|
| | CTCAE Grades | | | |
| Hematologic Toxicity | 1 | 2 | 3 | 4 |
| White Blood Cells (/µL) | <LLN to 3000 | <3,000 to 2,000 | <2,000 to 1,000 | <1000 |
| Neutrophils (/µL) | <LLN to 1500 | <1500 to 1,000 | <1,000 to 500 | <500 |
| Platelets (/µL) | <LLN to 75,000 | <75,000 to 50,000 | <50,000 to 25,000 | <25,000 |
| Hemoglobin (g/dL) | <LLN to 10.0 | <10.0 to 8.0 | <8.0 | Life-threatening |

LLN = lower limit of normal

Note:

Lymphopenia was excluded from the table as it is considered an independent hematologic variable in glioma patients being treated with alkylating drugs; it is typically treated with either trimethoprim/sulfamethoxazole or dapsone for prophylaxis against pneumocystis carinii pneumonia.

If multiple toxicities were seen, the subsequent dose to be administered in a subsequent treatment was based on the most severe toxicity observed.

For a hematologic toxicity, the nadir (lowest) count that was measured during the prior treatment was used to determine severity. In the case of multiple hematologic toxicities, the toxicity with the highest grade was used to determine dose modifications or delays. For a non hematologic toxicity, the most severe episode during the prior treatment was used to determine severity.

Dose Modification—Treatment Arm A

For a patient who received both eflornithine and lomustine, the subsequent doses of eflornithine and lomustine were determined from Table 2 and Table 3, based on the worst toxicity grade observed.

TABLE 2

| Lomustine Doses for Subsequent Treatment Based on CTCAE Toxicity Grade | |
| --- | --- |
| Grade | Remarks |
| Normal | Kept at original lomustine dose |
| 1 | Kept at original lomustine dose |
| 2 | 75% of previous actual lomustine dose |
| 3 | 50% of previous actual lomustine dose |
| 4 | 50% of previous actual lomustine dose |

Patients who developed a specific AE of hearing impairment, tinnitus, diarrhea, nausea, or vomiting that was considered related to eflornithine was dose adjusted according to Table 3 based on the worst toxicity grade observed.

Patients with dose delays due to lomustine-related toxicity continued to receive eflornithine once the toxicity had subsided to grade 2 or returned to baseline. In cases where the causative agent for the prolonged toxicity was unclear (i.e., lomustine vs eflornithine) and the Investigator wished to continue therapy when more than a 6-week dose delay had occurred, the study medical monitor was informed.

TABLE 3

| Eflornithine Doses for Subsequent Treatment Based on CTCAE Toxicity Grade | | |
| --- | --- | --- |
| Grade | Eflornithine Dose (g/m$^2$) | Remarks |
| | | Treatment Based on CTCAE Hearing Impairment: |
| 1 | 2.8 | Kept at original eflornithine dose |
| 2 | 2.1 | 75% of original eflornithine dose |
| 3 | 2.1 | 75% of original eflornithine dose |
| 4 | 1.4 | 50% of original eflornithine dose |
| | | Tinnitus: |
| 1 | 2.8 | Kept at original eflornithine dose |
| 2 | 2.8 | Kept at original eflornithine dose |
| 3 | 2.1 | 75% of original eflornithine dose |
| | | Diarrhea, Nausea*, or Vomiting: |
| 1 | 2.8 | Kept at original eflornithine dose |
| 2 | 2.8 | Kept at original eflornithine dose |
| 3 | 2.1 | 75% of original eflornithine dose |
| 4 | 1.4 | 50% of original eflornithine dose |

*Nausea CTCAE grading was only from grade 1 to 3.

For hearing impairment:

Equal to CTCAE grade 2 or grade 3 and was considered related to study treatment, eflornithine dose was immediately reduced according to Table 3.

Equal to CTCAE grade 4, eflornithine was delayed until recovery to at least grade 2 or baseline. Upon resumption of eflornithine, subsequent eflornithine doses was reduced according to Table 3.

In the absence of audiometry analysis, patients that presented clinically relevant hearing impairment were considered to have grade 2 or grade 3 toxicity and had their dose of eflornithine immediately reduced according to Table 3. Audiometry was obtained as necessary per Investigators' judgement.

For tinnitus:

Equal to CTCAE grade 3 and was considered related to study treatment, eflornithine dose was immediately reduced according to Table 3.

For diarrhea, nausea, or vomiting:

Investigator judgment prevailed with respect to whether the patient was a candidate to resume eflornithine after a grade 4 episode.

Patients who experienced grade 1 or less after an initial eflornithine dose reduction had their dose increased to the next highest dose level (i.e., from 1.4 to 2.1 g/m$^2$ every 8 hours or from 2.1 to 2.8 g/m$^2$ every 8 hours) at the discretion of the treating Investigator. In no case was a patient's eflornithine dose escalated to higher than the initial starting dose of 2.8 g/m$^2$ every 8 hours.

Dose Modification—Treatment Arm B

For a patient who received lomustine, the subsequent doses was determined from Table 2 based on the worst toxicity grade observed.

Study Procedures

The study procedures conducted for each patient enrolled in the study are presented in tabular form in Table 4.1, Table 4.2 and described in the text that follows.

Screening Visit

Patients were screened up to 4 weeks prior to randomization to determine eligibility for participation in the study.

The following was performed and documented within 4 weeks prior to randomization, unless otherwise specified:

Written informed consent;

Medical history, including history of astrocytoma disease-related events, and surgery;

Obtained documentation of evaluable disease (within 14 days prior to randomization);

Obtained histopathology report that confirmed a diagnosis of astrocytoma (WHO grade 3) and slides or tissue block(s) were sent to the Referee Neuro-pathologist(s);

Obtained the two most recent brain MRI scans, which included the MRI that defined tumor progression, with the latest MRI being obtained within 14 days of last tumor biopsy if biopsy occurred. These scans were submitted to Orbus and included in the clinical data repository;

Completed physical examination including vital signs, body weight and height;

KPS;

Urinalysis;

Steroid and anticonvulsant medication documentation;

Blood sample collection for the following laboratory analyses: (standard of care laboratory analyses [(e.g., chemistry)] performed prior to the written informed consent, was accepted if within 14 days prior to randomization):

Serum pregnancy test (females of childbearing potential only, within 14 days prior to randomization), Chemistry (including liver function tests), Hematology: completed blood count (CBC) with differential white cell count, and platelet count; and Recorded any serious adverse events (SAEs) and all AEs related to protocol-mandated procedures occurring after the consent form was signed; and Obtained concomitant medications taken within 30 days of the screening visit.

From the time of obtaining informed consent through the first administration of investigational medicinal product, recorded all SAEs, as well as any adverse events related to protocol-mandated procedures on the adverse events case report form (eCRF). All other untoward medical occurrences observed during the screening period, including exacerbation or changes in medical history were captured on the medical history eCRF.

Randomization (Week 1)

Once eligibility was confirmed, the patient was randomized to either Treatment Arm A or Treatment Arm B using the Electronic Data Capture (EDC) system. The EDC also assigned a unique patient number to the patient. Once a patient number was assigned, it was not reassigned to any other patient.

The following were completed at the Randomization Visit (unless otherwise specified):

Randomization (was performed up to 2 days prior to the in-clinic randomization visit);

Patient number assignment (was performed up to 2 days prior to the in-clinic randomization visit);

Targeted physical examination;

Vital sign measurement (blood pressure, pulse, respiration rate, and temperature);

Weight;

KPS;

Brain MRI (was obtained within 14 days prior to randomization). This scan was submitted to Orbus and included in the clinical data repository;

12-lead ECG (was obtained within 14 days prior to randomization);

Audiometry (was obtained within 14 days prior to randomization);

Pulmonary function test via forced vital capacity (was obtained within 14 days prior to randomization);

Blood sample collection for the following laboratory analyses: (screening laboratory procedures was used as baseline if performed within 1 week prior to the randomization visit):

Chemistry (including liver function tests),

Hematology: completed blood count (CBC) with differential white cell count, and platelet count, and PK (Treatment Arm A sub-study patients only);

Dispense study drug, as appropriate;

Review of changes in concomitant medications; and

Review of AFs.

Treatment Assessments

Week 2 (for a subset of Treatment Arm A patients only: n=approximately 20). PK and 12-lead ECG was performed on the same day (between Days 7 and 14).

PK was drawn approximately 3-5 hours post dose and 6-8 hours post dose of the visit day.

12-lead ECG was performed at approximately 3-5 hours post dose of the visit day.

Week 3 (for a subset of Treatment Arm B patients only: n=approximately 20).

12-lead ECG was performed within one day of initial lomustine dosing.

Year 1 and Year 2. The following assessments were completed at Week 8 (+2 weeks), and then every 6 weeks (+2 weeks) thereafter through Month 6. Beginning Month 7, these assessments were completed every 10 weeks (12 weeks) through Month 12. Year 2 visits had occurred every 3 months (+2 weeks) (Note: Audiometry, urinalysis, and pulmonary function test was performed every 3 months at the closest scheduled study visit.):

Targeted physical examination;

Vital signs measurement (blood pressure, pulse, respiration rate, and temperature);

Weight;

KPS;

Brain MRI (performed per institutional standard of care). MRI scans that showed evidence of progression or response were submitted to Orbus and included in the clinical data repository;

Audiometry (performed every 3 months post randomization);

Urinalysis (performed every 3 months post randomization);

Pulmonary function test via forced vital capacity (performed every 3 months post randomization and only during lomustine treatment);

Blood sample collection for the following laboratory analyses:

Chemistry (including liver function tests),

Hematology: CBC with differential white cell count, and platelet count, and

Lab draws to assess hematological toxicities for lomustine was performed weekly after the first dose of lomustine per the prescribing information and was continued during lomustine treatment only;

Dispense study drug, as appropriate;

Review changes in concomitant medications; and

Review of AFs.

Evaluation of Pharmacokinetics

Blood samples were collected at randomization and within 2 weeks of initial dosing in a subset of Treatment Arm A patients to evaluate steady-state plasma PK of eflornithine.

Evaluation of ECG

Descriptive statistics were performed on a subset of patients. A 12-lead ECG was obtained at baseline, Week 2 or 3 (depending on Treatment Arm assignment), and End of Treatment. The ECG parameters assessed included heart rate and PR, QRS, and QTc intervals.

Evaluation of Biomarkers

Tissue slides or tumor block were collected to determine relevance of OS, PFS, ORR, and CBR to commonly used molecular/genetic biomarkers (e.g., CDKN2A/B mutations, p53 mutation, deletion of chromosomes 1p and 19q, IDH1 mutations, IDH2 mutations, ATRX mutation, Mib-1 labeling index, MGMT promoter methylation, TERT promoter mutations, EGFR mutations, chromosome 7/10 mutations).

End of Treatment Assessment

An End of Treatment Visit was performed upon termination of all study treatments (eflornithine plus lomustine and lomustine alone). The following assessments were performed a minimum of 4 weeks after the last dose of study drug(s):

Complete physical examination including vital signs and body weight;

KPS;

12-lead ECG;

Blood sample collection for the following laboratory analyses:

Chemistry (including liver function tests), and

Hematology: CBC with differential white cell count, and platelet count;

Review of changes in concomitant medications; and

Review of AEs.

Follow-Up Period

For patients who experienced disease progression, information regarding future treatment(s) was collected and recorded on the eCRF. The following assessment was performed approximately every 2 months:

f Confirmed survival status via phone. Survival status was recorded on the eCR immediately after confirmation.

Discontinuation of Study Treatment

Patients were withdrawn or removed from study treatment at any time for the following reason:

Unacceptable toxicity, or toxicity that, in the judgment of the Investigator, compromised the ability to continue study-specific procedures or it was considered to not be in the patient's best interest to continue study treatment;

Disease progression;

Patient requested to discontinue study drug;

Patient was noncompliant; or

Pregnancy during the study.

TABLE 4.1

Study Procedures-Screening to Month 6

| Study Procedures | Screening[a] | Months 1-6 | | | | |
|---|---|---|---|---|---|---|
| | | Randomization | Week 2[d] | Week 3[j] | Week 8 | Every 6 Weeks |
| Informed Consent | X | | | | | |
| Medical History[i] | X | | | | | |
| Steroid and anticonvulsant medication documentation | X | | | | | |
| Complete[e]/Targeted Physical Exam | X[e] | X | | | X | X |
| 12-Lead ECG | | X[b] | | | | |
| Documentation of evaluable disease | X[b] | | | | | |
| Obtain histopathology report and slides/tissue block(s) for astrocytoma diagnosis confirmation | X | | | | | |
| Obtain two most recent brain MRI scans | X[g] | | | | | |
| Brain MRI | | X[b] | Per institution standard of care | | | |
| Audiometry | | X[b] | | | | X[f] |
| Urinalysis | X | | | | | X[f] |
| Height | X | | | | | |
| Weight | X | X | | | X | X |
| Vital signs | X | X | | | X | X |
| Karnofsky Performance Status | X | X | | | X | X |
| Serum Pregnancy Test[c] | X[b] | | | | | |
| Chemistry (including liver function tests) | X | X | | | X | X |
| Hematology | X | X | | | X | X |
| Lomustine Hematology Monitoring | | | Weekly per lomustine prescribing information | | | |
| Pulmonary function test[h] | | X[b] | | | | X[f] |
| PK Sub-study | | X | X | | | |
| 12-Lead ECG Sub-study | | | X | X | | |
| Study Drug Dispensation | | X | | | X | X |
| Survival Status | | | | | | |
| Concomitant Medications | X | X | | | X | X |
| Adverse Events and/or Serious Adverse Events | X | X | | | X | X |

TABLE 4.1-continued

| | Study Procedures-Months 7-12 to Follow-Up | | | |
|---|---|---|---|---|
| Study Procedures | Months 7-12 Every 10 weeks | Year 2 Every 3 months | End of Treatment | Follow-Up |
| Informed Consent | | | | |
| Medical History[j] | | | | |
| Steroid and anticonvulsant medication documentation | | | | |
| Complete[e]/Targeted Physical Exam | X | X | X[e] | |
| 12-Lead ECG | | | X | |
| Documentation of evaluable disease | | | | |
| Obtain histopathology report and slides/tissue block(s) for astrocytomadiagnosis confirmation | | | | |
| Obtain two most recent brain MRI scans | | | | |
| Brain MRI | | Per institution standard of care | | |
| Audiometry | X[f] | X | | |
| Urinalysis | X[f] | X | | |
| Height | | | | |
| Weight | X | X | X | |
| Vital signs | X | X | X | |
| Karnofsky Performance Status | X | X | X | |
| Serum Pregnancy Test[c] | | | | |
| Chemistry (including liver function tests) | X | X | X | |
| Hematology | X | X | X | |
| Lomustine Hematology Monitoring | Weekly per lomustine prescribing information | | | |
| Pulmonary function test[h] | X[f] | | | |
| PK Sub-study | | | | |
| 12-Lead ECG Sub-study | | | | |
| Study Drug Dispensation | X | X | | |
| Survival Status | | X | | X |
| Concomitant Medications | X | X | X | |
| Adverse Events and/or Serious Adverse Events | X | X | X | |

[a]Evaluations was completed within 4 weeks prior to randomization.
[b]Within 14 days prior to randomization.
[c]Females of childbearing potential only.
[d]PK and 12-lead ECG sub-studies (for Treatment Arm A patients) was performed on the sameday (between Days 7 and 14). PK was drawn approximately 3-5 hours post dose and approximately 6-8 hours post dose of the visit day. 12-lead ECG was performed at approximately 3-5 hours post dose of the visit day.
[e]Complete physical examinations were performed at Screening and End of Treatment only.
[f]Performed every 3 months post randomization.
[g]The two most recent MRI scans included the MRI that defined tumor progression, with the latest MRI being obtained within 14 days of last tumor biopsy if biopsy occurred.
[h]Performed only during lomustine treatment.
[i]Including history of astrocytoma disease-related events and surgery.
[j]Performed within one day of initial lomustine dosing for Treatment Arm B patients.

Statistical Considerations

The primary efficacy analysis was performed in accordance with the intention-to-treat (ITT) principle. All randomized patients were included in the primary efficacy analysis according to their randomly assigned study treatment, irrespective of the actual receipt of such treatment. The primary variable of OS was summarized descriptively using the Kaplan-Meier method. For both endpoints, the primary inferential comparison between treatment arms was performed using the log-rank test stratified by the randomization stratification factors for age, region, IDH-1 status, and number of prior surgeries. Estimation of the hazard ratio (HIR) for treatment arm was determined using a stratified Cox proportional hazards model, without any other covariate. Duration of OS in subgroups of IDH-1 mutant and wild type was analyzed similarly to the primary efficacy variable. PFS was summarized similarly to OS. ORR was estimated based on the proportion of patients in each treatment arm whose best overall response during the course of study treatment is CR or PR. Approximate 95% confidence intervals were calculated by treatment arm for the true ORR. The inferential comparison of the observed ORRs was made using the Cochran-Mantel-Haenszel chi-square test, stratified by age, region, IDH-1 status, and number of prior surgeries.

Multiplicity Adjustment

The overall type I error rate for the study was set at 0.05 (two-sided). If superiority of OS was demonstrated at either the interim or primary analysis, formal inferential comparisons between treatment arms was planned for the secondary endpoints PFS and ORR. The tests were performed in a sequential hierarchical manner based on a closed testing procedure (CTP). The CTP was employed to maintain control of the overall type I error rate to account for hypothesis testing of multiple secondary endpoints.

Sample Size

The sample size was calculated by assuming true median OS of 12 months for the treatment arm receiving lomustine monotherapy (control arm). It was hypothesized that true median OS would be 18 months or longer for the treatment arm receiving eflornithine plus lomustine (investigational arm). Under the assumption that OS followed an exponential probability distribution for each treatment arm, such an improvement represents a true hazard ratio of 0.667 (investigational arm/control arm). Inferential comparisons of OS was performed using a stratified log-rank test, stratifying on the randomization stratification factors for age, region, IDH-1 status, and number of prior surgeries. Total accrual of approximately 340 patients (170 per treatment arm) and total information of 261 deaths was estimated to provide 90% power to detect a 33% reduction in the OS failure hazard rate, based on a two-sided overall type I error of 5% with adjustment for one interim analysis for superiority at 75% of total deaths, using O'Brien-Fleming stopping boundary (SEQDESIGN procedure, SAS version 9.4).

Results

Figure 2:
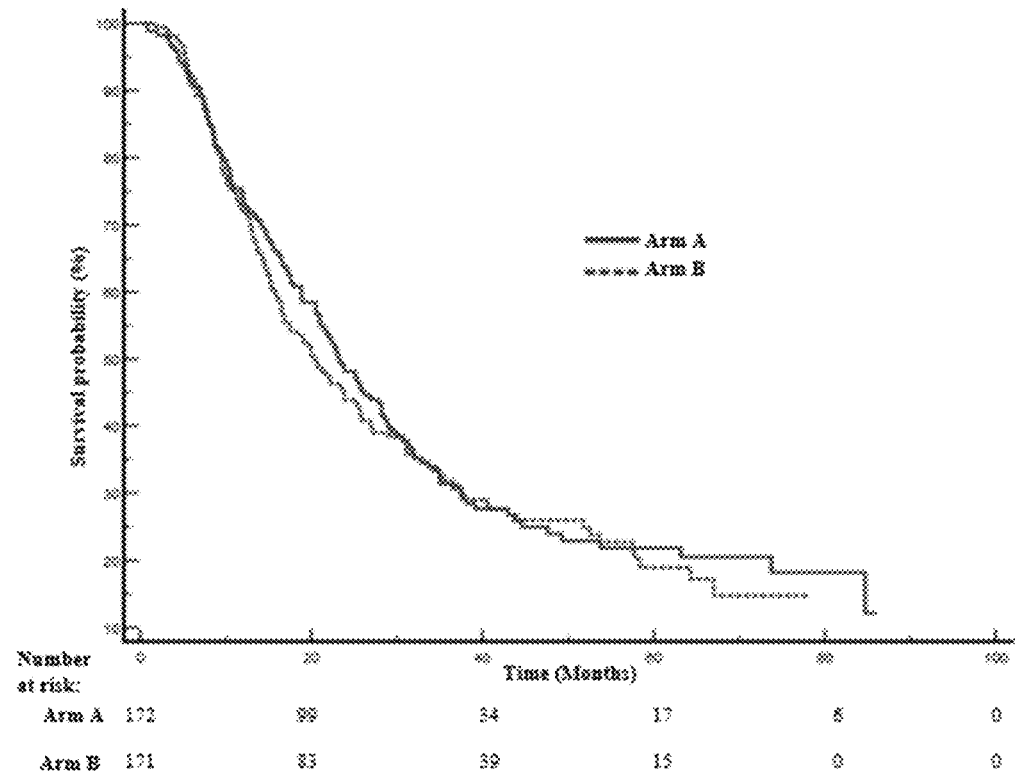
FIG. 2 shows overall survival (OS) results for all intension-to-treat (ITT) patients with further summary statistics in Table 5.
Figure 3:
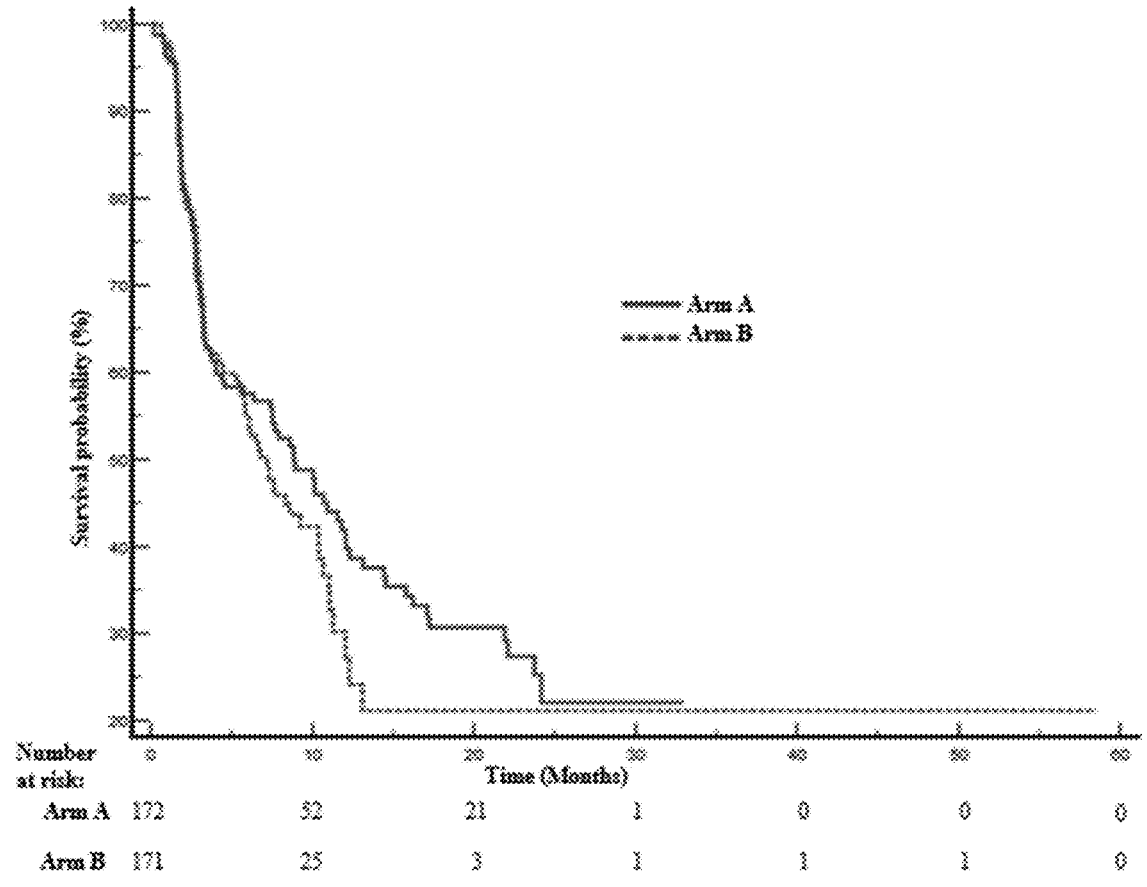
FIG. 3 shows progression free survival (PFS) results for all intension-to-treat (ITT) patients with further summary statistics in Table 6.

Based on previous studies (Levin et al., Clinical importance of eflornithine (α-difluoromethylornithine) for the treatment of malignant gliomas, CNS Oncol. (2018) 7(2), CNS16), it was expected that cytostatic action of eflornithine would be relevant to inhibition of the tumor growth in patients with glioma irrespective of its genetic profile. Contrary to this expectation, the results of the current study revealed that when viewed in aggregate (all patients intended to treat), the overall survival and progression free survival of the patients treated during the study were not significantly affected by the addition of eflornithine to the lomustine-only standard of care therapy (FIG. 2 and Table 5; and FIG. 3 and Table 6).

TABLE 5

Overall Survival (OS) Results for Patients Summary Statistics

| Arm | Number of Events | | Number Censored | | |
|---|---|---|---|---|---|
| | N | % total sample size | N | % total sample size | Total Sample Size |
| A (lomustine + eflornithine) | 129 | 75.0 | 43 | 25.0 | 172 |
| B (Lomustine only) | 128 | 74.9 | 43 | 25.2 | 171 |
| Overall | 257 | 74.9 | 86 | 25.1 | 343 |

| Arm | Median OS | 95% CI for the Median |
|---|---|---|
| A (lomustine + eflornithine) | 23.4 | 20.500 to 28.190 |
| B (Lomustine only) | 20.3 | 16.490 to 25.360 |
| Comparison of survival curves (Stratified Logrank test) | | Significance P = 0.7032 |
| Hazard ratios (95% Confidence Intervals) | | 0.95 (0.74 to 1.23) |

TABLE 6

Progression Free Survival (PFS) Results for Patients-Summary Statistics

| Arm | Number of Events | | Number Censored | | |
|---|---|---|---|---|---|
| | N | % total sample size | N | % total sample size | Total Sample Size |
| A (lomustine + eflornithine) | 95 | 55.2 | 77 | 44.8 | 172 |
| B (Lomustine only) | 87 | 50.9 | 84 | 49.1 | 171 |
| Overall | 182 | 53.1 | 161 | 46.9 | 343 |

| Arm | Median PFS | 95% CI for the Median |
|---|---|---|
| A (lomustine + eflornithine) | 8.871 | 4.567 to 12.060 |
| B (Lomustine only) | 7.228 | 5.520 to 10.380 |
| Comparison of survival curves (Stratified Logrank test) | | Significance P = 0.4319 |
| Hazard ratios (95% Confidence Intervals) | | 0.88 (0.65 to 1.20) |

The improvement in treatment outcome (a combination of eflornithine and lomustine compared to lomustine alone) as measured by OS and PFS was significantly more pronounced when analyzing patient groups with particular genetic profiles. The overall survival (OS) (primary endpoint) rates are summarized in Table 7. The results demonstrate that, among other things, when eflornithine was added to lomustine in patients with astrocytoma that progressed/recured after irradiation and adjuvant temozolomide chemotherapy, patient groups with certain genetic profiles demonstrate superiority in overall survival (OS) and comparable safety compared to those taking lomustine alone. For example, there was statistically significant improvement of OS in grade 3 Astrocytoma patients when adding eflornithine to lomustine when compared to lomustine alone.

The progression free survival (PFS) (secondary endpoint) rates are summarized in Table 8. The results demonstrate that, among other things, when eflornithine was added to lomustine in patients with astrocytoma that progressed/recured after irradiation and adjuvant temozolomide chemotherapy, patient groups with certain genetic profiles demonstrate superiority in progression free survival (PFS) and comparable safety compared to those taking lomustine alone. For example, there was statistically significant improvement of PFS in grade 3 Astrocytoma patients when adding eflornithine to lomustine when compared to lomustine alone.

TABLE 7

| | N (Patients) | Arm A mOS (Months) | Arm B mOS (Months) | mOS Benefit (Months) | Hazardous Ratio (HR) | P-value |
|---|---|---|---|---|---|---|
| Results-Primary Endpoint: Overall Survival (OS) | | | | | | |
| Intention to treat (ITT) | 343 | 23.4 | 20.3 | 3.1 | 0.95 | NS |
| ITT recurrent grade 4 Glioblastoma | 106 | 13.4 | 13.6 | 1.1 | 1.40 | NS |
| ITT recurrent grade 3 & 4 Astrocytoma | 237 | 28.5 | 22.3 | 6.2 | 0.76 | 0.0953 |
| ITT recurrent grade 3 Astrocytoma | 196 | 34.9 | 23.5 | 11.4 | 0.64 | 0.0136 |

TABLE 8

| | N (Patients) | Arm A mOS (Months) | Arm B mOS (Months) | mOS Benefit (Months) | Hazardous Ratio (HR) | P-value |
|---|---|---|---|---|---|---|
| Results-Secondary Endpoint: Progression Free Survival (PFS) | | | | | | |
| Intention to treat (ITT) | 343 | 8.9 | 7.2 | 1.7 | 0.88 | NS |
| ITT recurrent grade 4 Glioblastoma | 106 | 3.4 | 6.8 | −3.4 | 1.41 | NS |
| ITT recurrent grade 3 & 4 Astrocytoma | 237 | 12.3 | 7.3 | 5.0 | 0.68 | 0.0511 |
| ITT recurrent grade 3 Astrocytoma | 196 | 15.8 | 7.2 | 8.6 | 0.58 | 0.0113 |

The data described herein (e.g., in Tables 5-12) presents an update to an earlier version of the data included in the priority document due to further analysis. For example, upon further molecular analysis of patient tumor tissue samples, certain patients that were originally classified as grade 4 glioblastoma were re-classified as grade 3&4 astrocytoma.

As described herein, the grade classification is used in accordance with WHO 2021 classification. For example, grade 4 glioblastoma refers glioma with wildtype IDH (e.g., IDH1, IDH2). Grade 3 astrocytoma refers to glioma with mutant IDH (either IDH1 or IDH2) and no homozygous deletion of CDKN2A/B. Grade 4 astrocytoma refers to glioma with mutant IDH (either IDH1 or IDH2) and homozygous deletion of CDKN2A/B.

Example 3—Human Clinical Trials—Phase 3—Subset Analysis

Figure 4:
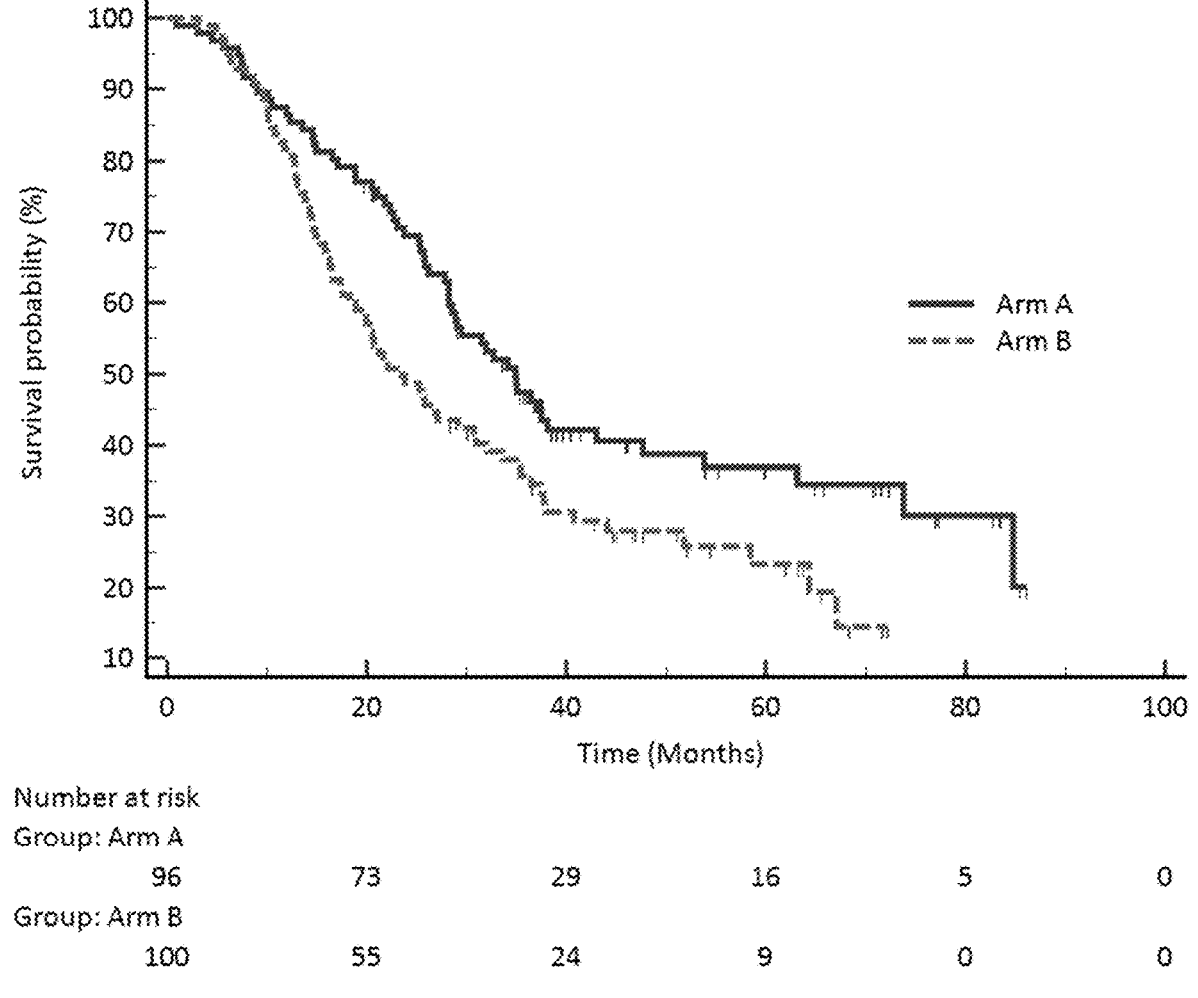
FIG. 4 shows overall survival (OS) results for patients with mutant IDH (IDH1 or IDH2) and intact CDKN2A/B genes with further summary statistics in Table 9.
Figure 5:
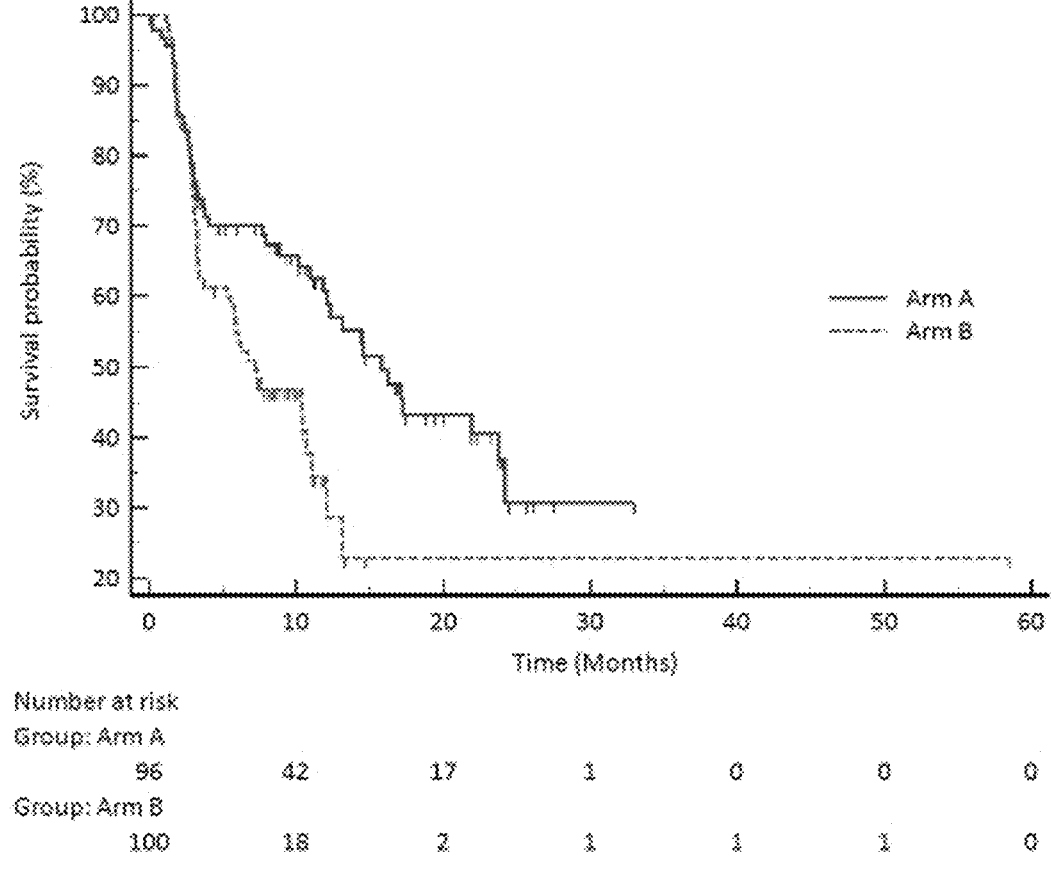
FIG. 5 shows progression free survival (PFS) results for patients with mutant IDH (IDH1 or IDH2) mutant and intact CDKN2A/B genes with further summary statistics in Table 10.

The present Example demonstrates the impact of genetic profiles (e.g., status of CDKN2A/B, status of ATRX, etc.) on the treatment outcome of eflornithine and lomustine compared to lomustine alone. Subset analysis was performed for the patients with astrocytoma characterized by IDH (IDH1 or IDH2) mutation and no homozygous deletion of CDKN2A/B genes. The analysis illustrated that addition of eflornithine to the standard of care significantly improved OS and PFS in such patient groups (FIG. 4 and Table 9; and FIG. 5 and Table 10).

TABLE 9

Overall Survival (OS) Results for Patients with IDH (IDH1 or IDH2) Mutant and CDKN2A/B intact-Summary Statistics

| | Number of Events | | Number Censored | | |
|---|---|---|---|---|---|
| Arm | N | % total sample size | N | % total sample size | Total Sample Size |
| A (lomustine + eflornithine) | 59 | 61.4 | 37 | 38.5 | 96 |
| B (Lomustine only) | 72 | 72.0 | 28 | 28.0 | 100 |
| Overall | 131 | 66.8 | 65 | 33.2 | 196 |

| Arm | Median OS | 95% CI for the Median |
|---|---|---|
| A (lomustine + eflornithine) | 34.92 | 28.220 to 47.640 |
| B (Lomustine only) | 23.49 | 18.890 to 32.100 |
| Comparison of survival curves (Stratified Logrank test) | Significance P = 0.0136 | |
| Hazard ratio (95% Confidence Intervals) | 0.64 (0.46 to 0.92) | |

TABLE 10

Progression Free Survival (PFS) Results for Patients with (IDH1 or IDH2) Mutant and CDKN2A/B intact-Summary Statistics

| Arm | Number of Events | | Number Censored | | |
| | N | % total sample size | N | % total sample size | Total Sample Size |
| --- | --- | --- | --- | --- | --- |
| A (lomustine + eflornithine) | 44 | 45.8 | 52 | 54.16 | 96 |
| B (Lomustine only) | 50 | 50.0 | 50 | 50.0 | 100 |
| Overall | 94 | 48.0 | 100 | 51.0 | 196 |

| Arm | Median PFS | 95% CI for the Median |
| --- | --- | --- |
| A (lomustine + eflornithine) | 15.8 | 11.830 to 24.180 |

TABLE 10-continued

Progression Free Survival (PFS) Results for Patients with (IDH1 or IDH2) Mutant and CDKN2A/B intact-Summary Statistics

| B (Lomustine only) | 7.228 | 3.713 to 11.070 |
| --- | --- | --- |
| Comparison of survival curves (Stratified Logrank test) | | Significance P = 0.0113 |
| Hazard ratios a with 95% Confidence Interval | | 0.5894 0.3837 to 0.9055 |

Figure 6:
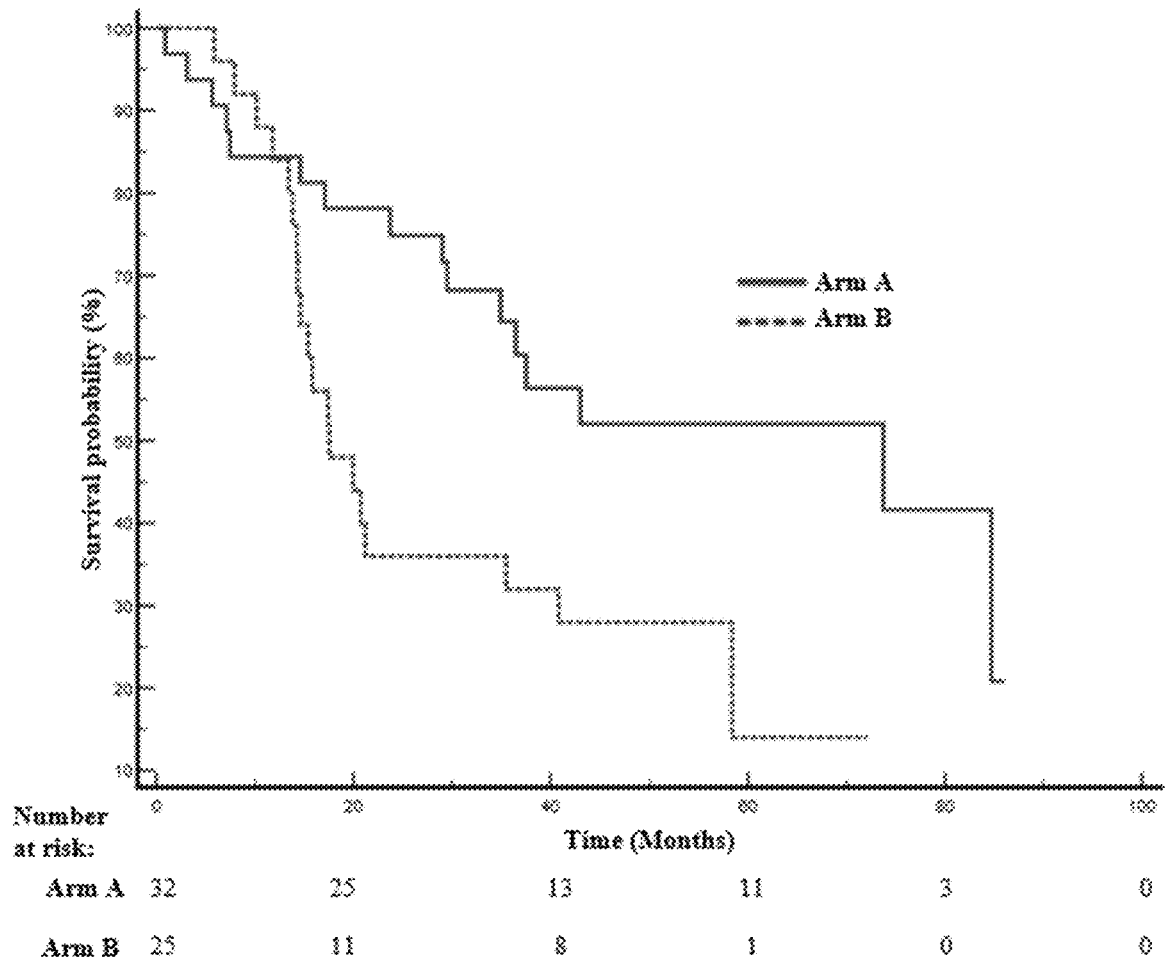
FIG. 6 shows overall survival (OS) results for patients with mutant IDH (IDH1 or IDH2), intact CDKN2A/B and intact ATRX with further summary statistics in Table 11.
Figure 7:
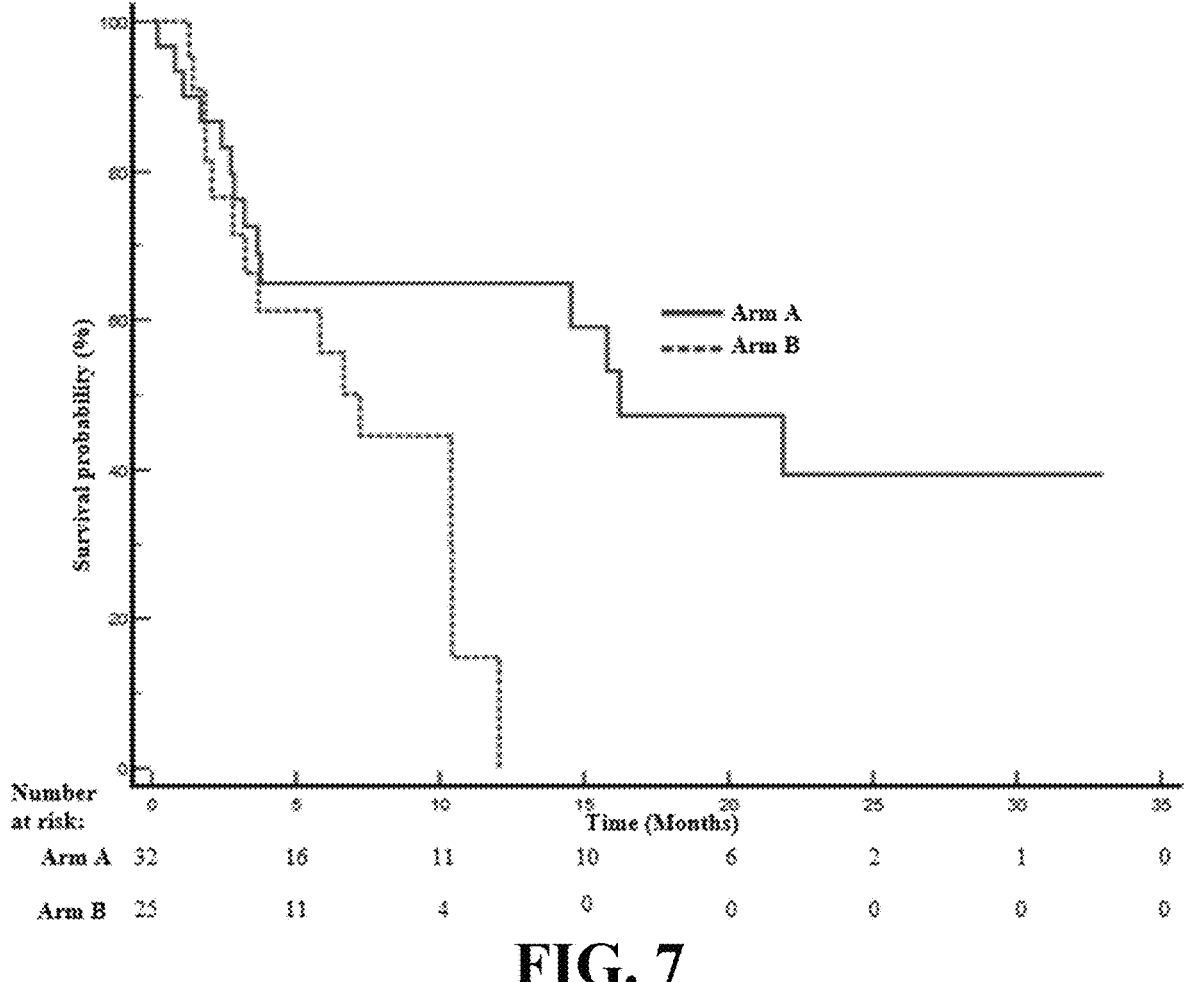
FIG. 7 shows progression free survival (PFS) results for patients with mutant IDH (IDH1 or IDH2), intact CDKN2A/B and intact ATRX with further summary statistics in Table 12.

Subset analysis was performed for the patients with astrocytoma characterized by IDH (IDH1 or ID 2) mutation and no homozygous deletion of CDKN2A/B genes, in addition to intact ATRX. The analysis illustrated that addition of eflornithine to the standard of care significantly improved OS and PFS in such patient groups (FIG. 6 and Table 11; and FIG. 7 and Table 12).

TABLE 11

Overall Survival (OS) Results for Patients with IDH (IDH1 or IDH2) Mutant, CDKN2A/B and ATRX intact-Summary Statistics

| Arm | Number of Events | | Number Censored | | |
| | N | % total sample size | N | % total sample size | Total Sample Size |
| --- | --- | --- | --- | --- | --- |
| A (lomustine + eflornithine) | 16 | 50 | 16 | 50 | 32 |
| B (Lomustine only) | 19 | 76 | 6 | 24 | 25 |
| Overall | 35 | 61.4 | 22 | 38.6 | 57 |

| Arm | Mean OS | SE | 95% CI for the Median | Median OS | 95% CI for the Median |
| --- | --- | --- | --- | --- | --- |
| A (lomustine + eflornithine) | 53.858 | 5.985 | 42.128 to 65.588 | 73.76 | 29.500 to 84.730 |
| B (Lomustine only) | 30.699 | 4.745 | 21.398 to 40.000 | 17.54 | 14.320 to 40.800 |
| Comparison of survival curves (Stratified Logrank test) | | | Significance P = 0.0156 | | |
| Hazard ratios (95% Confidence Intervals) | | | 0.4151 (0.2035 to 0.8466) | | |

TABLE 12

Progression Free Survival (PFS) Results for Patients with IDH (IDH1 or IDH2) Mutant, CDKN2A/B and ATRX intact-Summary Statistics

| Arm | Number of Events | | Number Censored | | |
| | N | % total sample size | N | % total sample size | Total Sample Size |
| --- | --- | --- | --- | --- | --- |
| A (lomustine + eflornithine) | 14 | 43.8 | 18 | 56.3 | 32 |
| B (Lomustine only) | 14 | 56 | 11 | 44 | 25 |
| Overall | 28 | 49.1 | 29 | 50.9 | 57 |

TABLE 12-continued

Progression Free Survival (PFS) Results for Patients with IDH (IDH1 or IDH2) Mutant, CDKN2A/B and ATRX intact-Summary Statistics

| Arm | Median PFS | 95% CI for the Median |
|---|---|---|
| A (lomustine + eflornithine) | 16.23 | 3.680 to 21.910 |
| B (Lomustine only) Comparison of survival curves (Stratified Logrank test) | 7.228 | 2.825 to 12.060 Significance P = 0.0361 |
| Hazard ratios (95% Confidence Interval) | | 0.4072 (0.1758 to 0.9433) |

The comparison of the two subgroups of patients (Table 13) showed that while the subset of patients without regard to their ATRX mutation status have showed improved OS and PFS when treated with eflornithine and lomustine compared to lomustine alone, such improvement increased by about 10-fold in patients who have IDH (IDH1 or IDH2) mutation, intact CDK2A/B and intact ATRX.

TABLE 13

Effect of Eflornithine on OS and PFS in Patient Populations with IDH (IDH1 or IDH2) Mutation

| Arm | Patients with CDKN2A/B Intact (irrespective of ATRX status) | | Patients with both CDKN2A/B and ATRX Intact | |
|---|---|---|---|---|
| | Median OS (months) | Median PFS (Months) | Median OS (months) | Median PFS (Months) |
| A (lomustine + eflornithine) | 35 | 16 | 74 | 16 |
| B (Lomustine only) | 24 | 7 | 8 | 7 |
| P-value | 0.0188 | 0.0158 | 0.0156 | 0.0158 |

Example 4—IDH Mutation Detection—IDH1/2 PCR Assay

As appreciated by those skilled in the art, various methods, e.g., immunohistochemistry, Western blot, immunocytochemistry, etc. are known in the art to detect mutations in IDH genes. The present Example demonstrates a method of detecting mutations in 1DH genes. Detection of mutations at IDH1 codons R132X and R100Q and at 1DH2 codons R140X and R172X was performed using real-time PCR conducted by NeoGenomics (i.e.: https://neogenomics.com/test-menu/idh1idh2-mutation-analysis-pcr). The real-time PCR-based assay detected somatic mutations in exon 4 of the IDH1 and IDH2 genes. The real-time PCR assay used allele-specific primers to identify the presence of IDH1 and IDH2 mutations in 5 separate reaction mixes per sample. The assay was designed to preferentially amplify mutant DNA, even in samples that contain mostly wild-type DNA. The amplification product was detected by hydrolysis probes. Probes complimentary to the IDH1 and IDH2 genes are labeled with the FAM (5'6-FAM is a fluorescein probe for oligonucleotides) fluorophore, while the probe complimentary to the endogenous control gene was tagged with the VIC (an asymmetric xanthene dye with fluorescence in the yellow-green part of the spectrum) fluorophore. Signal from the VIC tagged probe indicated that there was sufficient amplifiable DNA template in the reaction, while a signal from the FAM fluorophore indicated the presence of a mutation. The sample required for the assays included: 5 mL in EDTA tube for peripheral blood, 2 mL in EDTA tube for bone marrow, or a paraffin block (alternatively 1 H&E slide plus 5-10 unstained slides cut at 5 or more microns with positively-charged slides and 10% NBF fixative) for FFPE solid tumor tissue.

Example 5—CDKN2A/B FISH Assay

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In the present Example, the DNA probe was labeled with a fluorescent molecule or a hapten, in the form of fluor-dUTP, digoxigenin-dUTP, biotin-dUTP or hapten-dUTP which was incorporated in the DNA using enzymatic reactions, such as nick translation or PCR. The sample containing the genetic material (the chromosomes) was placed on glass slides and was denatured by a formamide treatment. The labeled probe was then hybridized with the sample containing the genetic material under suitable conditions. After the hybridization, the sample was viewed either directly (in the case of a probe labeled with fluorine) or indirectly (using fluorescently labeled antibodies to detect the hapten).

Detection of homozygous deletions of CDKN2A/B (also called p16) was performed by CDKN2A/B FISH assay conducted by NeoGenomics (i.e.: https://neogenomics.com/test-menu/cdkn2ab-p16-deletion-mesothelioma-or-glioma). NeoGenomics FISH assay procedure was similar to Agilent DAKO Histology FISH Kit (Code K5799; see: https://www.agilent.com/en/product/molecular-pathology/ish-ancillaries-accessories/ish-ancillaries-accessories-%28manual%29/histology-fish-accessory-kit-76860 pdf manual), but used Agilent probes CDKN2A and CEP9. While morphologic, immunocytochemical, and immunohistochemical analyses determine the mesothelial origin of such neoplasms, CDKN2A/B FISH enabled differentiation of benign from malignant proliferations with high specificity and positive predictive value, particularly when combined with BAP-1 IHC. The CDKN2A/B FISH determined the presence of CDKN2A homozygous deletion, CDKN2A heterozygous deletion, or chromosome 9 monosomy. The sample required the assays included: a paraffin block or H&E slide (plus 4 unstained slides cut at 4-5 microns).

The examples and embodiments described herein are for illustrative purposes only and various modifications or changes suggested to persons skilled in the art are to be included within the spirit and purview of this application and scope of the appended claims.

What is claimed is:

1. A method of treating glioma, comprising the steps of:
   (a) selecting a subject with mutant IDH and no homozygous deletion of CDKN2A/B genes; and
   (b) administering to said subject eflornithine or a salt thereof.

2. The method of claim 1, wherein the mutant IDH gene is mutant IDH1 gene or mutant IDH2 gene.

3. The method of claim 1, wherein the subject further has intact ATRX gene.

4. The method of claim 1, wherein the eflornithine or a salt thereof is eflornithine.

5. The method of claim 1, wherein the eflornithine or a salt thereof is eflornithine hydrochloride salt.

6. The method of claim 1, wherein eflornithine or a salt thereof is administered at a dose from about 1.4 $g/m^2$ to about 3.5 $g/m^2$ three-times daily free base equivalent.

7. The method of claim 6, wherein eflornithine or a salt thereof is administered at a dose of about 2.8 $g/m^2$ three-times daily free base equivalent.

8. The method of claim 7, wherein eflornithine or a salt thereof is administered daily on a two-week-on followed by a one-week-off schedule.

9. The method of claim 1, wherein the method further comprises administering to said subject a chemotherapeutic agent.

10. The method of claim 9, wherein the chemotherapeutic agent is lomustine.

11. The method of claim 10, wherein lomustine is administered at a dose from about 50 $mg/m^2$ to about 110 $mg/m^2$.

12. The method of claim 11, wherein lomustine is administered at a dose of about 90 $mg/m^2$.

13. The method of claim 10, wherein eflornithine or a salt thereof is administered at a dose of about 2.8 $g/m^2$ three-times daily free base equivalent on a two-week-on followed by a one-week-off schedule, and lomustine is administered at a dose of about 90 $mg/m^2$ every 6 weeks, wherein lomustine is administered on a day in the off-week of the treatment schedule of eflornithine or a salt thereof.

14. The method of claim 13, wherein eflornithine or a salt thereof is administered daily on Days 1-14 and Days 22-35, and lomustine is administered on Day 15, Day 16, or Day 17.

15. The method of claim 14, wherein eflornithine or a salt thereof is administered in one or more cycles of treatment period and each cycle comprises about 6 weeks.

16. The method of claim 1, wherein the glioma is temozolomide recurrent/refractory glioma.

17. The method of claim 1, wherein the glioma is grade 2 astrocytoma.

18. The method of claim 1, wherein the glioma is grade 3 astrocytoma.

19. A method of treating glioma in a subject with mutant IDH gene and no homozygous deletion of CDKN2A/B genes, comprising administering to the subject eflornithine or a salt thereof.

20. A method of treating glioma in a subject, comprising screening for and selecting a subject with mutant IDH gene and no homozygous deletion of CDKN2A/B genes, and administering to the subject eflornithine or a salt thereof.

* * * * *